United States Patent
Lindhout et al.

(10) Patent No.: US 10,869,909 B2
(45) Date of Patent: Dec. 22, 2020

(54) COMPOSITIONS AND METHODS OF USE FOR TREATING METABOLIC DISORDERS

(71) Applicant: NGM Biopharmaceuticals, Inc., South San Francisco, CA (US)

(72) Inventors: Darrin Anthony Lindhout, Mountain View, CA (US); Peng Zhang, Fremont, CA (US); Thomas Frederick Parsons, Oakland, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 54 days.

(21) Appl. No.: 16/221,139

(22) Filed: Dec. 14, 2018

(65) Prior Publication Data
US 2019/0183974 A1 Jun. 20, 2019

Related U.S. Application Data

(63) Continuation of application No. 15/377,679, filed on Dec. 13, 2016, now Pat. No. 10,195,250, which is a
(Continued)

(51) Int. Cl.
| | |
|---|---|
| A61K 38/18 | (2006.01) |
| C07K 14/475 | (2006.01) |
| A61K 38/38 | (2006.01) |
| A61K 39/395 | (2006.01) |
| C07K 14/495 | (2006.01) |
| A61K 38/00 | (2006.01) |
| A61K 39/00 | (2006.01) |
| A61K 45/06 | (2006.01) |
| A61K 47/60 | (2017.01) |

(52) U.S. Cl.
CPC .......... *A61K 38/18* (2013.01); *A61K 38/1841* (2013.01); *A61K 38/38* (2013.01); *A61K 39/3955* (2013.01); *A61K 45/06* (2013.01); *A61K 47/60* (2017.08); *C07K 14/475* (2013.01); *C07K 14/495* (2013.01); *A61K 38/00* (2013.01); *A61K 2039/505* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,194,596 A | 3/1993 | Tischer |
| 5,350,836 A | 9/1994 | Kopchick |

(Continued)

FOREIGN PATENT DOCUMENTS

| | | |
|---|---|---|
| CL | 201700201 | 1/2017 |
| CN | 102046207 | 5/2011 |

(Continued)

OTHER PUBLICATIONS

Griner et al., "Growth Differentiation Factor 15 Stimulates Rapamycin-Sensitive Ovarian Cancer Cell Growth and Invasion," Biochemical Pharmacology, 2013, 85(1):46-58.
(Continued)

*Primary Examiner* — Elizabeth C. Kemmerer
(74) *Attorney, Agent, or Firm* — Fish & Richardson P.C.

(57) ABSTRACT

Methods of treating individuals with a glucose metabolism disorder and/or a body weight disorder, and compositions associated therewith, are provided.

34 Claims, 20 Drawing Sheets
Specification includes a Sequence Listing.

Related U.S. Application Data continuation of application No. 14/373,617, filed as application No. PCT/US2013/029955 on Mar. 8, 2013, now Pat. No. 9,550,819.

(60) Provisional application No. 61/616,294, filed on Mar. 27, 2012.

(56) References Cited

U.S. PATENT DOCUMENTS

| | | |
|---|---|---|
| 5,731,168 A | 3/1998 | Carter et al. |
| 5,876,969 A | 3/1999 | Fleer et al. |
| 5,994,102 A | 11/1999 | Hudson et al. |
| 6,051,424 A | 4/2000 | Kato et al. |
| 6,107,476 A | 8/2000 | Erlander et al. |
| 6,165,470 A | 12/2000 | Becquart et al. |
| 6,180,602 B1 | 1/2001 | Kato et al. |
| 6,420,543 B1 | 7/2002 | Lee et al. |
| 6,465,181 B2 | 10/2002 | Biling-Medel et al. |
| 6,500,638 B2 | 12/2002 | Hudson et al. |
| 6,521,227 B1 | 2/2003 | Hudson et al. |
| 6,524,802 B1 | 2/2003 | Lee et al. |
| 6,686,179 B2 | 2/2004 | Fleer et al. |
| 6,905,688 B2 | 6/2005 | Rosen et al. |
| 6,972,322 B2 | 12/2005 | Fleer et al. |
| 6,989,365 B2 | 1/2006 | Fleer et al. |
| 7,056,701 B2 | 6/2006 | Fleer et al. |
| 7,081,354 B2 | 7/2006 | Fleer et al. |
| 7,094,577 B2 | 8/2006 | Fleer et al. |
| 7,141,661 B2 | 11/2006 | Eling et al. |
| 7,157,235 B2 | 1/2007 | Breit et al. |
| 7,244,833 B2 | 7/2007 | Yu et al. |
| 7,276,593 B2 | 10/2007 | Vernet et al. |
| 7,282,351 B2 | 10/2007 | Hudson et al. |
| 7,348,004 B2 | 3/2008 | Peters et al. |
| 7,410,779 B2 | 8/2008 | Fleer et al. |
| 7,435,410 B2 | 10/2008 | Fleer et al. |
| 7,442,371 B2 | 10/2008 | Yu et al. |
| 7,514,221 B2 | 4/2009 | Breit et al. |
| 7,754,689 B2 | 7/2010 | Lu et al. |
| 7,833,521 B2 | 11/2010 | Fleer et al. |
| 7,863,239 B2 | 1/2011 | Timmerman et al. |
| 7,919,084 B2 | 4/2011 | Breit et al. |
| 7,968,303 B2 | 6/2011 | Breit et al. |
| 8,021,880 B2 | 9/2011 | Peters et al. |
| 8,067,548 B2 | 11/2011 | Wang et al. |
| 8,084,021 B2 | 12/2011 | Yu et al. |
| 8,192,735 B2 | 6/2012 | Breit et al. |
| 8,222,384 B2 | 7/2012 | Wolfman et al. |
| 8,252,739 B2 | 8/2012 | Rosen et al. |
| 8,592,532 B2 | 11/2013 | Breit et al. |
| 8,592,562 B2 | 11/2013 | Kannan et al. |
| 8,946,146 B2 | 2/2015 | Breit et al. |
| 8,986,698 B2 | 3/2015 | Arnason et al. |
| 9,161,966 B2 | 10/2015 | Matern et al. |
| 9,550,819 B2 | 1/2017 | Lindhout et al. |
| 9,714,276 B2 | 7/2017 | Xiong et al. |
| 9,827,291 B2 | 11/2017 | Matern et al. |
| 9,828,415 B2 | 11/2017 | Matern et al. |
| 9,834,586 B2 | 12/2017 | Lindhout et al. |
| 9,862,752 B2 | 1/2018 | Xiong et al. |
| 9,920,118 B2 | 3/2018 | Shen |
| 10,195,250 B2 | 2/2019 | Lindhout et al. |
| 10,323,075 B2 | 6/2019 | Matern et al. |
| 10,336,798 B2 | 7/2019 | Xiong et al. |
| 10,562,965 B2 | 2/2020 | Shen et al. |
| 10,610,568 B2 | 4/2020 | Matern et al. |
| 2001/0011077 A1 | 8/2001 | Albone et al. |
| 2003/0023073 A1 | 1/2003 | Hsiao et al. |
| 2003/0053431 A1 | 3/2003 | Madour et al. |
| 2003/0232347 A1 | 12/2003 | Anderson et al. |
| 2003/0232385 A1 | 12/2003 | Breit et al. |
| 2004/0029770 A1 | 2/2004 | Baek et al. |
| 2004/0053325 A1 | 3/2004 | Breit et al. |
| 2004/0253207 A1 | 12/2004 | Hruska et al. |
| 2006/0148709 A1 | 7/2006 | Unsicker et al. |
| 2006/0253913 A1 | 11/2006 | Huang et al. |
| 2007/0077598 A1 | 4/2007 | Breit et al. |
| 2007/0166310 A1 | 7/2007 | Hudson et al. |
| 2009/0004181 A1 | 1/2009 | Breit et al. |
| 2009/0042780 A1 | 2/2009 | Knopf et al. |
| 2009/0291889 A1 | 11/2009 | Breit et al. |
| 2010/0112692 A1 | 5/2010 | Rezania et al. |
| 2010/0184217 A1 | 7/2010 | Cegilski et al. |
| 2010/0221777 A1 | 9/2010 | Choe et al. |
| 2010/0261284 A1 | 10/2010 | Spanuth |
| 2010/0266707 A1 | 10/2010 | Breit et al. |
| 2010/0278843 A1 | 11/2010 | Breit et al. |
| 2010/0286067 A1 | 11/2010 | DeFrees |
| 2011/0033886 A1 | 2/2011 | Hess et al. |
| 2011/0039284 A1 | 2/2011 | Breit et al. |
| 2011/0065204 A1 | 3/2011 | Wollert et al. |
| 2011/0107821 A1 | 5/2011 | Hess et al. |
| 2011/0123454 A1 | 5/2011 | Breit et al. |
| 2011/0257022 A1 | 10/2011 | Hess et al. |
| 2011/0262444 A1 | 10/2011 | Kim et al. |
| 2011/0263443 A1 | 10/2011 | Hess et al. |
| 2011/0300562 A1 | 12/2011 | Lambrecht et al. |
| 2012/0107420 A1 | 5/2012 | Breit et al. |
| 2012/0128624 A1 | 5/2012 | Yu et al. |
| 2012/0309697 A1 | 12/2012 | Breit et al. |
| 2013/0004484 A1 | 1/2013 | Demeule et al. |
| 2013/0071935 A1 | 3/2013 | Bergman et al. |
| 2013/0323835 A1 | 12/2013 | McDonald et al. |
| 2014/0044674 A1 | 2/2014 | Duerner et al. |
| 2014/0086915 A1 | 3/2014 | Breit et al. |
| 2014/0113370 A1 | 4/2014 | Camphausen et al. |
| 2014/0193427 A1 | 7/2014 | Lerner et al. |
| 2014/0199294 A1 | 7/2014 | Mimoto et al. |
| 2014/0213511 A1 | 7/2014 | Matern et al. |
| 2014/0314711 A1 | 10/2014 | Scheer et al. |
| 2014/0378665 A1 | 12/2014 | Xiong et al. |
| 2015/0023960 A1 | 1/2015 | Lindhout et al. |
| 2015/0307575 A1 | 10/2015 | Xiong et al. |
| 2015/0322081 A1 | 11/2015 | Hoehn |
| 2016/0031960 A1 | 2/2016 | Lindhout et al. |
| 2016/0120999 A1 | 5/2016 | Shen et al. |
| 2016/0129082 A1 | 5/2016 | Matern et al. |
| 2016/0168213 A1 | 6/2016 | Xiong et al. |
| 2016/0193295 A1 | 7/2016 | Kannan |
| 2016/0200787 A1 | 7/2016 | Matern et al. |
| 2017/0246249 A1 | 8/2017 | Lindhout et al. |
| 2017/0291929 A1 | 10/2017 | Xiong et al. |
| 2018/0079790 A1 | 3/2018 | Xiong et al. |
| 2018/0099025 A1 | 4/2018 | Matern et al. |
| 2018/0100003 A1 | 4/2018 | Matern et al. |
| 2018/0134761 A1 | 5/2018 | Lindhout et al. |
| 2018/0237514 A1 | 8/2018 | Shen et al. |
| 2019/0000923 A1 | 1/2019 | Chutkow et al. |
| 2020/0087366 A1 | 3/2020 | Matern et al. |
| 2020/0140536 A1 | 5/2020 | Shen et al. |
| 2020/0165314 A1 | 5/2020 | Lindhout et al. |

FOREIGN PATENT DOCUMENTS

| | | |
|---|---|---|
| EP | 1179067 | 12/2006 |
| EP | 1279039 | 1/2008 |
| EP | 1914554 | 4/2008 |
| EP | 0833912 | 2/2009 |
| EP | 2383571 | 11/2011 |
| EP | 2439535 | 4/2012 |
| EP | 2441466 | 4/2012 |
| EP | 2774620 | 9/2014 |
| EP | 2929891 | 10/2015 |
| EP | 3174894 | 6/2017 |
| JP | 07258293 | 10/1995 |
| JP | 1995250688 | 10/1995 |
| JP | 2003532079 | 10/2003 |
| JP | 2006505617 | 2/2006 |
| JP | 2009539767 | 11/2009 |
| JP | 2014-511863 | 5/2014 |
| WO | WO199403599 | 2/1994 |
| WO | WO199618730 | 6/1996 |
| WO | WO199700958 | 1/1997 |

(56) References Cited

FOREIGN PATENT DOCUMENTS

| WO | WO199736926 | 10/1997 |
| WO | WO199811224 | 3/1998 |
| WO | WO199906445 | 2/1999 |
| WO | WO 2001/070968 | 9/2001 |
| WO | WO200181928 | 11/2001 |
| WO | WO2002092620 | 11/2002 |
| WO | WO 2004/043385 | 5/2004 |
| WO | WO2005099746 | 10/2005 |
| WO | WO2005113585 | 12/2005 |
| WO | WO2006000448 | 1/2006 |
| WO | WO 2007/143161 | 12/2007 |
| WO | WO2008013454 | 1/2008 |
| WO | WO2009021293 | 2/2009 |
| WO | WO2009046495 | 4/2009 |
| WO | WO 2009/058285 | 5/2009 |
| WO | WO 2009/089004 | 7/2009 |
| WO | WO2009141357 | 11/2009 |
| WO | WO2010019263 | 2/2010 |
| WO | WO2010048670 | 5/2010 |
| WO | WO2010093925 | 8/2010 |
| WO | WO2010099219 | 9/2010 |
| WO | WO2010129503 | 11/2010 |
| WO | WO2011005621 | 1/2011 |
| WO | WO2011050407 | 5/2011 |
| WO | WO2011057120 | 5/2011 |
| WO | WO2011064758 | 6/2011 |
| WO | WO2011127458 | 10/2011 |
| WO | WO2012025355 | 3/2012 |
| WO | WO2012138919 | 10/2012 |
| WO | WO2013113008 | 8/2013 |
| WO | WO2013148117 | 10/2013 |
| WO | WO2014000042 | 1/2014 |
| WO | WO 2014/100689 | 6/2014 |
| WO | WO2014100689 | 6/2014 |
| WO | WO 2014/120619 | 8/2014 |
| WO | WO2015017710 | 2/2015 |
| WO | WO 2016/018931 | 2/2016 |

OTHER PUBLICATIONS

Guoqiang et al., "Correlation between serum GDF-15 expression level and coronary heart disease," Modern Preventive Medicine, 2012, 39(20):5380-3.
PCT International Preliminary Report on Patentability in International Appln. No. PCT/US2013/02995, dated Oct. 1, 2014, 8 pages.
PCT International Preliminary Report on Patentability in International Appln. No. PCT/US2014/013232, dated Aug. 4, 2015, 8 pages.
PCT International Preliminary Report on Patentability in International Appln. No. PCT/US2015/058111, dated May 2, 2017, 9 pages.
PCT International Preliminary Report on Patentability in international Appln. No. PCT/US2015/42510, dated Jan. 31, 2017, 8 pages.
PCT International Search Report and Written Opinion in International Appln. No. PCT International PCT/US2013/029955, dated May 31, 2013, 11 pages.
PCT International Search Report and Written Opinion in International Appln. No. PCT/US2014/013232, dated Jul. 9, 2014, 13 pages.
PCT International Search Report and Written Opinion in International Appln. No. PCT/US2015/058111, dated Dec. 27, 2015, 12 pages.
PCT International Search Report and Written Opinion in International Appln. No. PCT/US2015/42510, dated Jan. 4, 2016, 12 pages.
Ridgway et al, "'Knobs-into-holes' Engineering of Antibody CH3 Domains for Heavy Chain Heterodimerization," Protein Engineering, Oxford University Press, Jan. 1996, 9(7):617-621.
Sinobiological.com [online] "GDF15 Protein, Human, Recombinant (Fc Tag)," May 1, 2010, retrieved on Oct. 14, 2019, retrieved from URL http://www.sinobiological.com/GDF-15-Protein-g-570.html, 4 pages.

U.S. Appl. No. 14/811,578, U.S. Pat. No. 9,834,586, filed Jul. 28, 2015, Lindhout.
U.S. Appl. No. 15/801,198, filed Nov. 1, 2017, Lindhout.
U.S. Appl. No. 16/784,877, filed Feb. 7, 2020, Lindhout.
U.S. Appl. No. 14/927,153, U.S. Pat. No. 9,920,118, filed Oct. 29, 2015, Shen.
U.S. Appl. No. 15/885,438, U.S. Pat. No. 10,562,965, filed Jan. 31, 2018, Shen.
U.S. Appl. No. 16/743,712, filed Jan. 15, 2020, Shen.
U.S. Appl. No. 14/373,617, U.S. Pat. No. 9,550,819, filed Jul. 21, 2014, Lindhout.
U.S. Appl. No. 15/377,679, U.S. Pat. No. 10,195,250, filed Dec. 13, 2016, Lindhout.
U.S. Appl. No. 14/763,262, U.S. Pat. No. 9,828,415, filed Jul. 24, 2015, Matern.
U.S. Appl. No. 14/165,391, U.S. Pat. No. 9,161,966, filed Jan. 27, 2014, Matern.
U.S. Appl. No. 14/846,194, U.S. Pat. No. 9,827,291, filed Sep. 4, 2015, Matern.
U.S. Appl. No. 15/789,753, U.S. Pat. No. 10,610,568, filed Oct. 20, 2017, Matern.
U.S. Appl. No. 15/789,679, U.S. Pat. No. 10,323,075, filed Oct. 20, 2017, Matern.
U.S. Appl. No. 16/397,578, filed Apr. 29, 2019, Matern.
"Glucose metabolism disroders" http:ctdbase.orgdetail.go?type=disease&acc=MESH%3AD044882 Mar. 25, 2016 1 page.
Bauskin et al. (2000} "The Propeptide of Macrophage Inhibitory Cytokine (MIC-1} a TGF-b Superfamily Member Acts as a Quality Control Determinant for Correctly Folded MIC-1" EMBOJ 19:2212-2220.
Bauskin et al. (2005} "The Propeptide Mediates Formation of Stromal Stores of PROMIC-1: Role in Determining Prostate Cancer Outcome" Cancer Research 65(6) 2330-2336.
Bauskin et al. (2010) "The TGF-superfamily cytokine MIC-1GDF15: secretory mechanisms facilitate creation of latent stromal stores" Journal of Interferon & Cytokine Research V., pp. 389-397.
Benjamin et al. (1998) "A plasticity window for blood vessel remodeling is defined by pericyte coverage of the preformed endothelial network and is regulated by PDGF-B and VEGF" Development 125:1591-1598.
Bootcov et al. (1997) "MIC-1 a novel macrophage inhibitory cytokine is a divergent member of the TGF-beta superfamily" Proc. Nat/. Acad. Sci. USA 94:11514-11519.
Bottner et al. (1999) "Characterization of the rat mouse and human genes of growthdifferentiation factor-15macrophage inhibiting cytokine-1 (GDF-15MIC-1)" Gene, pp. 105-111, vol. 237.
Breit et al. (2011) "The TGF-beta superfamily cytokine MIC-1 GDF15: a pleotrophic cytokine with roles in inflammation cancer and metabolism" Growth Factors 29(5):187-95.
Chen et al. (1 994) "Substitution of asparagine residues in Aspergillus awamori glucoamylase by site-directed mutagenesis to eliminate N-glycosylation and inactivation by deamidation" Biochem J. 301: 275-81.
Dostalova et al. (2009) "Increased serum concentrations of macrophage inhibitory cytokine-1 in patients with obesity and type 2 diabetes mellitus: the influence of very low calorie diet" Eur. J. Endocrinol. 161:397-404.
Ehses et al. (2007) "Increased Number of Islet-Associated Macrophages in Type 2 Diabetes" Diabetes 56:2356-2370.
Fairlie et al. (2000) "Expression of a TGF-~ superfamily protein macrophage inhibitory cytokine-1 in the yeast *Pichia pastoris*" Gene254:67-76.
Fairlie et al. (2001) "Epitope Mapping of the Transforming Growth Factor-b Superfamily Protein Macrophage Inhibitory Cytokine-1 (MIC-1 ): Identification of at Least Five Distinct Epitope Specificities" Biochem 40:65-73.
Fairlie et al. (2001) "The Propeptide of the Transforming Growth Factor-[beta] Superfamily Member Macrophage Inhibitory Cytokine-1 (MIC-1) Is a Multifunctional Domain That Can Facilitate Protein Folding and Secretion", Priority Journal of Biological Chemistry May 18, 2001 American Society for Biochemistry and Molecular Biology Inc., pp. 16911-16918, vol. 276(20).

(56) References Cited

OTHER PUBLICATIONS

Friedman et al. (1991) "Degradation of growth hormone releasing factor analogs in neutral aqueous solution is related to deamidation of asparagine residues" Int. J. Peptide Protein Res. 37:14-20.
Glee et al. (2007) "The Genetic Landscape of Type 2 Diabetes in Mice" Endocrine Reviews 28(1): 48-83.
Hamann et al. (1996) "Regulation of energy balance by leptin" Exp Endocrinol Diabetes 104:293-200.
Hromas et al. (1997) "PLAB a novel placental bone morphogenetic protein" Biochim.Biophys. Acta 1354:40-4.
Johnen et al. (2007) "Tumor-induced anorexia and weight loss are mediated by the TGF-b superfamily cytokine MIC-1" Nature Medicine 13 (11): 1333-1340.
Lajer et al. (2010) "Plasma growth differentiation factor-15 independently predicts all-cause and cardiovascular mortality as well as deterioration of kidney function in type 1 diabetic patients with nephropathy" Diabetes Care 33(7) 1567-1572.
Lind et al. (2009) "Growth-differentiation factor-15 is an independent marker of cardiovascular dysfunction and lisease in the elderly: results from the Prospective Investigation of the Vasculature in Uppsala Seniors (PIVUS) Study" European Heart Journa/30(19)2346-2353.
Lingvay Ildiko et al. (2016) "Effect of Insulin Glargine Up-titration vs Insulin DegludecLiraglutide on Glycated Hemoglobin Levels in Patients with Uncontrolled Type 2 Diabetes" JAMA, pp. 898-907, vol. 315(9).
Liu Yan et al. (2009) "Enhancing the Secretion of Recombinant Proteins by Engineering N-Giycosylation Sites" Biotechnol. Prog., pp. 1468-1475, vol. 25(5).
Macia et al. (2012) "Macrophage Inhibitory Cytokine 1 (MIC-1 GDF15) Decreases Food Intake Body Weight and Improves Glucose Tolerance in Mice on Normal & Obesogenic Diets" PLoS ONE 7(4):1-8.
Massague (1987) "The TGF-beta Family of Growth and Differentiation Factors" Cell, pp. 437-438, vol. 49.
Ngo et al. (1994) "Computational Complexity Protein Structure Prediction and Levinthal Paradox" The Protein Folding Problem and Tertiary Structure Prediction Birkhauser Boston 492-495.
Oliveira Neto et al. (2008) "Interleukin-22 Forms Dimers that are Recognized by Two Interleukin-22R1 Receptor Chains" Biophysical Journal, pp. 1754-1765, vol. 94.
Paralkar et al. (1998) "Cloning and characterization of a novel member of the transforming growth factor[beta]bone morphogenetic protein family" J. Bioi. Chem 273:13760-13767.
Robinson et al. (2004) "Prediction of primary structure deamidation rates of asparaginyl and glutaminyl peptides trough steric and catalytic effects" J. Pepide Res. 63:437-448.
Shen et al. (2004) "Bone morphogenetic proteins regulate ionotropic glutamate receptors in human retina" Eur. J. Neurosci., pp. 2031-2037, vol. 20.
Soler et al. (2012) "New Experimental Models of Diabetic Nephropathy in Mice Models of Type2 Diabetes: Efforts to Replicate Human Nephropathy" Experimental Diabetes Research vol. 2012Art.ID 616313.
Tokuriki et al. (2009) "Stability effects of mutations and protein evolvability" Curr. Opin.Struc. Bio/.19:596-604.
Vila et al. (2011) "The Relationship between Insulin Resistance and the Cardiovascular 23 Biomarker Growth Differentiation Factor-15 in Obese Patients" Clinical Chemistry 57(2):309-316.
Vukicevic et al. (1996) "Induction of nephrogenic mesenchyme by osteogenic protein 1 (bone morphogenetic protein 7)" PNAS, pp. 9021-9026, vol. 93.
Wells (1 990) "Additivity of Mutational Effects in Proteins" Biochemistry 29(37):8509-8517.
Welsh et al (2003) "Large-scale delineation of secreted protein biomarkers overexpressed in cancer tissue and serum" PNAS, pp. 3410-3415, vol. 1 00(6).
Yokoyama-Kobayashi et al. (1997) "Human eDNA encoding a novel TGF-beta superfamily protein highly expressed in placenta" J. Biochem 122:622-626.

Human GDF15 Precursor Amino Acid Sequence (GenBank Accession No. NP_004855.2; SEQ ID NO:1)

```
  1 mpgqelrtvn gsqmllvllv lswlphggal slaeasrasf pgpselhsed srfrelrkry
 61 edlltrlran qswedsntdl vpapavrilt pevrlgsggh lhlrisraal peglpeasrl
121 hralfrlspt asrswdvtrp lrrqlslarp qapalhlrls pppsqsdqll aessarpql
181 elhlrpqaar grrrararng dhcplgpgrc crlhtvrasl edlgwadwvl sprevqvtmc
241 igacpsqfra anmhaqikts lhrlkpdtvp apccvpasyn pmvliqktdt gvslqtyddl
301 lakdchci
```

Human GDF15 Precursor Nucleic Acid Sequence (GenBank Accession No. BC000529.2; SEQ ID NO:2)

```
    1 agtcccagct cagagccgca acctgcacag ccatgccccg gcaagaactc aggacggtga
   61 atggctctca gatgctcctg gtgttgctgg tgctcctcgt gctgccgcat ggggcgccc
  121 tgtctctggc cgaggcgagc cgcgcaagtt cccgggacc tcagagttg cactccgaag
  181 actccagatt ccgagagttg cggaaacgct acgaggacct gctaaccagg ctgcggggca
  241 accagagctg gaagattcg aacaccgacc tcgtcccggc ccctgcagtc cggatactca
  301 cgccagaagt gcggctggga tccggcggcc acctgcacct gcgtatctct cgggccgcc
  361 ttcccgaggg gctccccga gcctcccgcc ttcaccgggc tctgttccgg ctgtccccga
  421 cggcgtcaag gtcgtgggac gtgacacgac ctgcgactgt cgcgcgccg gtcgcagtcg
  481 cccaggcgcc gaggcggcaa ctgcgctgca cggcccccag cgggagttgca cttgcggccg
  541 tgcagaatc ttcgtccgca cagagccgcg gcgcgaacct tccgcctctg gggctcggg
  601 ggggccgccg cagagccgcg gctgccgtct gcacaccgct ggaagacct tggaagacct
  661 gctgccgtct gcacacggtc ggaggtgcaa gtgaccatgt gcatccggc gtgcccgagc
  721 tgtgccacg ggaggtgcaa gtgaccatgt gcatccggc gtgcccgagc cctgaagccc
  781 cggcaaacat gcacgccag atcaagacga gccagctaca atcccatggt gctcattcaa
  841 cagcgccctg ctgcgtgccc ctgccagacc tatgatgact tgttagccaa agactgccac
  901 ccggggtgtc gctccagacc cttccactg tgcacctgcg cggaggacgc gacctcagtt
  961 cagtcctgt cctccactg ctcaaggttc ctgagacacc cgattcctgc ccaaacagct
 1021 gtgaatggg ctcaaggttc tttattatta atttatggg gtgacctct tgggactcg
 1081 aagtctgtta tgtatttat ttaaactct ggtgataaaa ataaagctgt ctgaactgtt
 1141 tgatggaact gtgtatttat ttaaactct ggtgataaaa ataaagctgt ctgaactgtt
 1201 aaaaaaaaaa aaaaaaaaa
```

FIG. 1A

Mature Human GDF15 Amino Acid Sequence (SEQ ID NO:3)

```
  1                                          10                                         20
Ala Arg Asn Gly Asp His Cys Pro Leu Gly Pro Gly Arg Cys Cys Arg Leu His Thr Val
                                             30                                         40
Arg Ala Ser Leu Glu Asp Leu Gly Trp Ala Asp Trp Val Leu Ser Pro Arg Glu Val Gln
                                             50                                         60
Val Thr Met Cys Ile Gly Ala Cys Pro Ser Gln Phe Arg Ala Ala Asn Met His Ala Gln
                                             70                                         80
Ile Lys Thr Ser Leu His Arg Leu Lys Pro Asp Thr Val Pro Ala Pro Cys Cys Val Pro
                                             90                                        100
Ala Ser Tyr Asn Pro Met Val Leu Ile Gln Lys Thr Asp Thr Gly Val Ser Leu Gln Thr
                                            110
Tyr Asp Asp Leu Leu Ala Lys Asp Cys His Cys Ile
```

Human GDF15 Nucleic Acid Sequence (SEQ ID NO:4)

```
GCGCGTAACGGGGATCACTGTCCGCTCGGGCCGCGGTTGCTGCCGTCTGCACACGGTTCCGCGCGTCCGGAAGACCTGGCTGCGGCTGGGCCGATTGGGT
GCTGTCGCCACGGGAGGTGCAAGTGACCATGTGCATCGGCGTGCCAGTTCCGGGCGCGGCCAAACATGCCAGAGATCAAGACGAGCCTGC
ACCGCCTGAAGCCCGACACGGTGCCCGCGCCTGCTGCCAGCGCTACAATCCCATGGTGCTCATTCAAAAGACCGACACCGGGGTGTCGCTC
CAGACCTATGATGACTTGTTAGCCAAAGACTGCCACTGCATATAA
```

FIG. 1B v1 (SEQ ID NO:5):
AlaArgAsnGlyAsp HisCysProLeuGly ProGlyArgCysCys ArgLeuHisThrVal
ArgAlaSerLeuGlu AspLeuGlyTrpAla AspTrpValLeuSer ProArgGluValGln
ValThrMetCysIle GlyAlaCysProSer GlnPheArgAlaAla AsnMetHisAlaGln
IleLysThrSerLeu HisArgLeuGlnPro AspThrValProAla ProCysCysValPro
AlaSerTyrAsnPro MetValLeuIleGln ArgThrAspThrGly ValSerLeuGlnThr
TyrAspAspLeuLeu AlaArgAspCysHis CysIle v2 (SEQ ID NO:6):
AlaArgAsnGlyAsp HisCysProLeuGly ProGlyArgCysCys ArgLeuHisThrVal
ArgAlaSerLeuGlu AspLeuGlyTrpAla AspTrpValLeuSer ProArgGluValGln
ValThrMetCysIle GlyAlaCysProSer GlnPheArgAlaAla AsnMetHisAlaGln
IleGlnThrSerLeu HisArgLeuLysPro AspThrValProAla ProCysCysValPro
AlaSerTyrAsnPro MetValLeuIleGln ArgThrAspThrGly ValSerLeuGlnThr
TyrAspAspLeuLeu AlaArgAspCysHis CysIle v3 (SEQ ID NO:7):
AlaArgAsnGlyAsp HisCysProLeuGly ProGlyArgCysCys ArgLeuHisThrVal
ArgAlaSerLeuGlu AspLeuGlyTrpAla AspTrpValLeuSer ProArgGluValGln
ValThrMetCysIle GlyAlaCysProSer GlnPheArgAlaAla AsnMetHisAlaGln
IleGlnThrSerLeu HisArgLeuGlnPro AspThrValProAla ProCysCysValPro
AlaSerTyrAsnPro MetValLeuIleGln LysThrAspThrGly ValSerLeuGlnThr
TyrAspAspLeuLeu AlaArgAspCysHis CysIle v4 (SEQ ID NO:8):
AlaArgAsnGlyAsp HisCysProLeuGly ProGlyArgCysCys ArgLeuHisThrVal
ArgAlaSerLeuGlu AspLeuGlyTrpAla AspTrpValLeuSer ProArgGluValGln
ValThrMetCysIle GlyAlaCysProSer GlnPheArgAlaAla AsnMetHisAlaGln
IleGlnThrSerLeu HisArgLeuGlnPro AspThrValProAla ProCysCysValPro
AlaSerTyrAsnPro MetValLeuIleGln ArgThrAspThrGly ValSerLeuGlnThr
TyrAspAspLeuLeu AlaLysAspCysHis CysIle

FIG. 2 v5 (SEQ ID NO:9):
AlaArgAsnGlyAsp HisCysProLeuGly ProGlyArgCysCys ArgLeuHisThrVal
ArgAlaSerLeuGlu AspLeuGlyTrpAla AspTrpValLeuSer ProArgGluValGln
ValThrMetCysIle GlyAlaCysProSer GlnPheArgAlaAla AsnMetHisAlaGln
IleLysThrSerLeu HisArgLeuLysPro AspThrValProAla ProCysCysValPro
AlaSerTyrAsnPro MetValLeuIleGln ArgThrAspThrGly ValSerLeuGlnThr
TyrAspAspLeuLeu AlaArgAspCysHis CysIle v6 (SEQ ID NO:10):
AlaArgAsnGlyAsp HisCysProLeuGly ProGlyArgCysCys ArgLeuHisThrVal
ArgAlaSerLeuGlu AspLeuGlyTrpAla AspTrpValLeuSer ProArgGluValGln
ValThrMetCysIle GlyAlaCysProSer GlnPheArgAlaAla AsnMetHisAlaGln
IleLysThrSerLeu HisArgLeuGlnPro AspThrValProAla ProCysCysValPro
AlaSerTyrAsnPro MetValLeuIleGln LysThrAspThrGly ValSerLeuGlnThr
TyrAspAspLeuLeu AlaArgAspCysHis CysIle v7 (SEQ ID NO:11):
AlaArgAsnGlyAsp HisCysProLeuGly ProGlyArgCysCys ArgLeuHisThrVal
ArgAlaSerLeuGlu AspLeuGlyTrpAla AspTrpValLeuSer ProArgGluValGln
ValThrMetCysIle GlyAlaCysProSer GlnPheArgAlaAla AsnMetHisAlaGln
IleLysThrSerLeu HisArgLeuGlnPro AspThrValProAla ProCysCysValPro
AlaSerTyrAsnPro MetValLeuIleGln ArgThrAspThrGly ValSerLeuGlnThr
TyrAspAspLeuLeu AlaLysAspCysHis CysIle

FIG. 2 (Cont. 1)

v8 (SEQ ID NO:12):
AlaArgAsnGlyAsp HisCysProLeuGly ProGlyArgCysCys ArgLeuGlnSerLeu
ArgAlaSerLeuGlu AspLeuGlyTrpAla AspTrpValLeuSer ProArgGluValGln
ValThrMetCysIle GlyAlaCysProSer GlnPheArgAlaAla AsnMetHisAlaGln
IleGlnThrSerLeu HisArgLeuGlnPro AspThrValProAla ProCysCysValPro
AlaSerTyrAsnPro MetValLeuIleGln ArgThrAspThrGly ValSerLeuGlnThr
TyrAspAspLeuLeu AlaArgAspCysHis CysIle v9 (SEQ ID NO:13):
AlaArgAsnGlyAsp HisCysProLeuGly ProGlyArgCysCys ArgLeuGlnSerLeu
ArgAlaSerLeuGlu AspLeuGlyTrpAla AspTrpValLeuSer ProArgGluValGln
ValThrMetCysIle GlyAlaCysProSer GlnPheArgAlaAla AsnMetHisAlaGln
IleGlnThrSerLeu HisArgLeuLysPro AspThrValProAla ProCysCysValPro
AlaSerTyrAsnPro MetValLeuIleGln ArgThrAspThrGly ValSerLeuGlnThr
TyrAspAspLeuLeu AlaArgAspCysHis CysIle v10 (SEQ ID NO:14):
AlaArgAsnGlyAsp HisCysProLeuGly ProGlyArgCysCys ArgLeuGlnSerLeu
ArgAlaSerLeuGlu AspLeuGlyTrpAla AspTrpValLeuSer ProArgGluValGln
ValThrMetCysIle GlyAlaCysProSer GlnPheArgAlaAla AsnMetHisAlaGln
IleGlnThrSerLeu HisArgLeuGlnPro AspThrValProAla ProCysCysValPro
AlaSerTyrAsnPro MetValLeuIleGln LysThrAspThrGly ValSerLeuGlnThr
TyrAspAspLeuLeu AlaArgAspCysHis CysIle v11 (SEQ ID NO:15):
AlaArgAsnGlyAsp HisCysProLeuGly ProGlyArgCysCys ArgLeuGlnSerLeu
ArgAlaSerLeuGlu AspLeuGlyTrpAla AspTrpValLeuSer ProArgGluValGln
ValThrMetCysIle GlyAlaCysProSer GlnPheArgAlaAla AsnMetHisAlaGln
IleGlnThrSerLeu HisArgLeuGlnPro AspThrValProAla ProCysCysValPro
AlaSerTyrAsnPro MetValLeuIleGln ArgThrAspThrGly ValSerLeuGlnThr
TyrAspAspLeuLeu AlaLysAspCysHis CysIle

FIG. 2 (Cont. 2)

v12 (SEQ ID NO:16):
ProAlaArgAsnGly AspHisCysProLeu GlyProGlyArgCys CysArgLeuHisThr
ValArgAlaSerLeu GluAspLeuGlyTrp AlaAspTrpValLeu SerProArgGluVal
GlnValThrMetCys IleGlyAlaCysPro SerGlnPheArgAla AlaAsnMetHisAla
GlnIleLysThrSer LeuHisArgLeuLys ProAspThrValPro AlaProCysCysVal
ProAlaSerTyrAsn ProMetValLeuIle GlnLysThrAspThr GlyValSerLeuGln
ThrTyrAspAspLeu LeuAlaLysAspCys HisCysIle v13 (SEQ ID NO:17):
ProAlaArgAsnGly AspHisCysProLeu GlyProGlyArgCys CysArgLeuHisThr
ValArgAlaSerLeu GluAspLeuGlyTrp AlaAspTrpValLeu SerProArgGluVal
GlnValThrMetCys IleGlyAlaCysPro SerGlnPheArgAla AlaAsnMetHisAla
GlnIleLysThrSer LeuHisArgLeuGln ProAspThrValPro AlaProCysCysVal
ProAlaSerTyrAsn ProMetValLeuIle GlnArgThrAspThr GlyValSerLeuGln
ThrTyrAspAspLeu LeuAlaArgAspCys HisCysIle v14 (SEQ ID NO:18):
ProAlaArgAsnGly AspHisCysProLeu GlyProGlyArgCys CysArgLeuHisThr
ValArgAlaSerLeu GluAspLeuGlyTrp AlaAspTrpValLeu SerProArgGluVal
GlnValThrMetCys IleGlyAlaCysPro SerGlnPheArgAla AlaAsnMetHisAla
GlnIleGlnThrSer LeuHisArgLeuLys ProAspThrValPro AlaProCysCysVal
ProAlaSerTyrAsn ProMetValLeuIle GlnArgThrAspThr GlyValSerLeuGln
ThrTyrAspAspLeu LeuAlaArgAspCys HisCysIle

FIG. 2 (Cont. 3)

v15 (SEQ ID NO:19):
ProAlaArgAsnGly AspHisCysProLeu GlyProGlyArgCys CysArgLeuHisThr
ValArgAlaSerLeu GluAspLeuGlyTrp AlaAspTrpValLeu SerProArgGluVal
GlnValThrMetCys IleGlyAlaCysPro SerGlnPheArgAla AlaAsnMetHisAla
GlnIleGlnThrSer LeuHisArgLeuGln ProAspThrValPro AlaProCysCysVal
ProAlaSerTyrAsn ProMetValLeuIle GlnLysThrAspThr GlyValSerLeuGln
ThrTyrAspAspLeu LeuAlaArgAspCys HisCysIle v16 (SEQ ID NO:20):
ProAlaArgAsnGly AspHisCysProLeu GlyProGlyArgCys CysArgLeuHisThr
ValArgAlaSerLeu GluAspLeuGlyTrp AlaAspTrpValLeu SerProArgGluVal
GlnValThrMetCys IleGlyAlaCysPro SerGlnPheArgAla AlaAsnMetHisAla
GlnIleGlnThrSer LeuHisArgLeuGln ProAspThrValPro AlaProCysCysVal
ProAlaSerTyrAsn ProMetValLeuIle GlnArgThrAspThr GlyValSerLeuGln
ThrTyrAspAspLeu LeuAlaLysAspCys HisCysIle v17 (SEQ ID NO:21):
ProAlaArgAsnGly AspHisCysProLeu GlyProGlyArgCys CysArgLeuHisThr
ValArgAlaSerLeu GluAspLeuGlyTrp AlaAspTrpValLeu SerProArgGluVal
GlnValThrMetCys IleGlyAlaCysPro SerGlnPheArgAla AlaAsnMetHisAla
GlnIleLysThrSer LeuHisArgLeuLys ProAspThrValPro AlaProCysCysVal
ProAlaSerTyrAsn ProMetValLeuIle GlnArgThrAspThr GlyValSerLeuGln
ThrTyrAspAspLeu LeuAlaArgAspCys HisCysIle v18 (SEQ ID NO:22):
ProAlaArgAsnGly AspHisCysProLeu GlyProGlyArgCys CysArgLeuHisThr
ValArgAlaSerLeu GluAspLeuGlyTrp AlaAspTrpValLeu SerProArgGluVal
GlnValThrMetCys IleGlyAlaCysPro SerGlnPheArgAla AlaAsnMetHisAla
GlnIleLysThrSer LeuHisArgLeuGln ProAspThrValPro AlaProCysCysVal
ProAlaSerTyrAsn ProMetValLeuIle GlnLysThrAspThr GlyValSerLeuGln
ThrTyrAspAspLeu LeuAlaArgAspCys HisCysIle

FIG. 2 (Cont. 4)

v19 (SEQ ID NO:23):
ProAlaArgAsnGly AspHisCysProLeu GlyProGlyArgCys CysArgLeuHisThr
ValArgAlaSerLeu GluAspLeuGlyTrp A v22 (SEQ ID NO:26):

```
ProAlaArgAsnGly AspHisCysProLeu GlyProGlyArgCys CysArgLeuGlnSer
LeuArgAlaSerLeu GluAspLeuGlyTrp AlaAspTrpValLeu SerProArgGluVal
GlnValThrMetCys IleGlyAlaCysPro SerGlnPheArgAla AlaAsnMetHisAla
GlnIleGlnThrSer LeuHisArgLeuGln ProAspThrValPro AlaProCysCysVal
ProAlaSerTyrAsn ProMetValLeuIle GlnLysThrAspThr GlyValSerLeuGln
ThrTyrAspAspLeu LeuAlaArgAspCys HisCysIle
``` v23 (SEQ ID NO:27):

```
ProAlaArgAsnGly AspHisCysProLeu GlyProGlyArgCys CysArgLeuGlnSer
LeuArgAlaSerLeu GluAspLeuGlyTrp AlaAspTrpValLeu SerProArgGluVal
GlnValThrMetCys IleGlyAlaCysPro SerGlnPheArgAla AlaAsnMetHisAla
GlnIleGlnThrSer LeuHisArgLeuGln ProAspThrValPro AlaProCysCysVal
ProAlaSerTyrAsn ProMetValLeuIle GlnArgThrAspThr GlyValSerLeuGln
ThrTyrAspAspLeu LeuAlaLysAspCys HisCysIle
```

FIG. 2 (Cont. 6)

SEQUENCE LISTING

```
<160> NUMBER OF SEQ ID NOS: 47

<210> SEQ ID NO 1
<211> LENGTH: 308
<212> TYPE: PRT
<213> ORGANISM: Homo sapiens

<400> SEQUENCE: 1

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
                20                  25                  30

Ala Glu Ala Ser Arg Ala Ser Phe Pro Gly Pro Ser Glu Leu His Ser
            35                  40                  45

Glu Asp Ser Arg Phe Arg Glu Leu Arg Lys Arg Tyr Glu Asp Leu Leu
        50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
                100                 105                 110

Gly Leu Pro Glu Ala Ser Arg Leu His Arg Ala Leu Phe Arg Leu Ser
            115                 120                 125

Pro Thr Ala Ser Arg Ser Trp Asp Val Thr Arg Pro Leu Arg Arg Gln
        130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
        210                 215                 220
```

```
Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305
```

<210> SEQ ID NO 2
<211> LENGTH: 1220
<212> TYPE: DNA
<213> ORGANISM: Homo sapiens

<400> SEQUENCE: 2

```
agtcccagct cagagccgca acctgcacag ccatgcccgg caagaactc aggacggtga      60
atggctctca gatgctcctg gtgttgctgg tgctctcgtg gctgccgcat ggggcgccc     120
tgtctctggc cgaggcgagc cgcgcaagtt cccggacc ctcagagttg cactccgaag     180
actccagatt ccgagagttg cggaaacgct acgaggacct gctaaccagg ctgcgggcca    240
accagagctg ggaagattcg aacaccgacc tcgtcccggc ccctgcagtc cggatactca    300
cgccagaagt gcggctggga tccggcggcc acctgcacct gcgtatctct cgggccgccc   360
ttcccgaggg gctccccgag gcctcccgcc ttcaccgggc tctgttccgg ctgtccccga    420
cggcgtcaag gtcgtgggac gtgacacgac cgctgcgggcg tcagctcagc cttgcaagac    480
cccaggcgcc cgcgctgcac ctgcgactgt cgccgccgcc gtcgcagtcg gaccaactgc    540
tggcagaatc ttcgtccgca cggccccagc tggagttgca cttgcggccg caagccgcca    600
gggggcgccg cagagcgcgt gcgcgcaacg gggaccactg tccgctcggg cccgggcgtt   660
gctgccgtct gcacacggtc cgcgcgtcgc tggaagacct gggctgggcc gattgggtgc    720
tgtcgccacg ggaggtgcaa gtgaccatgt gcatcggcgc gtgcccgagc cagttccggg    780
cggcaaacat gcacgcgcag atcaagacga gcctgcaccg cctgaagccc gacacggtgc    840
cagcgccctg ctgcgtgccc gccagctaca atcccatggt gctcattcaa aagaccgaca    900
ccggggtgtc gctccagacc tatgatgact tgttagccaa agactgccac tgcatatgag    960
cagtcctggt ccttccactg tgcacctgcg cggaggacgc gacctcagtt gtcctgccct   1020
gtggaatggg ctcaaggttc ctgagacacc cgattcctgc ccaaacagct gtatttatat  1080
aagtctgtta tttattatta atttattggg gtgaccttct tggggactcg ggggctggtc   1140
tgatggaact gtgtatttat ttaaaactct ggtgataaaa ataaagctgt ctgaactgtt   1200
aaaaaaaaaa aaaaaaaaaa                                                1220
```

<210> SEQ ID NO 3
<211> LENGTH: 112
<212> TYPE: PRT
<213> ORGANISM: Homo sapiens

<400> SEQUENCE: 3

```
Ala Arg Asn Gly Asp His Cys Pro Leu Gly Pro Gly Arg Cys Cys Arg
1               5                   10                  15
```

```
Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 4
<211> LENGTH: 339
<212> TYPE: DNA
<213> ORGANISM: Artificial sequence
<220> FEATURE:
<223> OTHER INFORMATION: Synthetic protein sequence

<400> SEQUENCE: 4
gcgcgtaacg gggatcactg tccgctcggg cccgggcgtt gctgccgtct gcacacggtc    60
cgcgcgtcgc tggaagacct gggctgggcc gattgggtgc tgtcgccacg ggaggtgcaa   120
gtgaccatgt gcatcggcgc gtgcccgagc cagttccggg cggcaaacat gcacgcgcag   180
atcaagacga cctgcaccg cctgaagccc gacacggtgc cagcgccctg ctgcgtgccc   240
gccagctaca atcccatggt gctcattcaa aagaccgaca ccggggtgtc gctccagacc   300
tatgatgact gtttagccaa agactgccac tgcatataa                          339

<210> SEQ ID NO 5
<211> LENGTH: 112
<212> TYPE: PRT
<213> ORGANISM: Artificial sequence
<220> FEATURE:
<223> OTHER INFORMATION: Synthetic protein sequence
<220> FEATURE:
<221> NAME/KEY: MISC_FEATURE
<222> LOCATION: (1)..(1)
<223> OTHER INFORMATION: The amino terminus (N-terminus) can either be
      pegylated (covalently attached to one or more molecules of
      polyethylene glycol (PEG), or derivatives thereof) or not
      pegylated.

<400> SEQUENCE: 5

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110
```

<210> SEQ ID NO 6
<211> LENGTH: 112
<212> TYPE: PRT
<213> ORGANISM: Artificial sequence
<220> FEATURE:
<223> OTHER INFORMATION: Synthetic protein sequence

<400> SEQUENCE: 6

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110
```

<210> SEQ ID NO 7
<211> LENGTH: 112
<212> TYPE: PRT
<213> ORGANISM: Artificial sequence
<220> FEATURE:
<223> OTHER INFORMATION: Synthetic protein sequence

<400> SEQUENCE: 7

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Arg Asp Cys His Cys Ile
            100                 105                 110
```

<210> SEQ ID NO 8
<211> LENGTH: 112
<212> TYPE: PRT
<213> ORGANISM: Artificial sequence
<220> FEATURE:
<223> OTHER INFORMATION: Synthetic protein sequence

<400> SEQUENCE: 8

```
Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
```

```
                35                  40                  45

Pro Ser Gln Phe Arg Ala Ala Asn Met His Ala Gln Ile Gln Thr Ser
         50                  55                  60

Leu His Arg Leu Gln Pro Asp Thr Val Pro Ala Pro Cys Cys Val Pro
 65                  70                  75                  80

Ala Ser Tyr Asn Pro Met Val Leu Ile Gln Arg Thr Asp Thr Gly Val
                 85                  90                  95

Ser Leu Gln Thr Tyr Asp Asp Leu Leu Ala Lys Asp Cys His Cys Ile
            100                 105                 110

<210> SEQ ID NO 9
<211> LENGTH: 112
<212> TYPE: PRT
<213> ORGANISM: Artificial sequence
<220> FEATURE:
<223> OTHER INFORMATION: Synthetic protein sequence
<220> FEATURE:
<221> NAME/KEY: MISC_FEATURE
<222> LOCATION: (69)..(69)
<223> OTHER INFORMATION: The lysine at this position can either be
      pegylated (covalently attached to one or more molecules of
      polyethylene glycol (PEG), or derivatives thereof) or not
      pegylated.

<400> SEQUENCE: 9

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
         50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Arg Thr Asp Thr Gly Val
                 85                  90                  95

Ser Leu Gln Thr Tyr Asp Asp Leu Leu Ala Arg Asp Cys His Cys Ile
            100                 105                 110

<210> SEQ ID NO 10
<211> LENGTH: 112
<212> TYPE: PRT
<213> ORGANISM: Artificial sequence
<220> FEATURE:
<223> OTHER INFORMATION: Synthetic protein sequence
<220> FEATURE:
<221> NAME/KEY: MISC_FEATURE
<222> LOCATION: (91)..(91)
<223> OTHER INFORMATION: The lysine at this position can either be
      pegylated (covalently attached to one or more molecules of
      polyethylene glycol (PEG), or derivatives thereof) or not
      pegylated.

<400> SEQUENCE: 10

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
```

```
                    50                  55                  60
Leu His Arg Leu Gln Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Arg Asp Cys His Cys Ile
                100                 105                 110

<210> SEQ ID NO 11
<211> LENGTH: 112
<212> TYPE: PRT
<213> ORGANISM: Artificial sequence
<220> FEATURE:
<223> OTHER INFORMATION: Synthetic protein sequence

<400> SEQUENCE: 11

Ala Arg Asn Gly Asp His Cys Pro Leu Gly Pro Gly Arg Cys Cys Arg
 1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Lys Thr Ser
 50                  55                  60

Leu His Arg Leu Gln Pro Asp Thr Val Pro Ala Pro Cys Cys Val Pro
 65                  70                  75                  80

Ala Ser Tyr Asn Pro Met Val Leu Ile Gln Arg Thr Asp Thr Gly Val
                 85                  90                  95

Ser Leu Gln Thr Tyr Asp Asp Leu Leu Ala Lys Asp Cys His Cys Ile
                100                 105                 110

<210> SEQ ID NO 12
<211> LENGTH: 112
<212> TYPE: PRT
<213> ORGANISM: Artificial sequence
<220> FEATURE:
<223> OTHER INFORMATION: Synthetic protein sequence

<400> SEQUENCE: 12

Ala Arg Asn Gly Asp His Cys Pro Leu Gly Pro Gly Arg Cys Cys Arg
 1               5                  10                  15

Leu Gln Ser Leu Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
             35                  40                  45

Pro Ser Gln Phe Arg Ala Ala Asn Met His Ala Gln Ile Gln Thr Ser
 50                  55                  60

Leu His Arg Leu Gln Pro Asp Thr Val Pro Ala Pro Cys Cys Val Pro
 65                  70                  75                  80

Ala Ser Tyr Asn Pro Met Val Leu Ile Gln Arg Thr Asp Thr Gly Val
                 85                  90                  95

Ser Leu Gln Thr Tyr Asp Asp Leu Leu Ala Arg Asp Cys His Cys Ile
                100                 105                 110

<210> SEQ ID NO 13
<211> LENGTH: 112
<212> TYPE: PRT
<213> ORGANISM: Artificial sequence
<220> FEATURE:
```

<223> OTHER INFORMATION: Synthetic protein sequence

<400> SEQUENCE: 13

```
Ala Arg Asn Gly Asp His Cys Pro Leu Gly Pro Gly Arg Cys Cys Arg
1               5                   10                  15

Leu Gln Ser Leu Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110
```

<210> SEQ ID NO 14
<211> LENGTH: 112
<212> TYPE: PRT
<213> ORGANISM: Artificial sequence
<220> FEATURE:
<223> OTHER INFORMATION: Synthetic protein sequence

<400> SEQUENCE: 14

```
Ala Arg Asn Gly Asp His Cys Pro Leu Gly Pro Gly Arg Cys Cys Arg
1               5                   10                  15

Leu Gln Ser Leu Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Gln Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Arg Asp Cys His Cys Ile
            100                 105                 110
```

<210> SEQ ID NO 15
<211> LENGTH: 112
<212> TYPE: PRT
<213> ORGANISM: Artificial sequence
<220> FEATURE:
<223> OTHER INFORMATION: Synthetic protein sequence

<400> SEQUENCE: 15

```
Ala Arg Asn Gly Asp His Cys Pro Leu Gly Pro Gly Arg Cys Cys Arg
1               5                   10                  15

Leu Gln Ser Leu Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Gln Thr Ser
    50                  55                  60

Leu His Arg Leu Gln Pro Asp Thr Val Pro Ala Pro Cys Cys Val Pro
```

```
                65                  70                  75                  80
Ala Ser Tyr Asn Pro Met Val Leu Ile Gln Arg Thr Asp Thr Gly Val
                    85                  90                  95

Ser Leu Gln Thr Tyr Asp Asp Leu Leu Ala Lys Asp Cys His Cys Ile
                    100                 105                 110
```

<210> SEQ ID NO 16
<211> LENGTH: 113
<212> TYPE: PRT
<213> ORGANISM: Artificial sequence
<220> FEATURE:
<223> OTHER INFORMATION: Synthetic protein sequence

<400> SEQUENCE: 16

```
Pro Ala Arg Asn Gly Asp His Cys Pro Leu Gly Pro Gly Arg Cys Cys
1               5                   10                  15

Arg Leu His Thr Val Arg Ala Ser Leu Glu Asp Leu Gly Trp Ala Asp
                    20                  25                  30

Trp Val Leu Ser Pro Arg Glu Val Gln Val Thr Met Cys Ile Gly Ala
                35                  40                  45

Cys Pro Ser Gln Phe Arg Ala Ala Asn Met His Ala Gln Ile Lys Thr
    50                  55                  60

Ser Leu His Arg Leu Lys Pro Asp Thr Val Pro Ala Pro Cys Cys Val
65                  70                  75                  80

Pro Ala Ser Tyr Asn Pro Met Val Leu Ile Gln Lys Thr Asp Thr Gly
                    85                  90                  95

Val Ser Leu Gln Thr Tyr Asp Asp Leu Leu Ala Lys Asp Cys His Cys
                    100                 105                 110

Ile
```

<210> SEQ ID NO 17
<211> LENGTH: 113
<212> TYPE: PRT
<213> ORGANISM: Artificial sequence
<220> FEATURE:
<223> OTHER INFORMATION: Synthetic protein sequence

<400> SEQUENCE: 17

```
Pro Ala Arg Asn Gly Asp His Cys Pro Leu Gly Pro Gly Arg Cys Cys
1               5                   10                  15

Arg Leu His Thr Val Arg Ala Ser Leu Glu Asp Leu Gly Trp Ala Asp
                    20                  25                  30

Trp Val Leu Ser Pro Arg Glu Val Gln Val Thr Met Cys Ile Gly Ala
                35                  40                  45

Cys Pro Ser Gln Phe Arg Ala Ala Asn Met His Ala Gln Ile Lys Thr
    50                  55                  60

Ser Leu His Arg Leu Gln Pro Asp Thr Val Pro Ala Pro Cys Cys Val
65                  70                  75                  80

Pro Ala Ser Tyr Asn Pro Met Val Leu Ile Gln Arg Thr Asp Thr Gly
                    85                  90                  95

Val Ser Leu Gln Thr Tyr Asp Asp Leu Leu Ala Arg Asp Cys His Cys
                    100                 105                 110

Ile
```

<210> SEQ ID NO 18
<211> LENGTH: 113
<212> TYPE: PRT
<213> ORGANISM: Artificial sequence
<220> FEATURE:
<223> OTHER INFORMATION: Synthetic protein sequence

<400> SEQUENCE: 18

Pro Ala Arg Asn Gly Asp His Cys Pro Leu Gly Pro Gly Arg Cys Cys
1               5                   10                  15

Arg Leu His Thr Val Arg Ala Ser Leu Glu Asp Leu Gly Trp Ala Asp
            20                  25                  30

Trp Val Leu Ser Pro Arg Glu Val Gln Val Thr Met Cys Ile Gly Ala
        35                  40                  45

Cys Pro Ser Gln Phe Arg Ala Ala Asn Met His Ala Gln Ile Gln Thr
    50                  55                  60

Ser Leu His Arg Leu Lys Pro Asp Thr Val Pro Ala Pro Cys Cys Val
65                  70                  75                  80

Pro Ala Ser Tyr Asn Pro Met Val Leu Ile Gln Arg Thr Asp Thr Gly
                85                  90                  95

Val Ser Leu Gln Thr Tyr Asp Asp Leu Leu Ala Arg Asp Cys His Cys
            100                 105                 110

Ile

<210> SEQ ID NO 19
<211> LENGTH: 113
<212> TYPE: PRT
<213> ORGANISM: Artificial sequence
<220> FEATURE:
<223> OTHER INFORMATION: Synthetic protein sequence

<400> SEQUENCE: 19

Pro Ala Arg Asn Gly Asp His Cys Pro Leu Gly Pro Gly Arg Cys Cys
1               5                   10                  15

Arg Leu His Thr Val Arg Ala Ser Leu Glu Asp Leu Gly Trp Ala Asp
            20                  25                  30

Trp Val Leu Ser Pro Arg Glu Val Gln Val Thr Met Cys Ile Gly Ala
        35                  40                  45

Cys Pro Ser Gln Phe Arg Ala Ala Asn Met His Ala Gln Ile Gln Thr
    50                  55                  60

Ser Leu His Arg Leu Gln Pro Asp Thr Val Pro Ala Pro Cys Cys Val
65                  70                  75                  80

Pro Ala Ser Tyr Asn Pro Met Val Leu Ile Gln Lys Thr Asp Thr Gly
                85                  90                  95

Val Ser Leu Gln Thr Tyr Asp Asp Leu Leu Ala Arg Asp Cys His Cys
            100                 105                 110

Ile

<210> SEQ ID NO 20
<211> LENGTH: 113
<212> TYPE: PRT
<213> ORGANISM: Artificial sequence
<220> FEATURE:
<223> OTHER INFORMATION: Synthetic protein sequence

<400> SEQUENCE: 20

Pro Ala Arg Asn Gly Asp His Cys Pro Leu Gly Pro Gly Arg Cys Cys
1               5                   10                  15

Arg Leu His Thr Val Arg Ala Ser Leu Glu Asp Leu Gly Trp Ala Asp
            20                  25                  30

Trp Val Leu Ser Pro Arg Glu Val Gln Val Thr Met Cys Ile Gly Ala
        35                  40                  45

```
Cys Pro Ser Gln Phe Arg Ala Ala Asn Met His Ala Gln Ile Gln Thr
            50                  55                  60

Ser Leu His Arg Leu Gln Pro Asp Thr Val Pro Ala Pro Cys Cys Val
 65                  70                  75                  80

Pro Ala Ser Tyr Asn Pro Met Val Leu Ile Gln Arg Thr Asp Thr Gly
                 85                  90                  95

Val Ser Leu Gln Thr Tyr Asp Asp Leu Leu Ala Lys Asp Cys His Cys
            100                 105                 110

Ile
```

<210> SEQ ID NO 21
<211> LENGTH: 113
<212> TYPE: PRT
<213> ORGANISM: Artificial Sequence
<220> FEATURE:
<223> OTHER INFORMATION: Synthetic protein sequence

<400> SEQUENCE: 21

```
Pro Ala Arg Asn Gly Asp His Cys Pro Leu Gly Pro Gly Arg Cys Cys
 1               5                  10                  15

Arg Leu His Thr Val Arg Ala Ser Leu Glu Asp Leu Gly Trp Ala Asp
                20                  25                  30

Trp Val Leu Ser Pro Arg Glu Val Gln Val Thr Met Cys Ile Gly Ala
                35                  40                  45

Cys Pro Ser Gln Phe Arg Ala Ala Asn Met His Ala Gln Ile Lys Thr
            50                  55                  60

Ser Leu His Arg Leu Lys Pro Asp Thr Val Pro Ala Pro Cys Cys Val
 65                  70                  75                  80

Pro Ala Ser Tyr Asn Pro Met Val Leu Ile Gln Arg Thr Asp Thr Gly
                 85                  90                  95

Val Ser Leu Gln Thr Tyr Asp Asp Leu Leu Ala Arg Asp Cys His Cys
            100                 105                 110

Ile
```

<210> SEQ ID NO 22
<211> LENGTH: 113
<212> TYPE: PRT
<213> ORGANISM: Artificial Sequence
<220> FEATURE:
<223> OTHER INFORMATION: Synthetic protein sequence

<400> SEQUENCE: 22

```
Pro Ala Arg Asn Gly Asp His Cys Pro Leu Gly Pro Gly Arg Cys Cys
 1               5                  10                  15

Arg Leu His Thr Val Arg Ala Ser Leu Glu Asp Leu Gly Trp Ala Asp
                20                  25                  30

Trp Val Leu Ser Pro Arg Glu Val Gln Val Thr Met Cys Ile Gly Ala
                35                  40                  45

Cys Pro Ser Gln Phe Arg Ala Ala Asn Met His Ala Gln Ile Lys Thr
            50                  55                  60

Ser Leu His Arg Leu Gln Pro Asp Thr Val Pro Ala Pro Cys Cys Val
 65                  70                  75                  80

Pro Ala Ser Tyr Asn Pro Met Val Leu Ile Gln Lys Thr Asp Thr Gly
                 85                  90                  95

Val Ser Leu Gln Thr Tyr Asp Asp Leu Leu Ala Arg Asp Cys His Cys
            100                 105                 110
```

Ile

<210> SEQ ID NO 23
<211> LENGTH: 113
<212> TYPE: PRT
<213> ORGANISM: Artificial Sequence
<220> FEATURE:
<223> OTHER INFORMATION: Synthetic protein sequence

<400> SEQUENCE: 23

```
Pro Ala Arg Asn Gly Asp His Cys Pro Leu Gly Pro Gly Arg Cys Cys
1               5                   10                  15

Arg Leu His Thr Val Arg Ala Ser Leu Glu Asp Leu Gly Trp Ala Asp
            20                  25                  30

Trp Val Leu Ser Pro Arg Glu Val Gln Val Thr Met Cys Ile Gly Ala
        35                  40                  45

Cys Pro Ser Gln Phe Arg Ala Ala Asn Met His Ala Gln Ile Lys Thr
    50                  55                  60

Ser Leu His Arg Leu Gln Pro Asp Thr Val Pro Ala Pro Cys Cys Val
65                  70                  75                  80

Pro Ala Ser Tyr Asn Pro Met Val Leu Ile Gln Arg Thr Asp Thr Gly
                85                  90                  95

Val Ser Leu Gln Thr Tyr Asp Asp Leu Leu Ala Lys Asp Cys His Cys
            100                 105                 110
```

Ile

<210> SEQ ID NO 24
<211> LENGTH: 113
<212> TYPE: PRT
<213> ORGANISM: Artificial Sequence
<220> FEATURE:
<223> OTHER INFORMATION: Synthetic protein sequence

<400> SEQUENCE: 24

```
Pro Ala Arg Asn Gly Asp His Cys Pro Leu Gly Pro Gly Arg Cys Cys
1               5                   10                  15

Arg Leu Gln Ser Leu Arg Ala Ser Leu Glu Asp Leu Gly Trp Ala Asp
            20                  25                  30

Trp Val Leu Ser Pro Arg Glu Val Gln Val Thr Met Cys Ile Gly Ala
        35                  40                  45

Cys Pro Ser Gln Phe Arg Ala Ala Asn Met His Ala Gln Ile Gln Thr
    50                  55                  60

Ser Leu His Arg Leu Gln Pro Asp Thr Val Pro Ala Pro Cys Cys Val
65                  70                  75                  80

Pro Ala Ser Tyr Asn Pro Met Val Leu Ile Gln Arg Thr Asp Thr Gly
                85                  90                  95

Val Ser Leu Gln Thr Tyr Asp Asp Leu Leu Ala Arg Asp Cys His Cys
            100                 105                 110
```

Ile

<210> SEQ ID NO 25
<211> LENGTH: 113
<212> TYPE: PRT
<213> ORGANISM: Artificial Sequence
<220> FEATURE:
<223> OTHER INFORMATION: Synthetic protein sequence

<400> SEQUENCE: 25

```
Pro Ala Arg Asn Gly Asp His Cys Pro Leu Gly Pro Gly Arg Cys Cys
```

```
1               5                   10                  15
Arg Leu Gln Ser Leu Arg Ala Ser Leu Glu Asp Leu Gly Trp Ala Asp
            20                  25                  30

Trp Val Leu Ser Pro Arg Glu Val Gln Val Thr Met Cys Ile Gly Ala
            35                  40                  45

Cys Pro Ser Gln Phe Arg Ala Ala Asn Met His Ala Gln Ile Gln Thr
        50                  55                  60

Ser Leu His Arg Leu Lys Pro Asp Thr Val Pro Ala Pro Cys Cys Val
65                  70                  75                  80

Pro Ala Ser Tyr Asn Pro Met Val Leu Ile Gln Arg Thr Asp Thr Gly
                85                  90                  95

Val Ser Leu Gln Thr Tyr Asp Asp Leu Leu Ala Arg Asp Cys His Cys
            100                 105                 110

Ile
```

<210> SEQ ID NO 26
<211> LENGTH: 113
<212> TYPE: PRT
<213> ORGANISM: Artificial Sequence
<220> FEATURE:
<223> OTHER INFORMATION: Synthetic protein sequence

<400> SEQUENCE: 26

```
Pro Ala Arg Asn Gly Asp His Cys Pro Leu Gly Pro Gly Arg Cys Cys
1               5                   10                  15

Arg Leu Gln Ser Leu Arg Ala Ser Leu Glu Asp Leu Gly Trp Ala Asp
            20                  25                  30

Trp Val Leu Ser Pro Arg Glu Val Gln Val Thr Met Cys Ile Gly Ala
            35                  40                  45

Cys Pro Ser Gln Phe Arg Ala Ala Asn Met His Ala Gln Ile Gln Thr
        50                  55                  60

Ser Leu His Arg Leu Gln Pro Asp Thr Val Pro Ala Pro Cys Cys Val
65                  70                  75                  80

Pro Ala Ser Tyr Asn Pro Met Val Leu Ile Gln Lys Thr Asp Thr Gly
                85                  90                  95

Val Ser Leu Gln Thr Tyr Asp Asp Leu Leu Ala Arg Asp Cys His Cys
            100                 105                 110

Ile
```

<210> SEQ ID NO 27
<211> LENGTH: 113
<212> TYPE: PRT
<213> ORGANISM: Artificial Sequence
<220> FEATURE:
<223> OTHER INFORMATION: Synthetic protein sequence

<400> SEQUENCE: 27

```
Pro Ala Arg Asn Gly Asp His Cys Pro Leu Gly Pro Gly Arg Cys Cys
1               5                   10                  15

Arg Leu Gln Ser Leu Arg Ala Ser Leu Glu Asp Leu Gly Trp Ala Asp
            20                  25                  30

Trp Val Leu Ser Pro Arg Glu Val Gln Val Thr Met Cys Ile Gly Ala
            35                  40                  45

Cys Pro Ser Gln Phe Arg Ala Ala Asn Met His Ala Gln Ile Gln Thr
        50                  55                  60

Ser Leu His Arg Leu Gln Pro Asp Thr Val Pro Ala Pro Cys Cys Val
65                  70                  75                  80
```

```
Pro Ala Ser Tyr Asn Pro Met Val Leu Ile Gln Arg Thr Asp Thr Gly
                85                  90                  95

Val Ser Leu Gln Thr Tyr Asp Asp Leu Leu Ala Lys Asp Cys His Cys
            100                 105                 110

Ile
```

<210> SEQ ID NO 28
<211> LENGTH: 11
<212> TYPE: PRT
<213> ORGANISM: Artificial Sequence
<220> FEATURE:
<223> OTHER INFORMATION: Synthetic protein sequence

<400> SEQUENCE: 28

```
Tyr Gly Arg Lys Lys Arg Arg Gln Arg Arg Arg
1               5                   10
```

<210> SEQ ID NO 29
<211> LENGTH: 12
<212> TYPE: PRT
<213> ORGANISM: Artificial Sequence
<220> FEATURE:
<223> OTHER INFORMATION: Synthetic protein sequence

<400> SEQUENCE: 29

```
Arg Arg Gln Arg Arg Thr Ser Lys Leu Met Lys Arg
1               5                   10
```

<210> SEQ ID NO 30
<211> LENGTH: 27
<212> TYPE: PRT
<213> ORGANISM: Artificial Sequence
<220> FEATURE:
<223> OTHER INFORMATION: Synthetic protein sequence

<400> SEQUENCE: 30

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 31
<211> LENGTH: 33
<212> TYPE: PRT
<213> ORGANISM: Artificial Sequence
<220> FEATURE:
<223> OTHER INFORMATION: Synthetic protein sequence

<400> SEQUENCE: 31

```
Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala
```

<210> SEQ ID NO 32
<211> LENGTH: 16
<212> TYPE: PRT
<213> ORGANISM: Artificial Sequence
<220> FEATURE:
<223> OTHER INFORMATION: Synthetic protein sequence

<400> SEQUENCE: 32

Arg Gln Ile Lys Ile Trp Phe Gln Asn Arg Arg Met Lys Trp Lys Lys
1               5                   10                  15

<210> SEQ ID NO 33
<211> LENGTH: 9
<212> TYPE: PRT
<213> ORGANISM: Artificial Sequence
<220> FEATURE:
<223> OTHER INFORMATION: Synthetic protein sequence

<400> SEQUENCE: 33

Arg Lys Lys Arg Arg Gln Arg Arg Arg
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic protein sequence

<400> SEQUENCE: 34

Arg Lys Lys Arg Arg Gln Arg Arg
1               5

<210> SEQ ID NO 35
<211> LENGTH: 11
<212> TYPE: PRT
<213> ORGANISM: Artificial Sequence
<220> FEATURE:
<223> OTHER INFORMATION: Synthetic protein sequence

<400> SEQUENCE: 35

Tyr Ala Arg Ala Ala Ala Arg Gln Ala Arg Ala
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Synthetic protein sequence

<400> SEQUENCE: 36

Thr His Arg Leu Pro Arg Arg Arg Arg Arg Arg
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Synthetic protein sequence

<400> SEQUENCE: 37

Gly Gly Arg Arg Ala Arg Arg Arg Arg Arg Arg
1               5                   10

<210> SEQ ID NO 38
<211> LENGTH: 22
<212> TYPE: DNA
<213> ORGANISM: Artificial Sequence
<220> FEATURE:
<223> OTHER INFORMATION: Synthetic protein sequence

<400> SEQUENCE: 38
tgctctagaa tgcccgggca ag                                             22

<210> SEQ ID NO 39
<211> LENGTH: 26
<212> TYPE: DNA
<213> ORGANISM: Artificial Sequence
<220> FEATURE:
<223> OTHER INFORMATION: Synthetic protein sequence

<400> SEQUENCE: 39
ccatcgatct atcatatgca gtggca                                      26

<210> SEQ ID NO 40
<211> LENGTH: 5
<212> TYPE: PRT
<213> ORGANISM: Artificial Sequence
<220> FEATURE:
<223> OTHER INFORMATION: Synthetic protein sequence

<400> SEQUENCE: 40

Gly Ser Gly Gly Ser
1               5

<210> SEQ ID NO 41
<211> LENGTH: 4
<212> TYPE: PRT
<213> ORGANISM: Artificial Sequence
<220> FEATURE:
<223> OTHER INFORMATION: Synthetic protein sequence

<400> SEQUENCE: 41

Gly Gly Gly Ser
1

<210> SEQ ID NO 42
<211> LENGTH: 4
<212> TYPE: PRT
<213> ORGANISM: Artificial Sequence
<220> FEATURE:
<223> OTHER INFORMATION: Synthetic protein sequence

<400> SEQUENCE: 42

Gly Gly Ser Gly
1

<210> SEQ ID NO 43
<211> LENGTH: 5
<212> TYPE: PRT
<213> ORGANISM: Artificial Sequence
<220> FEATURE:
<223> OTHER INFORMATION: Synthetic protein sequence

<400> SEQUENCE: 43

Gly Gly Ser Gly Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic protein sequence

<400> SEQUENCE: 44

Gly Ser Gly Ser Gly
1               5

```
<210> SEQ ID NO 45
<211> LENGTH: 5
<212> TYPE: PRT
<213> ORGANISM: Artificial Sequence
<220> FEATURE:
<223> OTHER INFORMATION: Synthetic protein sequence

<400> SEQUENCE: 45

Gly Ser Gly Gly Gly
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic protein sequence

<400> SEQUENCE: 46

Gly Gly Gly Ser Gly
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic protein sequence

<400> SEQUENCE: 47

Gly Ser Ser Ser Gly
1               5
```

COMPOSITIONS AND METHODS OF USE FOR TREATING METABOLIC DISORDERS

CROSS-REFERENCE

This application claims the benefit of U.S. patent application Ser. No. 15/377,679, filed on Dec. 13, 2016, issued as U.S. Pat. No. 10,195,250 on Feb. 5, 2019, which application claims the benefit of U.S. patent application Ser. No. 14/373,617, filed on Jul. 21, 2014, issued as U.S. Pat. No. 9,550,819 on Jan. 24, 2017, which application claims the benefit of International Application No. PCT/US2013/029955, filed on Mar. 8, 2013, which application claims the benefit of U.S. Provisional Patent Application No. 61/616,294, filed Mar. 27, 2012, which application is incorporated herein by reference in its entirety.

FIELD OF THE INVENTION

The present invention relates to, among other things, growth differentiation factor muteins and modifications thereof which are useful in treating obesity, diabetes and other metabolic-related disorders.

BACKGROUND

Obesity is most commonly caused by excessive food intake coupled with limited energy expenditure and/or lack of physical exercise. Obesity increases the likelihood of development of various diseases, such as diabetes mellitus, hypertension, atherosclerosis, coronary artery disease, sleep apnea, gout, rheumatism and arthritis. Moreover, mortality risk directly correlates with obesity, such that, for example, a body-mass index in excess of 40 results in an average decreased life expectancy of more than 10 years.

Current pharmacological treatment modalities include appetite suppressors targeting receptor classes (e.g., CB1, 5-$HT_{2C}$, and NPY); regulators of the appetite circuits in the hypothalamus and the molecular actions of ghrelin; and nutrient-absorption inhibitors targeting lipases. Unfortunately, none of the current modalities has been shown to effectively treat obesity without causing adverse effects, some of which can be very severe.

High blood glucose levels stimulate the secretion of insulin by pancreatic beta-cells. Insulin in turn stimulates the entry of glucose into muscles and adipose cells, leading to the storage of glycogen and triglycerides and to the synthesis of proteins. Activation of insulin receptors on various cell types diminishes circulating glucose levels by increasing glucose uptake and utilization, and by reducing hepatic glucose output. Disruptions within this regulatory network can result in diabetes and associated pathologic syndromes that affect a large and growing percentage of the human population.

Patients who have a glucose metabolism disorder can suffer from hyperglycemia, hyperinsulinemia, and/or glucose intolerance. An example of a disorder that is often associated with the aberrant levels of glucose and/or insulin is insulin resistance, in which liver, fat, and muscle cells lose their ability to respond to normal blood insulin levels.

In view of the prevalence and severity of obesity, diabetes and associated metabolic and non-metabolic disorders, along with the shortcomings of current treatment options, alternative treatment modalities that modulate, for example, appetite, glucose and/or insulin levels and enhance the biological response to fluctuating glucose levels in a patient remain of interest.

SUMMARY

The present disclosure contemplates the use of the agents described herein, and compositions thereof, to treat and/or prevent various diseases, disorders and conditions, and/or the symptoms thereof. In some embodiments, the diseases, disorders and conditions, and/or the symptoms thereof, relate to glucose metabolism disorders and other metabolic-related disorders, whereas in other embodiments they relate to body weight disorders. By way of example, but not limitation, the agents, and compositions thereof, can be used for the treatment and/or prevention of diabetes mellitus (e.g., Type 2 diabetes), insulin resistance and diseases, disorders and conditions characterized by insulin resistance, decreased insulin production, hyperglycemia, hypoinsulinemia, and metabolic syndrome. The agents, and compositions thereof, can also be used for the treatment and/or prevention of obesity and other body weight disorders by, for example, effecting appetite suppression.

In certain embodiments, the agents are human Growth Differentiation Factor 15 (GDF15)-related polypeptides, and homologs, variants (e.g., muteins), fragments and other modified forms thereof. In particular embodiments, the agents contemplated by the present disclosure are modified human GDF15 molecules, whereas in other embodiments the agents are GDF15 muteins or modified GDF15 muteins. The present disclosure also contemplates nucleic acid molecules encoding the foregoing. For the sake of convenience, the modified human GDF15 molecules, the GDF15 variants (e.g., muteins), and the modified GDF15 variants (e.g., muteins) described henceforward are collectively referred to hereafter as the "Polypeptide(s)". It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it may correspond to a sequence of a naturally occurring human polypeptide or nucleic acid molecule. In addition to the human polypeptides and the nucleic acid molecules which encode them, the present disclosure contemplates GDF15-related polypeptides and corresponding nucleic acid molecules from other species.

The present disclosure also contemplates other GDF15-related agents capable of eliciting a biological response comparable to (or greater than) that of the Polypeptides, and/or agents capable of enhancing the activity of the Polypeptides.

In some embodiments of the present disclosure, a subject having, or at risk of having, a disease or disorder treatable by one or more Polypeptides is administered in an amount effective for treating the disease or disorder. In some embodiments, the disease or disorder is a hyperglycemic condition, insulin resistance, hyperinsulinemia, glucose intolerance or metabolic syndrome. In other embodiments the disease or disorder is a body weight disorder (e.g., obesity), while in still other embodiments the Polypeptides cause, to at least some extent, appetite suppression.

Other aspects of the present disclosure include cell-based expression systems, vectors, engineered cell lines, and methods and uses related to the foregoing.

As described in detail hereafter, one embodiment of the present disclosure relates to a peptide comprising any one of: a) a peptide comprising at least one modification to the sequence depicted in FIG. 1B (SEQ ID NO:3); b) a mutein peptide of the sequence depicted in FIG. 1B (SEQ ID NO:3);

or c) a mutein peptide of the sequence depicted in FIG. 1B (SEQ ID NO:3), wherein the mutein peptide comprises at least one modification.

In certain embodiments of the present disclosure, a peptide comprises a mutein peptide of any one of v1-v23 as depicted in FIG. 2.

In other embodiments, the modification to a peptide comprises pegylation, glycosylation, polysialylation, hesylation, albumin fusion, albumin binding through a conjugated fatty acid chain, Fc-fusion, or fusion with a PEG mimetic. In particular embodiments, the modification comprises pegylation.

In still further embodiments, a peptide of the present disclosure comprises an amino acid sequence having at least 85% amino acid identity, at least 90% amino acid identity, at least 93% amino acid identity, at least 95% amino acid identity, at least 97% amino acid identity, at least 98% amino acid identity, or at least 99% amino acid identity to the amino acid sequence depicted in FIG. 1B (SEQ ID NO:3)

A peptide of the present disclosure may have fewer than 100 amino acid residues, fewer than 75 amino acid residues, fewer than 50 amino acid residues, fewer than 25 amino acid residues, or fewer than 20 amino acid residues.

According to the present disclosure, the peptide may be produced recombinantly.

Furthermore, the present disclosure contemplates nucleic acid molecules encoding the aforementioned peptides. In some embodiments, a nucleic acid molecule is operably linked to an expression control element that confers expression of the nucleic acid molecule encoding the peptide in vitro, in a cell or in vivo. In some embodiments, a vector (e.g., a viral vector) contains one or more of the nucleic acid molecules.

Some embodiments include transformed or host cells that express one or more of the aforementioned peptides.

In particular embodiments of the present disclosure, one or more of the aforementioned peptides is formulated to yield a pharmaceutical composition, wherein the composition also includes one or more pharmaceutically acceptable diluents, carriers or excipients. In certain embodiments, a pharmaceutical composition also includes at least one additional prophylactic or therapeutic agent.

Still further embodiments of the present disclosure comprise an antibody that binds specifically to one of the aforementioned mutein peptides. In some embodiments, the antibody comprises a light chain variable region and a heavy chain variable region present in separate polypeptides or in a single polypeptide. An antibody of the present disclosure binds the peptide with an affinity of from about $10^7$ $M^{-1}$ to about $10^{12}$ $M^{-1}$ in certain embodiments. In still other embodiments, the antibody comprises a heavy chain constant region of the isotype IgG1, IgG2, IgG3, or IgG4. In additional embodiments, the antibody is detectably labeled, while it is a Fv, scFv, Fab, F(ab')$_2$, or Fab' in other embodiments.

The present disclosure also contemplates antibodies that comprise a covalently linked non-peptide polymer (e.g., a poly(ethylene glycol) polymer). In other embodiments, the antibody comprises a covalently linked moiety selected from a lipid moiety, a fatty acid moiety, a polysaccharide moiety, and a carbohydrate moiety.

The antibody is a single chain Fv (scFv) antibody in some embodiments, and the scFv is multimerized in others.

The antibodies of the present disclosure may be, but are not limited to, monoclonal antibodies, polyclonal antibodies, or humanized antibodies.

Furthermore, the present disclosure contemplates pharmaceutical compositions comprising an antibody as described above formulated with at least one pharmaceutically acceptable excipient, carrier or diluent. Such pharmaceutical compositions may also contain at least one additional prophylactic or therapeutic agent.

Certain embodiments of the present disclosure contemplate a sterile container that contains one of the above-mentioned pharmaceutical compositions and optionally one or more additional components. By way of example, but not limitation, the sterile container may be a syringe. In still further embodiments, the sterile container is one component of a kit; the kit may also contain, for example, a second sterile container that contains at least one prophylactic or therapeutic agent.

The present disclosure also contemplates a method of treating or preventing a glucose metabolism disorder in a subject (e.g., a human) by administering to the subject a therapeutically effective amount of a Polypeptide. In some methods, the treating or preventing results in a reduction in plasma glucose in the subject, a reduction in plasma insulin in the subject, or an increase in glucose tolerance in the subject. In particular embodiments, the glucose metabolism disorder is diabetes mellitus. In some embodiments, the subject is obese and/or has a body weight disorder.

Though not limited to any particular route of administration or dosing regimen, in some embodiments the administering is by parenteral (e.g., subcutaneous) injection.

BRIEF DESCRIPTION OF THE DRAWINGS

FIG. 1A depicts the human GDF15 precursor amino acid sequence (SEQ ID NO:1) and the corresponding nucleic acid (SEQ ID NO:2) encoding the human GDF15 precursor amino acid sequence.

FIG. 1B depicts the mature human GDF15 amino acid sequence (SEQ ID NO:3) and the corresponding nucleic acid sequence (SEQ ID NO:4) encoding mature human GDF15.

FIG. 2 depicts the amino acid sequences of GDF15 muteins v1-v23. v1 (SEQ ID NO:5); v2 (SEQ ID NO:6); v3 (SEQ ID NO:7); v4 (SEQ ID NO:8); v5 (SEQ ID NO:9); v6 (SEQ ID NO:10); v7 (SEQ ID NO:11); v8 (SEQ ID NO:12); v9 (SEQ ID NO:13); v10 (SEQ ID NO:14); v11 (SEQ ID NO:15); v12 (SEQ ID NO:16); v13 (SEQ ID NO:17); v14 (SEQ ID NO:18); v15 (SEQ ID NO:19); v16 (SEQ ID NO:20); v17 (SEQ ID NO:21); v18 (SEQ ID NO:22); v19 (SEQ ID NO:23); v20 (SEQ ID NO:24); v21 (SEQ ID NO:25); v22 (SEQ ID NO:26); v23 (SEQ ID NO:27).

DETAILED DESCRIPTION

Figure 3:
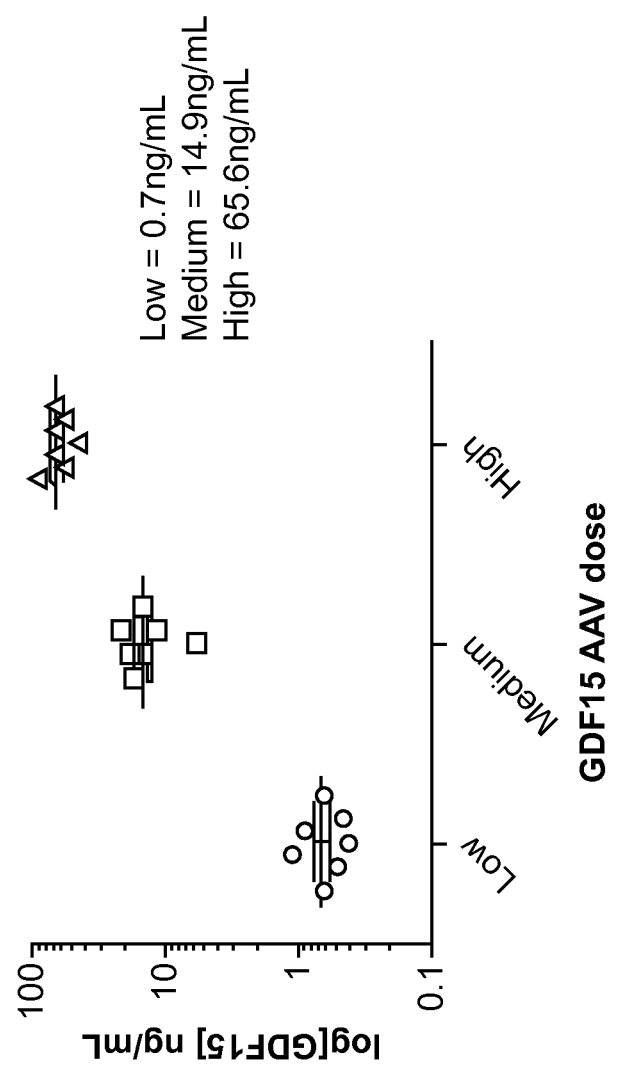
FIG. 3 depicts the level of systemic serum exposure of GDF15 in DIO mice (n=7) two weeks following genetic exposure via AAV. As noted in the figure, for Low AAV the dose=0.7 ng/mL (circles), for Medium AAV the dose=14.9 ng/mL (squares), and for High AAV the dose=65.5 ng/mL (triangles). The horizontal line associated with each dose indicates the average.

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. Thus, for example, reference to "the Human Polypeptide" includes reference to one or more Human Polypeptides; reference to "the Polypeptide" includes reference to one or more Polypeptides; and so forth. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Overview

The present disclosure contemplates the use of the agents described herein, and compositions thereof, to treat and/or prevent various diseases, disorders and conditions, and/or the symptoms thereof. In some embodiments, the diseases, disorders and conditions, and/or the symptoms thereof, pertain to glucose metabolism disorders, while in other embodiments they pertain to body weight disorders. By way of example, but not limitation, the agents, and compositions thereof, can be used for the treatment and/or prevention of Type 2 diabetes, insulin resistance and diseases, disorders and conditions characterized by insulin resistance, decreased insulin production, hyperglycemia, metabolic syndrome, or obesity.

In particular embodiments, the agents contemplated by the present disclosure are modified human Growth Differentiation Factor 15 (GDF15) molecules, whereas in other embodiments the agents are GDF15 variants (e.g., muteins) or modified GDF15 variants. The modified human GDF15 molecules, GDF15 variants (e.g., muteins) and modified GDF15 variants have sufficient homology to human GDF15 such that they have the ability to bind the GDF15 receptor(s) and initiate a signal transduction pathway resulting in, for example, reduced body weight and/or the other physiological effects described herein. The present disclosure also contemplates nucleic acid molecules encoding the foregoing. As indicated above, the modified human GDF15 molecules, the GDF15 variants (e.g., muteins), and the modified GDF15 variants described henceforward are collectively referred to as the "Polypeptide(s)".

Examples of various GDF15 muteins are described hereafter. In some embodiments, one or more GDF15 residues are substituted with another amino acid. In other embodiments, one or more GDF15 native lysine residues are substituted with another amino acid. However, as set forth below, K62Q modifications are inactive. Examples of modified GDF15 molecules and modified GDF15 muteins are described hereafter.

The present disclosure contemplates modifications to GDF15 and GDF15 muteins, including, for example, pegylation and glycosylation. In particular embodiments, strategies are employed such that pegylation is effected only at specific lysine residues (i.e., site-specific pegylation). The modifications may, for example, improve the serum half-life of the Polypeptides. Examples of particular modified GDF15 molecules and modified GDF15 muteins are described hereafter.

Definitions

The terms "patient" or "subject" are used interchangeably to refer to a human or a non-human animal (e.g., a mammal).

The terms 'treat", "treating", treatment" and the like refer to a course of action (such as administering a Polypeptide or a pharmaceutical composition comprising a Polypeptide) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (i.e., arresting the development or further development of the disease, disorder or condition or clinical symptoms association therewith) an active disease (e.g., so as to decrease the level of insulin and/or glucose in the bloodstream, to increase glucose tolerance so as to minimize fluctuation of glucose levels, and/or so as to protect against diseases caused by disruption of glucose homeostasis).

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering a Polypeptide or a pharmaceutical composition comprising a Polypeptide) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects. For example, in the case of a hyperglycemic condition, a lowering or reduction of blood glucose or an improvement in glucose tolerance test can be used to determine whether the amount of an agent is effective to treat the hyperglycemic condition. For example, a therapeutically effective amount is an amount sufficient to reduce or decrease any level (e.g., a baseline level) of fasting plasma glucose (FPG), wherein, for example, the amount is sufficient to reduce a FPG level greater than 200 mg/dl to less than 200 mg/dl, wherein the amount is sufficient to reduce a FPG level between 175 mg/dl and 200 mg/dl to less than the starting level, wherein the amount is sufficient to reduce a FPG level between 150 mg/dl and 175 mg/dl to less than the starting level, wherein the amount is sufficient to reduce a FPG level between 125 mg/dl and 150 mg/dl to less than the starting level, and so on (e.g., reducing FPG levels to less than 125 mg/dl, to less than 120 mg/dl, to less than 115 mg/dl, to less than 110 mg/dl, etc.). In the case of HbAIc levels, the effective amount is an amount sufficient to reduce or decrease levels by more than about 10% to 9%, by more than about 9% to 8%, by more than about 8% to 7%, by more than about 7% to 6%, by more than about 6% to 5%, and so on. More particularly, a reduction or decrease of HbAIc levels by about 0.1%, 0.25%, 0.4%, 0.5%, 0.6%, 0.7%, 0.8%, 0.9%, 1%, 1.5%, 2%, 3%, 4%, 5%, 10%, 20%, 30%, 33%, 35%, 40%, 45%, 50%, or more is contemplated by the present disclosure. The therapeutically effective amount can be adjusted in connection with the dosing regimen and diagnostic analysis of the subject's condition and the like.

The phrase "in a sufficient amount to effect a change" means that there is a detectable difference between a level of an indicator measured before (e.g., a baseline level) and after administration of a particular therapy. Indicators include any objective parameter (e.g., level of glucose or insulin) or subjective parameter (e.g., subject's feeling of well-being).

The phrase "glucose tolerance", as used herein, refers to the ability of a subject to control the level of plasma glucose and/or plasma insulin when glucose intake fluctuates. For example, glucose tolerance encompasses the subject's ability to reduce, within about 120 minutes, the level of plasma glucose back to a level determined before the intake of glucose.

Broadly speaking, the terms "diabetes" and "diabetic" refer to a progressive disease of carbohydrate metabolism involving inadequate production or utilization of insulin, frequently characterized by hyperglycemia and glycosuria. The terms "pre-diabetes" and "pre-diabetic" refer to a state wherein a subject does not have the characteristics, symptoms and the like typically observed in diabetes, but does have characteristics, symptoms and the like that, if left untreated, may progress to diabetes. The presence of these conditions may be determined using, for example, either the fasting plasma glucose (FPG) test or the oral glucose tolerance test (OGTT). Both require a subject to fast for at least 8 hours prior to initiating the test. In the FPG test, a subject's blood glucose is measured after the conclusion of the fasting; generally, the subject fasts overnight and the blood glucose is measured in the morning before the subject eats. A healthy subject would generally have a FPG concentration between about 90 and about 100 mg/dl, a subject with "pre-diabetes" would generally have a FPG concentration between about 100 and about 125 mg/dl, and a subject with "diabetes" would generally have a FPG level above about 126 mg/dl. In the OGTT, a subject's blood glucose is measured after fasting and again two hours after drinking a glucose-rich beverage. Two hours after consumption of the glucose-rich beverage, a healthy subject generally has a blood glucose concentration below about 140 mg/dl, a pre-diabetic subject generally has a blood glucose concentration about 140 to about 199 mg/dl, and a diabetic subject generally has a blood glucose concentration about 200 mg/dl or above. While the aforementioned glycemic values pertain to human subjects, normoglycemia, moderate hyperglycemia and overt hyperglycemia are scaled differently in murine subjects. A healthy murine subject after a four-hour fast would generally have a FPG concentration between about 100 and about 150 mg/dl, a murine subject with "pre-diabetes" would generally have a FPG concentration between about 175 and about 250 mg/dl and a murine subject with "diabetes" would generally have a FPG concentration between above about 250 mg/dl.

The term "insulin resistance" as used herein refers to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

The term "metabolic syndrome" refers to an associated cluster of traits that includes, but is not limited to, hyperinsulinemia, abnormal glucose tolerance, obesity, redistribution of fat to the abdominal or upper body compartment, hypertension, dysfibrinolysis, and dyslipidemia characterized by high triglycerides, low high density lipoprotein (HDL)-cholesterol, and high small dense low density lipoprotein (LDL) particles. Subjects having metabolic syndrome are at risk for development of Type 2 diabetes and, for example, atherosclerosis.

The phrase "glucose metabolism disorder" encompasses any disorder characterized by a clinical symptom or a combination of clinical symptoms that is associated with an elevated level of glucose and/or an elevated level of insulin in a subject relative to a healthy individual. Elevated levels of glucose and/or insulin may be manifested in the following diseases, disorders and conditions: hyperglycemia, type II diabetes, gestational diabetes, type I diabetes, insulin resistance, impaired glucose tolerance, hyperinsulinemia, impaired glucose metabolism, pre-diabetes, metabolic disorders (such as metabolic syndrome, which is also referred to as syndrome X), and obesity, among others. The Polypeptides of the present disclosure, and compositions thereof, can be used, for example, to achieve and/or maintain glucose homeostasis, e.g., to reduce glucose level in the bloodstream and/or to reduce insulin level to a range found in a healthy subject.

The term "hyperglycemia", as used herein, refers to a condition in which an elevated amount of glucose circulates in the blood plasma of a subject relative to a healthy individual. Hyperglycemia can be diagnosed using methods known in the art, including measurement of fasting blood glucose levels as described herein.

The term "hyperinsulinemia", as used herein, refers to a condition in which there are elevated levels of circulating insulin when, concomitantly, blood glucose levels are either elevated or normal. Hyperinsulinemia can be caused by insulin resistance which is associated with dyslipidemia such as high triglycerides, high cholesterol, high low-density lipoprotein (LDL) and low high-density lipoprotein (HDL); high uric acids levels; polycystic ovary syndrome; type II diabetes and obesity. Hyperinsulinemia can be diagnosed as having a plasma insulin level higher than about 2 µU/mL.

As used herein, the phrase "body weight disorder" refers to conditions associated with excessive body weight and/or enhanced appetite. Various parameters are used to determine whether a subject is overweight compared to a reference healthy individual, including the subject's age, height, sex and health status. For example, a subject may be considered overweight or obese by assessment of the subject's Body Mass Index (BMI), which is calculated by dividing a subject's weight in kilograms by the subject's height in meters squared. An adult having a BMI in the range of ~18.5 to ~24.9 kg/m² is considered to have a normal weight; an adult having a BMI between ~25 and ~29.9 kg/m² may be considered overweight (pre-obese); an adult having a BMI of ~30 kg/m² or higher may be considered obese. Enhanced appetite frequently contributes to excessive body weight. There are several conditions associated with enhanced appetite, including, for example, night eating syndrome, which is characterized by morning anorexia and evening polyphagia often associated with insomnia, but which may be related to injury to the hypothalamus.

The term "Activators" refers to agents that, for example, stimulate, increase, activate, facilitate, enhance activation, sensitize or up-regulate the function or activity of one or more Polypeptides. In addition, Activators include agents that operate through the same mechanism of action as the Polypeptides (i.e., agents that modulate the same signaling pathway as the Polypeptides in a manner analogous to that of the Polypeptides) and are capable of eliciting a biological response comparable to (or greater than) that of the Polypeptides. Examples of Activators include agonists such as small molecule compounds.

The term "Modulators" collectively refers to the Polypeptides and the Activators.

The terms "modulate", "modulation" and the like refer to the ability of the Modulators to increase the function or activity of one or more Polypeptides (or the nucleic acid molecules encoding them), either directly or indirectly.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

It will be appreciated that throughout this disclosure reference is made to amino acids according to the single letter or three letter codes. For the reader's convenience, the single and three letter amino acid codes are provided below:

| G | Glycine | Gly | P | Proline | Pro |
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein, the term "variant" encompasses naturally-occurring variants (e.g., homologs and allelic variants) and non-naturally-occurring variants (e.g., muteins). Naturally-occurring variants include homologs, i.e., nucleic acids and polypeptides that differ in nucleotide or amino acid sequence, respectively, from one species to another. Naturally-occurring variants include allelic variants, i.e., nucleic acids and polypeptides that differ in nucleotide or amino acid sequence, respectively, from one individual to another within a species. Non-naturally-occurring variants include nucleic acids and polypeptides that comprise a change in nucleotide or amino acid sequence, respectively, where the change in sequence is artificially introduced, e.g., the change is generated in the laboratory or other facility by human intervention ("hand of man").

The term "native," in reference to GDF15, refers to biologically active, naturally-occurring GDF15, including biologically active, naturally-occurring GDF15 variants.

The term "muteins" as used herein refers broadly to mutated recombinant proteins, i.e., a polypeptide comprising an artificially introduced change in amino acid sequence, e.g., a change in amino acid sequence generated in the laboratory or other facility by human intervention ("hand of man"). These proteins usually carry single or multiple amino acid substitutions and are frequently derived from cloned genes that have been subjected to site-directed or random mutagenesis, or from completely synthetic genes.

As used herein in reference to native human GDF15 or a GDF15 mutein, the terms "modified", "modification" and the like refer to one or more changes that enhance a desired property of human GDF15, a naturally-occurring GDF15 variant, or a GDF15 mutein, where the change does not alter the primary amino acid sequence of the GDF15. "Modification" includes a covalent chemical modification that does not alter the primary amino acid sequence of the GDF15 polypeptide itself. Such desired properties include, for example, prolonging the circulation half-life, increasing the stability, reducing the clearance, altering the immunogenicity or allergenicity, and enabling the raising of particular antibodies (e.g., by introduction of unique epitopes) for use in detection assays. Changes to human GDF15, a naturally-occurring GDF15 variant, or a GDF15 mutein that may be carried out include, but are not limited to, pegylation (covalent attachment of one or more molecules of polyethylene glycol (PEG), or derivatives thereof); glycosylation (e.g., N-glycosylation), polysialylation and hesylation; albumin fusion; albumin binding through, for example, a conjugated fatty acid chain (acylation); Fc-fusion; and fusion with a PEG mimetic.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

The term "Probe" refers to a fragment of DNA or RNA corresponding to a gene or sequence of interest, wherein the fragment has been labeled radioactively (e.g., by incorporating $32^P$ or $35^S$) or with some other detectable molecule, such as biotin, digoxygenin or fluorescein. As stretches of DNA or RNA with complementary sequences will hybridize, a probe can be used to, for example, label viral plaques, bacterial colonies or bands on a gel that contain the gene of interest. A probe can be cloned DNA or it can be a synthetic DNA strand; the latter can be used to obtain a cDNA or genomic clone from an isolated protein by, for example, microsequencing a portion of the protein, deducing the nucleic acid sequence encoding the protein, synthesizing an oligonucleotide carrying that sequence, radiolabeling the sequence and using it as a probe to screen a cDNA library or a genomic library.

The term "heterologous" refers to two components that are defined by structures derived from different sources. For example, in the context of a polypeptide, a "heterologous" polypeptide may include operably linked amino acid sequences that are derived from different polypeptides (e.g., a first component comprising a recombinant polypeptide and a second component derived from a native GDF15 polypeptide). Similarly, in the context of a polynucleotide encoding a chimeric polypeptide, a "heterologous" polynucleotide may include operably linked nucleic acid sequences that can be derived from different genes (e.g., a first component from a nucleic acid encoding a polypeptide according to an embodiment disclosed herein and a second component from a nucleic acid encoding a carrier polypeptide). Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin than the promoter, the coding sequence or both). For example, a T7 promoter operably linked to a polynucleotide encoding a GDF15 Polypeptide or domain thereof is said to be a heterologous nucleic acid. In the context of recombinant cells, "heterologous" can refer to the presence of a nucleic acid (or gene product, such as a polypeptide) that is of a different genetic origin than the host cell in which it is present.

The term "operably linked" refers to linkage between molecules to provide a desired function. For example, "operably linked" in the context of nucleic acids refers to a functional linkage between a nucleic acid expression control sequence (such as a promoter, signal sequence, or array of transcription factor binding sites) and a second polynucleotide, wherein the expression control sequence affects transcription and/or translation of the second polynucleotide. In the context of a polypeptide, "operably linked" refers to a functional linkage between amino acid sequences (e.g., of different domains) to provide for a described activity of the polypeptide.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" a GDF15 polypeptide), is meant to indicate that the polypeptide or nucleic acid has a sequence that is based on that of a reference polypeptide or nucleic acid (e.g., a naturally occurring GDF15 polypeptide or a GDF15-encoding nucleic acid), and is not meant to be limiting as to the source or method in which the protein or nucleic acid is made. By way of example, the term "derived from" includes homologues or variants of reference amino acid or DNA sequences.

"Isolated" refers to a polypeptide of interest that, if naturally occurring, is in an environment different from that in which it may naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates the polypeptide has been separated from an environment in which it was made by either synthetic or recombinant means.

"Enriched" means that a sample is non-naturally manipulated (e.g., by a scientist or a clinician) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "antibodies" (Abs) and "immunoglobulins" (Igs) refer to glycoproteins having the same structural characteristics. While antibodies exhibit binding specificity to a specific antigen, immunoglobulins include both antibodies and other antibody-like molecules which lack antigen specificity. Antibodies are described in detail hereafter.

The term "monoclonal antibody" refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. In contrast to polyclonal antibody preparations which include different antibodies directed against different determinants (epitopes), each monoclonal antibody is directed against a single determinant on the antigen.

An "isolated" antibody is one which has been separated and/or recovered from contaminant components of its natural environment; such contaminant components are materials which might interfere with diagnostic or therapeutic uses for the antibody, and may include enzymes, hormones, and other proteinaceous or nonproteinaceous solutes.

Growth Differentiation Factor 15 (GDF15)

GDF15, also known as MIC-1 (macrophage inhibitory cytokine-1), PDF, PLAB, NAG-1, TGF-PL, and PTGFB, is a member of the transforming growth factor β (TGF-β) super-family. GDF15, which is synthesized as a 62 kDa intracellular precursor protein that is subsequently cleaved by a furin-like protease, is secreted as a 25 kDa disulfide-linked protein. [See, e.g., Fairlie et al., J. Leukoc. Biol 65:2-5 (1999)]. GDF15 mRNA is seen in several tissues, including liver, kidney, pancreas, colon and placenta, and GDF15 expression in liver can be significantly up-regulated during injury of organs such as the liver, kidneys, heart and lungs.

The GDF15 precursor is a 308 amino acid polypeptide (NCBI Ref. Seq.NP_004855.2) containing a 29 amino acid signal peptide, a 167 amino acid pro-domain, and a mature domain of 112 amino acids which is excised from the pro-domain by furin-like proteases. A 308-amino acid GDF15 polypeptide is referred to as a "full-length" GDF15 polypeptide; a 112-amino acid GDF15 polypeptide (e.g., amino acids 197-308 of the amino acid sequence depicted in FIG. 1A) is a "mature" GDF15 polypeptide. Unless otherwise indicated, the term "GDF15" refers to the 112 amino acid mature sequence. In addition, numerical references to particular GDF15 residues refer to the 112 amino acid mature sequence (i.e., residue 1 is Ala (A), and residue 112 is Ile (I); see FIG. 1B).

The scope of the present disclosure includes GDF15 orthologs, and modified forms thereof, from other mammalian species, and their use, including mouse (NP_035949), chimpanzee (XP_524157), orangutan (XP_002828972), Rhesus monkey (EHH29815), giant panda (XP_002912774), gibbon (XP_003275874), guinea pig (XP_003465238), ferret (AER98997), cow (NP_001193227), pig (NP_001167527) and dog (XP_541938). The mature form of human GDF15 has approximately 67% amino acid identity to the murine ortholog.

In particular embodiments, the agents contemplated by the present disclosure are modified human GDF15 molecules, whereas in other embodiments the agents are GDF15 variants (e.g., muteins) or modified GDF15 variants. The modified human GDF15 molecules, GDF15 variants (e.g., muteins) and modified GDF15 variants have sufficient homology to human GDF15 such that they have the ability to bind the GDF15 receptor(s) and initiate a signal transduction pathway resulting in, for example, reduced body weight and/or the other physiological effects described herein. The present disclosure also contemplates nucleic acid molecules encoding the foregoing. As indicated above, the modified human GDF15 molecules, the GDF15 variants (e.g., muteins), and the modified GDF15 variants are collectively referred to hereafter as the "Polypeptide(s)". In addition, fragments of the Polypeptides that retain activity comparable to, or greater than, native GDF15 are contemplated by the present disclosure.

The GDF15 muteins contemplated herein include one or more substitutions of native lysine residues (i.e., residues 62, 69, 91 and 107) with any other amino acid. However, all GDF15 muteins containing K62Q (e.g., variants v2, v3 and v4; see FIG. 2) are inactive and behave as negative control proteins. In contrast, GDF15 muteins retaining K62 but incorporating any combination of K69Q, K91R and/or K107R (e.g., variants v1, v5, v6 and v7; see FIG. 2) are active in lowering body weight to a level comparable to that of wild-type control. In other GDF15 muteins, one or more GDF15 residue is substituted with another amino acid, including, for example, the following substitutions: H18Q, T19S or V20L. Examples of other GDF15 muteins are set forth hereafter. GDF15 muteins also include a GDF15 polypeptide that includes a non-naturally-occurring proline at the amino terminus. As an example, the amino acid sequence of a naturally-occurring mature GDF15 polypeptide can be modified to include an N-terminal proline; the resulting mutein can have a length of 113 amino acids. As another example, the amino acid sequence of a non-naturally-occurring GDF15 variant can include an N-terminal proline.

Several techniques, described in detail hereafter, may be used to modify native GDF15 and GDF15 muteins, including pegylation, N-glycosylation, albumin fusion molecules and Fc-fusion molecules. By way of example, human GDF15 or a GDF15 mutein may be modified by covalent attachment of one or more PEG molecules at the N-terminus alanine residue (i.e., A1) or at one or more lysine residues within the mature polypeptide (i.e., residues 62, 69, 91 and 107). In particular embodiments, strategies are employed such that pegylation is effected only at specific lysine residues (i.e., site-specific modification). Using standard pegylation techniques, lysine62 is not modified because it is likely buried within the hydrophobic core of the protein dimer interface; thus, it is not necessary to mutate lysine62 in order to prevent its pegylation (moreover, as noted above, muteins comprising K62Q are inactive). Examples of modified GDF15 molecules and modified GDF15 muteins are described hereafter.

Compared to native GDF15, the modified forms of GDF15, the GDF15 variants (e.g., muteins), and the modified GDF15 variants may possess certain desirable properties, including, for example, improved stability and extended serum half-life. Furthermore, as compared to native GDF15, the modified forms of GDF15, the GDF15 variants, and the modified GDF15 variants may enable the raising of particular antibodies (e.g., by introduction of unique epitopes) for use in detection assays, provide for ease of protein purification, etc.

In addition to the Polypeptides, the present disclosure contemplates other GDF15-related agents (i.e., Activators) capable of eliciting a biological response comparable to (or greater than) that of the Polypeptides, and/or agents capable of enhancing the activity of the Polypeptides.

A. GDF15 Muteins, Modified GDF15 and Modified GDF15 Muteins

The present disclosure contemplates GDF15 muteins wherein one or more amino acid residues of the mature polypeptide are substituted with another residue. In particular embodiments, one or more lysine residues (i.e., residues 62, 69, 91 and 107) are substituted with any other amino acid. Whereas GDF15 muteins containing K62Q are inactive and behave as negative control proteins (e.g., they do not lower body weight at two weeks post-administration), GDF15 muteins retaining K62 but incorporating any combination of K69Q, K91R and/or K107R are active in lowering body weight to a level comparable to that of wild-type control. In other embodiments, one or more GDF15 residue is substituted with another amino acid (e.g., H18Q, T19S or V20L). Examples of GDF15 muteins include, but are not limited to the following (see FIG. 2):

mutein v1) K69Q, K91R, K107R (SEQ ID NO:5);
mutein v2) K62Q, K91R, K107R (SEQ ID NO:6);
mutein v3) K62Q, K69Q, K107R (SEQ ID NO:7);
mutein v4) K62Q, K69Q, K91R (SEQ ID NO:8);
mutein v5) K91R, K107R (SEQ ID NO:9);
mutein v6) K69Q, K107R (SEQ ID NO:10);
mutein v7) K69Q, K91R (SEQ ID NO:11);
mutein v8) H18Q, T19S, V20L, K62Q, K69Q, K91R, K107R (SEQ ID NO:12);
mutein v9) H18Q, T19S, V20L, K62Q, K91R, K107R (SEQ ID NO:13);
mutein v10) H18Q, T19S, V20L, K62Q, K69Q, K107R (SEQ ID NO:14); and
mutein v11) H18Q, T19S, V20L, K62Q, K69Q, K91R (SEQ ID NO:15).

The effect of particular GDF15 muteins on body weight and fasted glucose serum levels was compared to that of GDF15. To ensure the accuracy of such a comparison, systemic exposure levels of GDF15 in mice were first determined from the genetic methods described in the Experimental section (see, e.g., FIG. 3) in order to establish a clear relationship of observed phenotype (e.g., body weight and glucose levels) and GDF15 serum concentrations (see, e.g., FIGS. 4-7). Using these exposure levels as a benchmark, mice were subsequently administered recombinant GDF15 at doses that attained approximately equivalent serum level concentrations to those observed via the genetic methods. As indicated in FIG. 8, exposure to recombinant GDF15 was within the equivalent range (ng/mL) to that established in FIG. 3; thus, these data established a correlation of equivalency between serum GDF15 levels and body weight and blood glucose phenotypes for both the genetic and the recombinant GDF15 modalities.

Thereafter, the effects of native mature human GDF15 and particular GDF15 muteins on body weight and fasted glucose serum levels were evaluated. In particular, the effect of GDF15 and GDF15 muteins v1-v7 (see FIG. 2) on body weight reduction in mice is set forth in FIG. 6, and the effect of GDF15 and GDF15 muteins v1-v7 on fasted serum blood glucose reduction in mice is set forth in FIG. 7. As described in the Experimental section, various GDF15 muteins exhibited similar effects to those observed with GDF15. For comparison purposes, it was established that administration of recombinant GDF15 significantly decreased food intake (see FIG. 9) and body weight (see FIG. 10) and resulted in significantly decreased non-fasted blood glucose serum levels (see FIG. 11).

As indicated above and as described in more detail below, in order to enhance one or more properties, native GDF15 and GDF15 muteins may be modified through, for example, pegylation (covalent attachment of one or more molecules of polyethylene glycol (PEG), or derivatives thereof); glycosylation (e.g., N-glycosylation) and polysialylation; albumin fusion; albumin binding through, for example, a conjugated fatty acid chain (acylation); Fc-fusion; and fusion with a PEG mimetic. In particular embodiments, the modifications are introduced in a site-specific manner.

In some embodiments of the present disclosure, human GDF15 or a GDF15 mutein is modified by covalent attachment of one or more PEG molecules at the N-terminus alanine residue (i.e., A1) and/or at one or more lysine residues within the mature polypeptide (i.e., residues 62, 69, 91 and 107). In particular embodiments, strategies are employed such that pegylation occurs only at specific residues. By way of example, a proline residue may be introduced N-terminal to the alanine residue at position one (i.e., the N-terminus alanine) to prevent pegylation of the alanine's free amine group. In such variants, residue one is the N-terminus proline and residue 113 is isoleucine. Native mature GDF15 and GDF15 muteins containing the N-terminus proline include, but are not limited to, the following (see FIG. 2):

mutein v12) NPro-GDF15 (SEQ ID NO:16);
mutein v13) NPro, K70Q, K92R, K108R (SEQ ID NO:17);
mutein v14) NPro, K63Q, K92R, K108R (SEQ ID NO:18);
mutein v15) NPro, K63Q, K70Q, K108R (SEQ ID NO:19);
mutein v16) NPro, K63Q, K70Q, K92R (SEQ ID NO:20);
mutein v17) NPro, K92R, K108R (SEQ ID NO:21);
mutein v18) NPro, K70Q, K108R (SEQ ID NO:22);
mutein v19) NPro, K70Q, K92R (SEQ ID NO:23);
mutein v20) NPro, H19Q, T205, V21L, K63Q, K70Q, K92R, K108R (SEQ ID NO:24);
mutein v21) NPro, H19Q, T205, V21L, K63Q, K92R, K108R (SEQ ID NO:25);
mutein v22) NPro, H19Q, T205, V21L, K63Q, K70Q, K108R (SEQ ID NO:26); and
mutein v23) NPro, H19Q, T205, V21L, K63Q, K70Q, K92R (SEQ ID NO:27).

Moreover, as detailed in the Experimental section, N-Hydroxysuccinimide (NHS)-specific chemistries may be employed to modify the recombinant GDF15 muteins of the present disclosure in a site-specific manner. For example, when desired, prevention of PEGylation at the N-terminal alanine can be achieved using sulfo-NHS-acetate to introduce an acetyl moiety that serves as a protecting group. In order to prevent pegylation of one or more internal lysine residues, lysine substitutions such as those described above can be introduced; because lysine62 is not pegylated using standard techniques, it is unnecessary to mutate the residue in order to prevent its pegylation. Using these NHS chemistries, the following variants were modified by attachment of a linear 10 kDa PEG moiety (see Example 4): variant 1 was PEGylated at the N-terminus (v1-PEG10) (SEQ ID NO:5); variant 5 was PEGylated at lysine69 (v5-PEG10) (SEQ ID NO:9); and variant 6 was PEGylated at lysine91 (v6-PEG10) (SEQ ID NO:10).

Nucleic acid molecules encoding the Polypeptides are contemplated by the present disclosure, including their naturally-occurring and non-naturally occurring isoforms, allelic variants and splice variants. As previously noted, a Polypeptide also refers to polypeptides that have one or more alterations in the amino acid residues (e.g., at locations that are not conserved across variants or species) while retaining the conserved domains and having the same biological activity as the naturally-occurring Polypeptides. The present disclosure also encompasses nucleic acid sequences that vary in one or more bases from a naturally-occurring DNA sequence but still translate into an amino acid sequence that corresponds to a Polypeptide due to degeneracy of the genetic code. For example, GDF15 may refer to amino acid sequences that differ from the naturally-occurring sequence by one or more conservative substitutions, tags, or conjugates (e.g., a Polypeptide).

Thus, in addition to any naturally-occurring GDF15 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution (e.g., a Polypeptide).

By "conservative amino acid substitution" generally refers to substitution of amino acid residues within the following groups: 1) L, I, M, V, F; 2) R, K; 3) F, Y, H, W, R; 4) G, A, T, S; 5) Q, N; and 6) D, E. Conservative amino acid substitutions preserve the activity of the protein by replacing an amino acid(s) in the protein with an amino acid with a side chain of similar acidity, basicity, charge, polarity, or size of the side chain. Guidance for substitutions, insertions, or deletions may be based on alignments of amino acid sequences of different variant proteins or proteins from different species.

The present disclosure also contemplates active fragments (e.g., subsequences) of the Polypeptides containing contiguous amino acid residues derived from the mature GDF15 polypeptide or a GDF15 mutein. The length of contiguous amino acid residues of a peptide or a polypeptide subsequence varies depending on the specific naturally-occurring amino acid sequence from which the subsequence is derived. In general, peptides and polypeptides may be from about 5 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 40 amino acids, from about 40 amino acids to about 50 amino acids, from about 50 amino acids to about 75 amino acids, from about 75 amino acids to about 100 amino acids, or from about 100 amino acids up to the length of the mature peptide or polypeptide.

Additionally, the Polypeptides can have a defined sequence identity compared to a reference sequence over a defined length of contiguous amino acids (e.g., a "comparison window"). Methods of alignment of sequences for comparison are well-known in the art.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable Polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 5 amino acids to about 10 amino acids, from about 10 amino acids to 12 amino acids, from about 12 amino acids to about 15 amino acids, from about 15 amino acids to about 20 amino acids, from about 20 amino acids to about 25 amino acids, from about 25 amino acids to about 30 amino acids from about 30 amino acids to about 35 amino acids, from about 35 amino acids to about 40 amino acids, from about 40 amino acids to about 45 amino acids, from about 45 amino acids to about 50 amino acids, from about 50 amino acids to about 60 amino acids, from about 60 amino acids to about 70 amino acids, from about 70 amino acids to about 80 amino acids, from about 80 amino acids to about 90 amino acids, from about 90 amino acids to about 100 amino acids, or from about 100 amino acids to 112 amino acids or 113 amino acids, of one of the following reference amino acid sequences: v1-v23 (see, e.g., FIG. 2).

The Polypeptides may be isolated from a natural source (e.g., an environment other than its naturally-occurring environment) and also may be recombinantly made (e.g., in a genetically modified host cell such as bacteria; yeast; *Pichia*; insect cells; and the like), where the genetically modified host cell is modified with a nucleic acid comprising a nucleotide sequence encoding the polypeptide. The Polypeptides may also be synthetically produced (e.g., by cell-free chemical synthesis). Methods of productions are described in more detail below.

A Polypeptide may be generated using recombinant techniques to manipulate different GDF15-related nucleic acids known in the art to provide constructs capable of encoding the Polypeptide. It will be appreciated that, when provided a particular amino acid sequence, the ordinary skilled artisan will recognize a variety of different nucleic acid molecules encoding such amino acid sequence in view of her background and experience in, for example, molecular biology.

B. Modulators

The term "Modulators" refers to both Polypeptides and Activators. As indicated above, Activators are agents that, for example, stimulate, increase, activate, facilitate, enhance activation, sensitize or up-regulate the function or activity of one or more Polypeptides. In addition, Activators include agents that operate through the same mechanism of action as the Polypeptides (i.e., agents that modulate the same signaling pathway as the Polypeptides in a manner analogous to that of the Polypeptides) and are capable of eliciting a biological response comparable to (or greater than) that of the Polypeptides. An Activator may be, for example, a small molecule agonist compound, or other bioorganic molecule.

In some embodiments, the Activator is a small molecule agonist compound. Numerous libraries of small molecule compounds (e.g., combinatorial libraries) are commercially available and can serve as a starting point for identifying such an Activator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

In still further embodiments, the Activator is an agonistic polypeptide structurally distinguishable from the Polypeptides but having comparable activity. The skilled artisan is able to identify such polypeptides having desired properties.

Amide Bond Substitutions

In some cases, a Polypeptide includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of a Polypeptide can be substituted.

In another example, one or more amide linkages (—CO—NH—) in a Polypeptide can be replaced with a linkage which is an isostere of an amide linkage, such as —CH$_2$NH—, CH$_2$S—, —CH$_2$CH$_2$—, —CH=CH-(cis and trans), —COCH$_2$—, —CH(OH)CH$_2$— or —CH$_2$SO—. One or more amide linkages in a Polypeptide can also be replaced by, for example, a reduced isostere pseudopeptide bond. See Couder et al. (1993) Int. J. Peptide Protein Res. 41:181-184. Such replacements and how to effect are known to those of ordinary skill in the art.

Amino Acid Substitutions

One or more amino acid substitutions can be made in a Polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination) carboxylic acids or any of the many well-known activated derivatives such as acid chlorides, active esters, active azolides and related derivatives) and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopropionic acid, ornithine or lysine and tetrazole-substituted alkyl amino acids;

e) substitution of side chain amide residue, including asparagine, glutamine, and alkyl or aromatic substituted derivatives of asparagine or glutamine; and f) substitution of hydroxyl containing amino acids, including serine, threonine, homoserine, 2,3-diaminopropionic acid, and alkyl or aromatic substituted derivatives of serine or threonine.

In some cases, a Polypeptide comprises one or more naturally occurring non-genetically encoded L-amino acids, synthetic L-amino acids or D-enantiomers of an amino acid. For example, a Polypeptide can comprise only D-amino acids. For example, a Polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

A cysteine residue or a cysteine analog can be introduced into a Polypeptide to provide for linkage to another peptide via a disulfide linkage or to provide for cyclization of the Polypeptide. Methods of introducing a cysteine or cysteine analog are known in the art; see, e.g., U.S. Pat. No. 8,067,532.

A Polypeptide can be cyclized. One or more cysteine or cysteine analogs can be introduced into a Polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moiety) that can form a cyclizing bond can be used and/or introduced. A cyclizing bond can be generated with any combination of amino acids (or with amino acid and —$(CH_2)_n$—O— or —$(CH_2)_n$—$C_6H_4$—CO—) with functional groups which allow for the introduction of a bridge. Some examples are disulfides, disulfide mimetics such as the —$(CH_2)_n$— carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives of the modulator compounds of the present disclosure include C-terminal hydroxymethyl derivatives, O-modified derivatives (e.g., C-terminal hydroxymethyl benzyl ether), N-terminally modified derivatives including substituted amides such as alkylamides and hydrazides.

In some cases, one or more L-amino acids in a Polypeptide is replaced with a D-amino acid.

In some cases, a Polypeptide is a retroinverso analog. Sela and Zisman (1997) FASEB J. 11:449. Retro-inverso peptide analogs are isomers of linear polypeptides in which the direction of the amino acid sequence is reversed (retro) and the chirality, D- or L-, of one or more amino acids therein is inverted (inverso) e.g., using D-amino acids rather than L-amino acids. See, e.g., Jameson et al. (1994) Nature 368:744; and Brady et al. (1994) Nature 368:692.

A Polypeptide can include a "Protein Transduction Domain" (PTD), which refers to a polypeptide, polynucleotide, carbohydrate, or organic or inorganic compound that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of a Polypeptide, while in other embodiments, a PTD is covalently linked to the carboxyl terminus of a Polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO:28); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an *Drosophila Antennapedia* protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:29); Transportan GWTLNSAGYLLGKINLKALAALAKKIL (SEQ ID NO:30); KALAWEAKLAKALAKALAKHLAKALAKALKCEA (SEQ ID NO:31); and RQIKIWFQNRRMKWKK (SEQ ID NO:32). Exemplary PTDs include, but are not limited to, YGRKKRRQRRR (SEQ ID NO:28), RKKRRQRRR (SEQ ID NO:33); an arginine homopolymer of from 3 arginine residues to 50 arginine residues; Exemplary PTD domain amino acid sequences include, but are not limited to, any of the following:

YGRKKRRQRRR; (SEQ ID NO: 28)

RKKRRQRR; (SEQ ID NO: 34)

YARAAARQARA; (SEQ ID NO: 35)

THRLPRRRRRR; (SEQ ID NO: 36)
and

GGRRARRRRRR. (SEQ ID NO: 37)

The carboxyl group $COR_3$ of the amino acid at the C-terminal end of a Polypeptide can be present in a free form ($R_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched $C_1$-$C_6$-alkyl alcohols, e.g., ethyl alcohol or tert-butanol. The carboxyl group can also be amidated with primary or secondary amines such as ammonia, branched or unbranched $C_1$-$C_6$-alkylamines or $C_1$-$C_6$ di-alkylamines, e.g., methylamine or dimethylamine.

The amino group of the amino acid $NR_1R_2$ at the N-terminus of a Polypeptide can be present in a free form ($R_1$=H and $R_2$=H) or in the form of a physiologically-tolerated salt such as, e.g., a chloride or acetate. The amino group can also be acetylated with acids such that $R_1$=H and $R_2$=acetyl, trifluoroacetyl, or adamantyl. The amino group can be present in a form protected by amino-protecting groups conventionally used in peptide chemistry such as, e.g., Fmoc, Benzyloxy-carbonyl (Z), Boc, or Alloc. The amino group can be N-alkylated in which $R_1$ and/or $R_2$=$C_1$-$C_6$ alkyl or $C_2$-$C_8$ alkenyl or $C_7$-$C_9$ aralkyl. Alkyl residues can be straight-chained, branched or cyclic (e.g., ethyl, isopropyl and cyclohexyl, respectively).

Particular Modifications to Enhance and/or Mimic GDF15 Function

A Polypeptide can include one or more modifications that enhance a property desirable in a protein formulated for therapy (e.g., serum half-life), that enable the raising of antibodies for use in detection assays (e.g., epitope tags), that provide for ease of protein purification, etc. Such modifications include, but are not limited to, including pegylation (covalent attachment of one or more molecules of polyethylene glycol (PEG), or derivatives thereof); N-glycosylation and polysialylation; albumin fusion; albumin binding through a conjugated fatty acid chain (acylation); Fc-fusion proteins; and fusion with a PEG mimetic.

Pegylation:

The clinical effectiveness of protein therapeutics is often limited by short plasma half-life and susceptibility to protease degradation. Studies of various therapeutic proteins (e.g., filgrastim) have shown that such difficulties may be overcome by various modifications, including conjugating or linking the polypeptide sequence to any of a variety of nonproteinaceous polymers, e.g., polyethylene glycol (PEG), polypropylene glycol, or polyoxyalkylenes (see, for example, typically via a linking moiety covalently bound to both the protein and the nonproteinaceous polymer, e.g., a PEG). Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, but certain embodiments have a molecular weight between 500 and 20,000 while other embodiments have a molecular weight between 4,000 and 10,000.

The present disclosure also contemplates compositions of conjugates wherein the PEGs have different n values and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. For example, cation exchange chromatography may be used to separate conjugates, and a fraction is then identified which contains the conjugate having, for example, the desired number of PEGs attached, purified free from unmodified protein sequences and from conjugates having other numbers of PEGs attached.

PEG may be bound to a polypeptide of the present disclosure via a terminal reactive group (a "spacer"). The spacer is, for example, a terminal reactive group which mediates a bond between the free amino or carboxyl groups of one or more of the polypeptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art may be used to terminate the reaction. In some embodiments the reaction is terminated by acidifying the reaction mixture and freezing at, e.g., −20° C.

The present disclosure also contemplates the use of PEG Mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Glycosylation and Polysialylation:

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties of proteins and can also be important in protein stability, secretion, and subcellular localization. Proper glycosylation can be essential for biological activity. In fact, some genes from eucaryotic organisms, when expressed in bacteria (e.g., *E. coli*) which lack cellular processes for glycosylating proteins, yield proteins that are recovered with little or no activity by virtue of their lack of glycosylation.

Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants.

The polypeptide sequences of the present disclosure may optionally be altered through changes at the DNA level, particularly by mutating the DNA encoding the polypeptide at preselected bases such that codons are generated that will translate into the desired amino acids. Another means of increasing the number of carbohydrate moieties on the polypeptide is by chemical or enzymatic coupling of glycosides to the polypeptide. Removal of carbohydrates may be accomplished chemically or enzymatically, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases.

Dihydrofolate reductase (DHFR)-deficient Chinese Hamster Ovary (CHO) cells are a commonly used host cell for the production of recombinant glycoproteins. These cells do not express the enzyme beta-galactoside alpha-2,6-sialyl-transferase and therefore do not add sialic acid in the alpha-2,6 linkage to N-linked oligosaccharides of glycoproteins produced in these cells.

The present disclosure also contemplates the use of polysialylation, the conjugation of peptides and proteins to the naturally occurring, biodegradable α-(2→8) linked polysialic acid ("PSA") in order to improve their stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of activity in vivo activity, and reduction in immunogenicity and antigenicity (see, e.g., G. Gregoriadis et al., Int. J. Pharmaceutics 300(1-2):125-30). As with modifications with other conjugates (e.g., PEG), various techniques for site-specific polysialylation are available (see, e.g., T. Lindhout et al., PNAS 108(18)7397-7402 (2011)).

Albumin Fusion and Conjugation with Other Molecules:

Additional suitable components and molecules for conjugation include, for example, thyroglobulin; albumins such as human serum albumin (HAS); tetanus toxoid; Diphtheria toxoid; polyamino acids such as poly(D-lysine:D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Fusion of albumin to one or more polypeptides of the present disclosure can, for example, be achieved by genetic manipulation, such that the DNA coding for HSA, or a fragment thereof, is joined to the DNA coding for the one or more polypeptide sequences. Thereafter, a suitable host can be transformed or transfected with the fused nucleotide sequences in the form of, for example, a suitable plasmid, so as to express a fusion polypeptide. The expression may be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Transformation is used broadly herein to refer to the genetic alteration of a cell resulting from the direct uptake, incorporation and expression of exogenous genetic material (exogenous DNA) from its surroundings and taken up through the cell membrane(s). Transformation occurs naturally in some species of bacteria, but it can also be effected by artificial means in other cells.

Furthermore, albumin itself may be modified to extend its circulating half-life. Fusion of the modified albumin to one or more Polypeptides can be attained by the genetic manipulation techniques described above or by chemical conjugation; the resulting fusion molecule has a half-life that exceeds that of fusions with non-modified albumin. [See WO2011/051489].

Several albumin-binding strategies have been developed as alternatives for direct fusion, including albumin binding through a conjugated fatty acid chain (acylation). Because serum albumin is a transport protein for fatty acids, these natural ligands with albumin-binding activity have been used for half-life extension of small protein therapeutics. For example, insulin determir (LEVEMIR), an approved product for diabetes, comprises a myristyl chain conjugated to a genetically-modified insulin, resulting in a long-acting insulin analog.

Another type of modification is to conjugate (e.g., link) one or more additional components or molecules at the N- and/or C-terminus of a polypeptide sequence, such as another protein (e.g., a protein having an amino acid sequence heterologous to the subject protein), or a carrier molecule. Thus, an exemplary polypeptide sequence can be provided as a conjugate with another component or molecule.

A conjugate modification may result in a polypeptide sequence that retains activity with an additional or complementary function or activity of the second molecule. For example, a polypeptide sequence may be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated polypeptide sequence, a conjugate that targets a type of cell or organ more efficiently than an unconjugated polypeptide sequence, or a drug to further counter the causes or effects associated with a disorder or disease as set forth herein (e.g., diabetes).

A Polypeptide may also be conjugated to large, slowly metabolized macromolecules such as proteins; polysaccharides, such as sepharose, agarose, cellulose, cellulose beads; polymeric amino acids such as polyglutamic acid, polylysine; amino acid copolymers; inactivated virus particles; inactivated bacterial toxins such as toxoid from diphtheria, tetanus, cholera, leukotoxin molecules; inactivated bacteria; and dendritic cells. Such conjugated forms, if desired, can be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Purification methods such as cation exchange chromatography may be used to separate conjugates by charge difference, which effectively separates conjugates into their various molecular weights. For example, the cation exchange column can be loaded and then washed with ~20 mM sodium acetate, pH~4, and then eluted with a linear (0 M to 0.5 M) NaCl gradient buffered at a pH from about 3 to 5.5, e.g., at pH~4.5. The content of the fractions obtained by cation exchange chromatography may be identified by molecular weight using conventional methods, for example, mass spectroscopy, SDS-PAGE, or other known methods for separating molecular entities by molecular weight.

Fc-Fusion Molecules:

In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Other Modifications:

The present disclosure contemplates the use of other modifications, currently known or developed in the future, of the Polypeptides to improve one or more properties. One such method for prolonging the circulation half-life, increasing the stability, reducing the clearance, or altering the immunogenicity or allergenicity of a polypeptide of the present disclosure involves modification of the polypeptide sequences by hesylation, which utilizes hydroxyethyl starch derivatives linked to other molecules in order to modify the molecule's characteristics. Various aspects of hesylation are described in, for example, U.S. Patent Appln. Nos. 2007/0134197 and 2006/0258607.

Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 (e.g., Gly), 2, 3, 4, 5, 6, 7, 8, 9, 10, 10-20, 20-30, 30-50 amino acids (e.g., Gly).

Exemplary flexible linkers include glycine polymers $(G)_n$, glycine-serine polymers (for example, $(GS)_n$, $GSGGS_n$ (SEQ ID NO:40) and $GGGS_n$ (SEQ ID NO:41), where n is an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG (SEQ ID NO:42), GGSGG (SEQ ID NO:43), GSGSG (SEQ ID NO:44), GSGGG (SEQ ID NO:45), GGGSG (SEQ ID NO:46), and GSSSG (SEQ ID NO:47).

Methods of Production of Polypeptides

A polypeptide of the present disclosure can be produced by any suitable method, including recombinant and non-recombinant methods (e.g., chemical synthesis).

A. Chemical Synthesis

Where a polypeptide is chemically synthesized, the synthesis may proceed via liquid-phase or solid-phase. Solid-phase peptide synthesis (SPPS) allows the incorporation of unnatural amino acids and/or peptide/protein backbone modification. Various forms of SPPS, such as Fmoc and Boc, are available for synthesizing polypeptides of the present disclosure. Details of the chemical synthesis are known in the art (e.g., Ganesan A. 2006 Mini Rev. Med. Chem. 6:3-10; and Camarero J. A. et al., 2005 Protein Pept Lett. 12:723-8).

Solid phase peptide synthesis may be performed as described hereafter. The α functions (Nα) and any reactive side chains are protected with acid-labile or base-labile groups. The protective groups are stable under the conditions for linking amide bonds but can be readily cleaved without impairing the peptide chain that has formed. Suitable protective groups for the α-amino function include, but are not limited to, the following: t-butyloxycarbonyl (Boc), benzyloxycarbonyl (Z), o-chlorobenzyloxycarbonyl, bi-phenylisopropyloxycarbonyl, tert-amyloxycarbonyl (Amoc), a, α-dimethyl-3,5-dimethoxy-benzyloxycarbonyl, o-nitrosulfenyl, 2-cyano-t-butoxy-carbonyl, 9-fluorenylmethoxycarbonyl (Fmoc), 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl (2-CIZ), 2,6-dichlorobenzyl, cyclohexyl, cyclopentyl, 1-(4,4-dimethyl-2,6-dioxocyclohex-1-ylidene)ethyl (Dde), isopropyl, 4-methoxy-2,3-6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers and the like. Polystyrene (1%)-divinylbenzene or TentaGel® derivatized with 4-benzyloxybenzyl-alcohol (Wang-anchor) or 2-chlorotrityl chloride can be used if it is intended to prepare the peptidic acid. In the case of the peptide amide, polystyrene (1%) divinylbenzene or TentaGel® derivatized with 5-(4'-aminomethyl)-3',5'-dimethoxyphenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material with the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, o-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or also in the absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, e.g., in a 2-fold excess and at temperatures between about 10° C. and 50° C., e.g., 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride under the conditions described above.

The Nα-protected amino acid (e.g., the Fmoc amino acid) can be coupled to the 2-chlorotrityl resin in dichloromethane with the addition of DIEA with reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about −10° C. and 50° C. (e.g., about 25° C.), and reaction times between about 12 and 24 hours (e.g., about 18 hours). In addition the peptide can be cleaved from the support by re-esterification, e.g., with methanol.

The acidic solution that is obtained may be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecyl-silylsilica (ODS) phases.

B. Recombinant Production

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that may be used as host cells include insect cells, mammalian cells, and/or plant cells. Where mammalian host cells are used, they may include human cells (e.g., HeLa, 293, H9 and Jurkat cells); mouse cells (e.g., NIH3T3, L cells, and C127 cells); primate cells (e.g., Cos 1, Cos 7 and CV1) and hamster cells (e.g., Chinese hamster ovary (CHO) cells).

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host may be present to facilitate selection of cells containing the vector. Moreover, the expression construct may include additional elements. For example, the expression vector may have one or two replication systems, thus allowing it to be maintained in organisms, for example, in mammalian or insect cells for expression and in a prokaryotic host for cloning and amplification. In addition, the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification methods. In one embodiment, the protein may be isolated using metal chelate chromatography methods. Proteins may contain modifications to facilitate isolation.

The polypeptides may be prepared in substantially pure or isolated form (e.g., free from other polypeptides). The polypeptides can be present in a composition that is enriched for the polypeptide relative to other components that may be present (e.g., other polypeptides or other host cell components). For example, purified polypeptide may be provided such that the polypeptide is present in a composition that is substantially free of other expressed proteins, e.g., less than 90%, less than 60%, less than 50%, less than 40%, less than 30%, less than 20%, less than 10%, less than 5%, or less than 1%, of the composition is made up of other expressed proteins.

Antibodies

The present disclosure provides antibodies, including isolated antibodies, that specifically bind a GDF15 polypeptide, e.g., a GDF15 mutein of the present disclosure. The term "antibody" encompasses intact monoclonal antibodies, polyclonal antibodies, multispecific antibodies (e.g., bispecific antibodies) formed from at least two intact antibodies, and antibody binding fragments including Fab and F(ab)'$_2$, provided that they exhibit the desired biological activity. The basic whole antibody structural unit comprises a tetramer, and each tetramer is composed of two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. In contrast, the carboxy-terminal portion of each chain defines a constant region primarily responsible for effector function. Human light chains are classified as kappa and lambda, whereas human heavy chains are classified as mu, delta, gamma, alpha, or epsilon, and define the antibody's isotype as IgM, IgD, IgA, and IgE, respectively. Binding fragments are produced by recombinant DNA techniques, or by enzymatic or chemical cleavage of intact antibodies. Binding fragments include Fab, Fab', F(ab')$_2$, Fv, and single-chain antibodies.

Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Within light and heavy chains, the variable and constant regions are joined by a "J" region of about 12 or more amino acids, with the heavy chain also including a "D" region of about 10 more amino acids. The antibody chains all exhibit the same general structure of relatively conserved framework regions (FR) joined by three hyper-variable regions, also called "complementarity-determining regions" or "CDRs". The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4.

An intact antibody has two binding sites and, except in bifunctional or bispecific antibodies, the two binding sites are the same. A bispecific or bifunctional antibody is an artificial hybrid antibody having two different heavy/light chain pairs and two different binding sites. Bispecific antibodies can be produced by a variety of methods including fusion of hybridomas or linking of Fab' fragments.

As set forth above, binding fragments may be produced by enzymatic or chemical cleavage of intact antibodies. Digestion of antibodies with the enzyme papain results in two identical antigen-binding fragments, also known as "Fab" fragments, and an "Fc" fragment which has no antigen-binding activity. Digestion of antibodies with the enzyme pepsin results in a F(ab')$_2$ fragment in which the two arms of the antibody molecule remain linked and comprise two-antigen binding sites. The F(ab')$_2$ fragment has the ability to crosslink antigen.

As used herein, the term "Fab" refers to a fragment of an antibody that comprises the constant domain of the light chain and the CH1 domain of the heavy chain.

When used herein, the term "Fv" refers to the minimum fragment of an antibody that retains both antigen-recognition and antigen-binding sites. In a two-chain Fv species, this region includes a dimer of one heavy-chain and one light-chain variable domain in non-covalent association. In a single-chain Fv species, one heavy-chain and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. While the six CDRs, collectively, confer antigen-binding specificity to the antibody, even a single variable domain (or half of an Fv comprising only three CDRs specific for an antigen) has the ability to recognize and bind antigen.

When used herein, the term "complementarity determining regions" or "CDRs" refers to parts of immunological receptors that make contact with a specific ligand and determine its specificity.

The term "hypervariable region" refers to the amino acid residues of an antibody which are responsible for antigen-binding. The hypervariable region generally comprises amino acid residues from a CDR and/or those residues from a "hypervariable loop".

As used herein, the term "epitope" refers to binding sites for antibodies on protein antigens. Epitopic determinants usually comprise chemically active surface groupings of molecules such as amino acids or sugar side chains, as well as specific three-dimensional structural and charge characteristics. An antibody is said to bind an antigen when the dissociation constant is ≤1 μM, ≤100 nM, or ≤10 nM. An increased equilibrium constant ("$K_D$") means that there is less affinity between the epitope and the antibody, whereas a decreased equilibrium constant means that there is more affinity between the epitope and the antibody. An antibody with a $K_D$ of "no more than" a certain amount means that the antibody will bind to the epitope with the given $K_D$ or more strongly. Whereas $K_D$ describes the binding characteristics of an epitope and an antibody, "potency" describes the effectiveness of the antibody itself for a function of the antibody. There is not necessarily a correlation between an equilibrium constant and potency; thus, for example, a relatively low $K_D$ does not automatically mean a high potency.

The term "selectively binds" in reference to an antibody does not mean that the antibody only binds to a single substance, but rather that the $K_D$ of the antibody to a first substance is less than the $K_D$ of the antibody to a second substance. An antibody that exclusively binds to an epitope only binds to that single epitope.

When administered to humans, antibodies that contain rodent (i.e., murine or rat) variable and/or constant regions are sometimes associated with, for example, rapid clearance from the body or the generation of an immune response by the body against the antibody. In order to avoid the utilization of rodent-derived antibodies, fully human antibodies can be generated through the introduction of human antibody function into a rodent so that the rodent produces fully human antibodies. Unless specifically identified herein, "human" and "fully human" antibodies can be used interchangeably. The term "fully human" can be useful when distinguishing antibodies that are only partially human from those that are completely, or fully, human. The skilled artisan is aware of various methods of generating fully human antibodies.

In order to address possible human anti-mouse antibody responses, chimeric or otherwise humanized antibodies can be utilized. Chimeric antibodies have a human constant region and a murine variable region, and, as such, human anti-chimeric antibody responses may be observed in some patients. Therefore, it is advantageous to provide fully human antibodies against multimeric enzymes in order to avoid possible human anti-mouse antibody or human anti-chimeric antibody responses.

Fully human monoclonal antibodies can be prepared, for example, by the generation of hybridoma cell lines by techniques known to the skilled artisan. Other preparation methods involve the use of sequences encoding particular antibodies for transformation of a suitable mammalian host cell, such as a CHO cell. Transformation can be by any known method for introducing polynucleotides into a host cell, including, for example, packaging the polynucleotide in a virus (or into a viral vector) and transducing a host cell with the virus (or vector) or by transfection procedures known in the art. Methods for introducing heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. Mammalian cell lines available as hosts for expression are well known in the art and include, but are not limited to, CHO cells, HeLa cells, and human hepatocellular carcinoma cells.

The antibodies can be used to detect a Polypeptide of the present disclosure. For example, the antibodies can be used as a diagnostic by detecting the level of one or more Polypeptides of the present disclosure in a subject, and either comparing the detected level to a standard control level or to a baseline level in a subject determined previously (e.g., prior to any illness).

Another embodiment of the present disclosure entails the use of one or more human domain antibodies (dAb). dAbs are the smallest functional binding units of human antibodies (IgGs) and have favorable stability and solubility characteristics. The technology entails a dAb(s) conjugated to HSA (thereby forming a "AlbudAb"; see, e.g., EP1517921B, WO2005/118642 and WO2006/051288) and a molecule of interest (e.g., a polypeptide sequence of the present disclosure). AlbudAbs are often smaller and easier to manufacture in microbial expression systems, such as bacteria or yeast, than current technologies used for extending the serum half-life of polypeptides. As HSA has a half-life of about three weeks, the resulting conjugated molecule improves the half-life of the molecule of interest. Use of the dAb technology may also enhance the efficacy of the molecule of interest.

Therapeutic and Prophylactic Uses

The present disclosure provides methods for treating or preventing hyperglycemia, hyperinsulinemia, glucose intolerance, glucose metabolism disorders, obesity and other body weight disorders, as well as other metabolic and metabolic-associated diseases, disorders and conditions by the administration of the Polypeptides, or compositions thereof, as described herein. Such methods may also have an advantageous effect on one or more symptoms associated with a disease, disorder or condition by, for example, decreasing the severity or the frequency of a symptom.

In order to determine whether a subject may be a candidate for the treatment or prevention of hyperglycemia, hyperinsulinemia, glucose intolerance, and/or glucose disorders by the methods provided herein, various diagnostic methods known in the art may be utilized. Such methods include those described elsewhere herein (e.g., fasting plasma glucose (FPG) evaluation and the oral glucose tolerance test (oGTT)).

In order to determine whether a subject may be a candidate for the treatment or prevention of a body weight disorder (e.g., obesity) by the methods provided herein, parameters such as, but not limited to, the etiology and the extent of the subject's condition (e.g., how overweight the subject is compared to reference healthy individual) should be evaluated. For example, an adult having a BMI between ~25 and ~29.9 kg/m$^2$ may be considered overweight (pre-obese), while an adult having a BMI of ~30 kg/m$^2$ or higher may be considered obese. For subjects who are overweight and/or who have poor diets (e.g., diets high in fat and calories), it is common to initially implement and assess the effect of modified dietary habits and/or exercise regimens before initiating a course of therapy comprising one or more of the Polypeptides of the present disclosure. As discussed herein, the Polypeptides can effect appetite suppression.

Pharmaceutical Compositions

The Modulators (e.g., Polypeptides) of the present disclosure may be in the form of compositions suitable for administration to a subject. In general, such compositions are "pharmaceutical compositions" comprising one or more Modulators and one or more pharmaceutically acceptable or physiologically acceptable diluents, carriers or excipients. In certain embodiments, the Modulators are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions may be used in combination with other therapeutically active agents or compounds (e.g., glucose lowering agents) as described herein in order to treat or prevent the diseases, disorders and conditions as contemplated by the present disclosure.

The pharmaceutical compositions typically comprise a therapeutically effective amount of at least one of the Modulators (e.g., Polypeptides) contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that could be used in the pharmaceutical compositions and dosage forms. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), and N-tris[Hydroxymethyl] methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver the Polypeptides, including implants (e.g., implantable pumps) and catheter systems, both of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

The pharmaceutical compositions containing the active ingredient may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods of preparing liposomes are described in, for example, U.S. Pat. Nos. 4,235,871, 4,501,728, and 4,837,028. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally-occurring gums, for example, gum acacia or gum tragacanth; naturally-occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The present disclosure contemplates the administration of the Modulators in the form of suppositories for rectal administration of the drug. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The Modulators contemplated by the present disclosure may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of the disclosed Modulators (e.g., Polypeptides), and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation.

Depot injections, which are generally administered subcutaneously or intramuscularly, may also be utilized to release the Modulators disclosed herein over a defined period of time. Depot injections are usually either solid- or oil-based and generally comprise at least one of the formulation components set forth herein. One of ordinary skill in the art is familiar with possible formulations and uses of depot injections.

Regarding antibodies, in an exemplary embodiment an antibody or antibody fragment of the present disclosure is stored at 10 mg/ml in sterile isotonic aqueous saline solution for injection at 4° C. and is diluted in either 100 ml or 200 ml 0.9% sodium chloride for injection prior to administration to the subject. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via subcutaneous bolus injection.

Combination Therapy

The present disclosure contemplates the use of the Modulators (e.g., Polypeptides) in combination with one or more active therapeutic agents or other prophylactic or therapeutic modalities. In such combination therapy, the various active agents frequently have different mechanisms of action. Such combination therapy may be especially advantageous by allowing a dose reduction of one or more of the agents, thereby reducing or eliminating the adverse effects associated with one or more of the agents; furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the Modulators are administered or applied sequentially, e.g., where one agent is administered prior to one or more other agents. In other embodiments, the Modulators are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The Modulators of the present disclosure can be used in combination with other agents useful in the treatment, prevention, suppression or amelioration of the diseases, disorders or conditions set forth herein, including those that are normally administered to subjects suffering from hyperglycemia, hyperinsulinemia, glucose intolerance, and other glucose metabolism disorders.

The present disclosure contemplates combination therapy with numerous agents (and classes thereof), including 1) insulin, insulin mimetics and agents that entail stimulation of insulin secretion, including sulfonylureas (e.g., chlorpropamide, tolazamide, acetohexamide, tolbutamide, glyburide, glimepiride, glipizide) and meglitinides (e.g., repaglinide (PRANDIN) and nateglinide (STARLIX)); 2) biguanides (e.g., metformin (GLUCOPHAGE)) and other agents that act by promoting glucose utilization, reducing hepatic glucose production and/or diminishing intestinal glucose output; 3) alpha-glucosidase inhibitors (e.g., acarbose and miglitol) and other agents that slow down carbohydrate digestion and consequently absorption from the gut and reduce postprandial hyperglycemia; 4) thiazolidinediones (e.g., rosiglitazone (AVANDIA), troglitazone (REZULIN), pioglitazone (ACTOS), glipizide, balaglitazone, rivoglitazone, netoglitazone, troglitazone, englitazone, ciglitazone, adaglitazone, darglitazone that enhance insulin action (e.g., by insulin sensitization), thus promoting glucose utilization in peripheral tissues; 5) glucagon-like-peptides including DPP-IV inhibitors (e.g., vildagliptin (GALVUS) and sitagliptin (JANUVIA)) and Glucagon-Like Peptide-1 (GLP-1) and GLP-1 agonists and analogs (e.g., exenatide (BYETTA)); 6) and DPP-IV-resistant analogues (incretin mimetics), PPAR gamma agonists, dual-acting PPAR agonists, pan-acting PPAR agonists, PTP1B inhibitors, SGLT inhibitors, insulin secretagogues, RXR agonists, glycogen synthase kinase-3 inhibitors, immune modulators, beta-3 adrenergic receptor agonists, 11beta-HSD1 inhibitors, and amylin analogues.

Furthermore, the present disclosure contemplates combination therapy with agents and methods for promoting weight loss, such as agents that stimulate metabolism or decrease appetite, and modified diets and/or exercise regimens to promote weight loss.

The Modulators of the present disclosure may be used in combination with one or more other agent in any manner appropriate under the circumstances. In one embodiment, treatment with the at least one active agent and at least one Modulator of the present disclosure is maintained over a period of time. In another embodiment, treatment with the at least one active agent is reduced or discontinued (e.g., when the subject is stable), while treatment with the Modulator of the present disclosure is maintained at a constant dosing regimen. In a further embodiment, treatment with the at least one active agent is reduced or discontinued (e.g., when the subject is stable), while treatment with the Modulator of the present disclosure is reduced (e.g., lower dose, less frequent dosing or shorter treatment regimen). In yet another embodiment, treatment with the at least one active agent is reduced or discontinued (e.g., when the subject is stable), and treatment with the Modulator of the present disclosure is increased (e.g., higher dose, more frequent dosing or longer treatment regimen). In yet another embodiment, treatment with the at least one active agent is maintained and treatment with the Modulator of the present disclosure is reduced or discontinued (e.g., lower dose, less frequent dosing or shorter treatment regimen). In yet another embodiment, treatment with the at least one active agent and treatment with the Modulator of the present disclosure are reduced or discontinued (e.g., lower dose, less frequent dosing or shorter treatment regimen).

Dosing

The Modulators (e.g., Polypeptides) of the present disclosure may be administered to a subject in an amount that is dependent upon, for example, the goal of the administration (e.g., the degree of resolution desired); the age, weight, sex, and health and physical condition of the subject to be treated; the nature of the Modulator, and/or formulation being administered; the route of administration; and the nature of the disease, disorder, condition or symptom thereof (e.g., the severity of the dysregulation of glucose/insulin and the stage of the disorder). The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with absorption, distribution, metabolism, and excretion ("ADME"), taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the Modulators of the present disclosure may be an amount that, when administered in one or more doses to a subject, produces a desired result relative to a healthy subject. For example, an effective dose may be one that, when administered to a subject having elevated plasma glucose and/or plasma insulin, achieves a desired reduction relative to that of a healthy subject by at least about 10%, at least about 20%, at least about 25%, at least about 30%, at least about 40%, at least about 50%, at least about 60%, at least about 70%, at least about 80%, or more than 80%.

An appropriate dosage level will generally be about 0.001 to 100 mg/kg of patient body weight per day, which can be administered in single or multiple doses. In some embodiments, the dosage level will be about 0.01 to about 25 mg/kg per day, and in other embodiments about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient. The Modulators may be administered on a regimen of, for example, 1 to 4 times per day, and often once or twice per day.

The dosage of the Modulators of the present disclosure may be repeated at an appropriate frequency, which may be in the range of once per day to once every three months, depending on the pharmacokinetics of the Modulators (e.g. half-life) and the pharmacodynamic response (e.g. the duration of the therapeutic effect of the Modulator). In some embodiments where the Modulator is an antibody or a fragment thereof, or a polypeptide or variants thereof, dosing is frequently repeated between once per week and once every 3 months. In other embodiments, such Modulators are administered approximately once per month.

In certain embodiments, the dosage of the disclosed Modulators is contained in a "unit dosage form". The phrase "unit dosage form" refers to physically discrete units, each unit containing a predetermined amount of a Modulator of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising the disclosed Modulators (e.g., Polypeptides), and pharmaceutical compositions thereof. The kits are generally in the form of a physical structure housing various components, as described below, and may be utilized, for example, in practicing the methods described above (e.g., administration of a Modulator to a subject in need of restoring glucose homeostasis).

A kit can include one or more of the Modulators disclosed herein (provided in, e.g., a sterile container), which may be in the form of a pharmaceutical composition suitable for administration to a subject. The Modulators can be provided in a form that is ready for use or in a form requiring, for example, reconstitution or dilution prior to administration. When the Modulators are in a form that needs to be reconstituted by a user, the kit may also include buffers, pharmaceutically acceptable excipients, and the like, packaged with or separately from the Modulators. When combination therapy is contemplated, the kit may contain the several agents separately or they may already be combined in the kit. Each component of the kit can be enclosed within an individual container and all of the various containers can be within a single package. A kit of the present disclosure can be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampoule, tube or vial). Exemplary instructions include those for reducing or lowering blood glucose, treatment of hyperglycemia, treatment of diabetes, etc. with the disclosed Modulators, and pharmaceutical compositions thereof Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); ng=nanogram; µg=microgram; mg= milligram; g=gram; kg=kilogram; dl or dL=deciliter; µl or µL=microliter; ml or mL=milliliter; l or L=liter; µM=micromolar; mM=millimolar; M=molar; kDa= kilodalton; i.m.=intramuscular(ly); i.p.=intraperitoneal(ly); s.c.= subcutaneous(ly); bid=twice daily; HPLC=high performance liquid chromatography; BW=body weight; U=unit; ns=not statistically significant; PG=fasting plasma glucose; FPI=fasting plasma insulin; ITT=insulin tolerance test; PTT=pyruvate tolerance test; oGTT=oral glucose tolerance test; GSIS=glucose-stimulated insulin secretion; PBS=phosphate-buffered saline; PCR=polymerase chain reaction; NHS=N-Hydroxysuccinimide; DMEM=Dulbeco's Modification of Eagle's Medium; GC=genome copy; EDTA=ethylenediaminetetraacetic acid.

Materials and Methods

The following methods and materials were used in the Examples below:

Animals.

Diet-induced obese (DIO) male C57BL/6J mice (The Jackson Laboratory, Bar Harbor, Me.) were maintained on a high-fat diet (D12492, Research Diets, Inc, New Brunswick, N.J.) containing 60 kcal % fat, 20 kcal % protein and 20 kcal % carbohydrate for 12-20 weeks. All animal studies were approved by the NGM Institutional Animal Care and Use Committee.

Nine-week old male B6. V-LEP$^{ob}$/J (leptin-deficient (ob/ob)) mice (The Jackson Laboratory, Bar Harbor, Me.) were used in the recombinant doing studies. Mice had free access to autoclaved distilled water and were fed ad libitum a commercial mouse chow (Irradiated 2018 Teklad Global 18% protein Rodent Diet, Harlan Laboratories, Dublin, Va.). All animal studies were approved by the NGM Institutional Animal Care and Use Committee.

Nucleic Acid and Amino Acid Sequences.

GenBank Accession No. BC000529.2 sets forth the cDNA of ORF encoding human GDF15, and GenBank Accession No. NP_004855.2 sets forth the amino acid sequence encoded by the cDNA. The 112-amino acid GDF15 (FIG. 1B), or a GDF15 mutein, was used.

GDF15 ORF was amplified with polymerase chain reaction (PCR) using a recombinant DNA (cDNA) clone purchased from Open Biosystems (Cat. # MHS1011-58735). PCR reagents kits with Phusion high-fidelity DNA polymerase were purchased from New England BioLabs (F-530L, Ipswich, Mass.). The following primers were used: forward PCR primer: 5' TGCTCTAGAATGCCCGGGCAAG (SEQ ID NO:38) and reverse PCR primer: 5' CCATCGATCTAT-CATATGCAGTGGCA (SEQ ID NO:39).

Amplified DNA fragment was digested with restriction enzymes Xba I and ClaI (the restriction sites were included in the 5' (Xba I) and 3' (Cla I) PCR primers, respectively) and was then ligated with AAV transgene vectors that had been digested with the same restriction enzymes. The vector used for expression contained a selectable marker and an expression cassette composed of a strong eukaryotic promoter 5' of a site for insertion of the cloned coding sequence, followed by a 3' untranslated region and bovine growth hormone polyadenylation tail. The expression construct is also flanked by internal terminal repeats at the 5' and 3' ends.

Production and Purification of AAV.

293 cells (Agilent Technologies, Santa Clara, Calif.) were cultured in DMEM (Mediatech, Inc., Manassas, Va.) supplemented with 10% fetal bovine serum and 1× antibiotic-antimycotic solution (Mediatech, Inc., Manassas, Va.). On day 1, the cells were plated at 50% density in 150 mm cell culture plates. On day 2, the cells were transfected using calcium phosphate precipitation method with the following 3 plasmids (20 µg/plate of each): AAV transgene plasmid, pHelper plasmids (Agilent Technologies, Santa Clara, Calif.) and AAV2/9 plasmid (Gao et al., J. Virol. 78:6381 (2004)).

Forty-eight hours after transfection, the cells were scraped off the plates, pelleted by centrifugation at 3000×g and re-suspended in buffer containing 20 mM Tris pH 8.5, 100 mM NaCl and 1 mM MgCl$_2$. The suspension was frozen in an alcohol dry ice bath and was then thawed in a 37° C. water bath; the freeze and thaw cycles were repeated three times. Benzenase (Sigma-aldrich, St. Louis, Mo.) was added to a final concentration of 50 units/ml, and deoxycholate was added to a final concentration of 0.25%. After incubation at 37° C. for 30 min, cell debris was pelleted by centrifugation at 5000×g for 20 min. Viral particles in the supernatant were purified using a iodixanal (Sigma-aldrich, St. Louis, Mo. (discontinued)) gradient as previously described (Zolotukhin et al., Gene Ther. 6:973 (1999)). The viral stock was concentrated using Vivaspin 20 (MW cutoff 100,000 Dalton, Sartorius Stedim Biotech, Aubagne, France) and re-suspended in PBS with 10% glycerol and stored at −80° C. To determine the viral genome copy number, 2 µl of viral stock were incubated in 6 µl of solution containing 50 units/ml Benzonase, 50 mM Tris-HCl pH 7.5, 10 mM MgCl$_2$ and 10 mM CaCl$_2$ at 37° C. for 30 minutes.

Thereafter, 15 µl of a solution containing 2 mg/ml of Proteinase K, 0.5% SDS and 25 mM EDTA were added and the mixture was incubated for an additional 20 min at 55° C. to release viral DNA. Viral DNA was cleaned with mini DNeasy Kit (Qiagen, Valencia, Calif.) and eluted with 40 µl of water. Viral GC was determined using quantitative PCR. Viral stock was diluted with PBS to desirable GC/ml. Viral working solution (200 µl) was delivered into mice via tail vein injection.

Blood Glucose Assay.

Blood glucose from mouse tail snip was measured using ACCU-CHEK Active test strips read by ACCU-CHEK Active meter (Roche Diagnostics, Indianapolis, Ind.) following manufacturer's instruction.

Serum GDF15 Variants Exposure Level Assay.

Whole blood (~50 µl/mouse) from mouse tail snips was collected into plain capillary tubes (BD Clay Adams SurePrep, Becton Dickenson, Sparks, Md.). Serum and blood cells were separated by spinning the tubes in an Autocrit Ultra 3 (Becton Dickinson, Sparks, Md.). GDF15 exposure levels in serum were determined using Human GDF-15 Quantikine ELISA Kit (R&D Systems, Minneapolis, Minn.) by following the manufacturer's instructions.

Pegylation of GDF15 Muteins.

NHS-specific chemistries were used to modify recombinant GDF15 muteins, at the N-terminus and/or internally in a site-specific manner, with a linear 10 kDa PEG moiety (Nanocs Inc.; New York, N.Y.; cat. no. PG1-SC-10k). When desired, prevention of PEGylation at the N-terminal alanine was effected using sulfo-NHS-acetate (Thermo Fisher Scientific; Waltham, Mass.; cat. no. 26777). Labeling reactions were followed as per manufacturer's instructions, and excess label was quenched using a 1/100 (v/v) addition of 1M Tris pH 8.0.

Example 1: Effects of GDF15 on Body Weight and Fasted Blood Glucose in High-Fat Fed Diet Induced Obesity (DIO) Mice To evaluate the effect of continuous GDF15 exposure on body weight and fasted glucose serum levels, 19-week old high-fat fed, DIO mice (n=7) weighing approximately 45 g and having four-hour fasted glucose serum levels of approximately 237 mg/dl, received a single bolus tail vein injection of AAV virus containing the above-described GDF15 gene insert. Serum systemic exposure was monitored by Human GDF-15 Quantikine ELISA Kit (R&D Systems, Minneapolis, Minn.) following the manufacturer's instructions (FIG. 3). The data in FIG. 3 demonstrate systemic exposure levels of GDF15 in mice from genetic methods in order to establish a clear relationship of observed phenotype compared to GDF15 serum concentration (see FIGS. 4-7). Using these exposure levels as a benchmark, mice in Example 3 were administered recombinant GDF15 at doses that attained approximately equivalent serum level concentrations to those observed via genetic validation.

Figure 4:
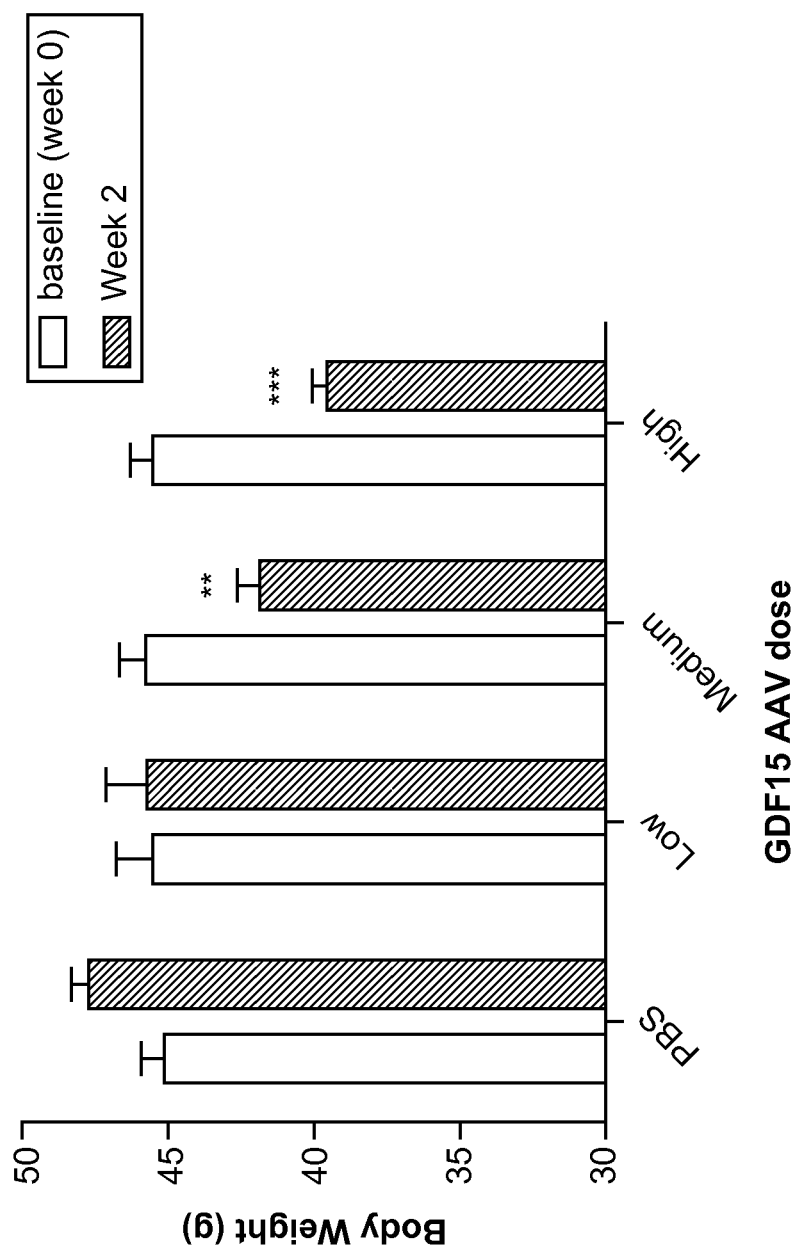
FIG. 4 depicts the effect on weight reduction in DIO mice prior to (unshaded bars) and following two weeks (shaded bars) of systemic delivery of GDF15. For AAV dosing, Low=0.7 ng/mL, Medium=14.9 ng/mL, and High=65.5 ng/mL. In each group of mice, n=7 and p-values (*, $p<0.05$; , $p<0.01$; *, $p<0.001$) were determined by 2-way ANOVA comparing body weight at week 2 following GDF15 dosing and PBS vehicle-control dosing.

As depicted in FIG. 4, systemic exposure of GDF15 for 2 weeks significantly decreased body weight at serum concentrations above 14.9 ng/mL. Following 2 weeks of systemic exposure, body weight decreases of 5.9 g comprising a 12.4% decrease (, $p<0.01$) and 8.2 g comprising a 17.3% decrease (*, $p<0.001$) were observed for medium (14.9 ng/mL) and high (65.6 ng/mL) exposures respectively, relative to PBS-injected DIO mice at week 2. In each group of mice, n=7 and p-values were determined by 2-way ANOVA comparing body weight at week 2 with PBS vehicle control (average body weight=47.7 g).

Figure 5:
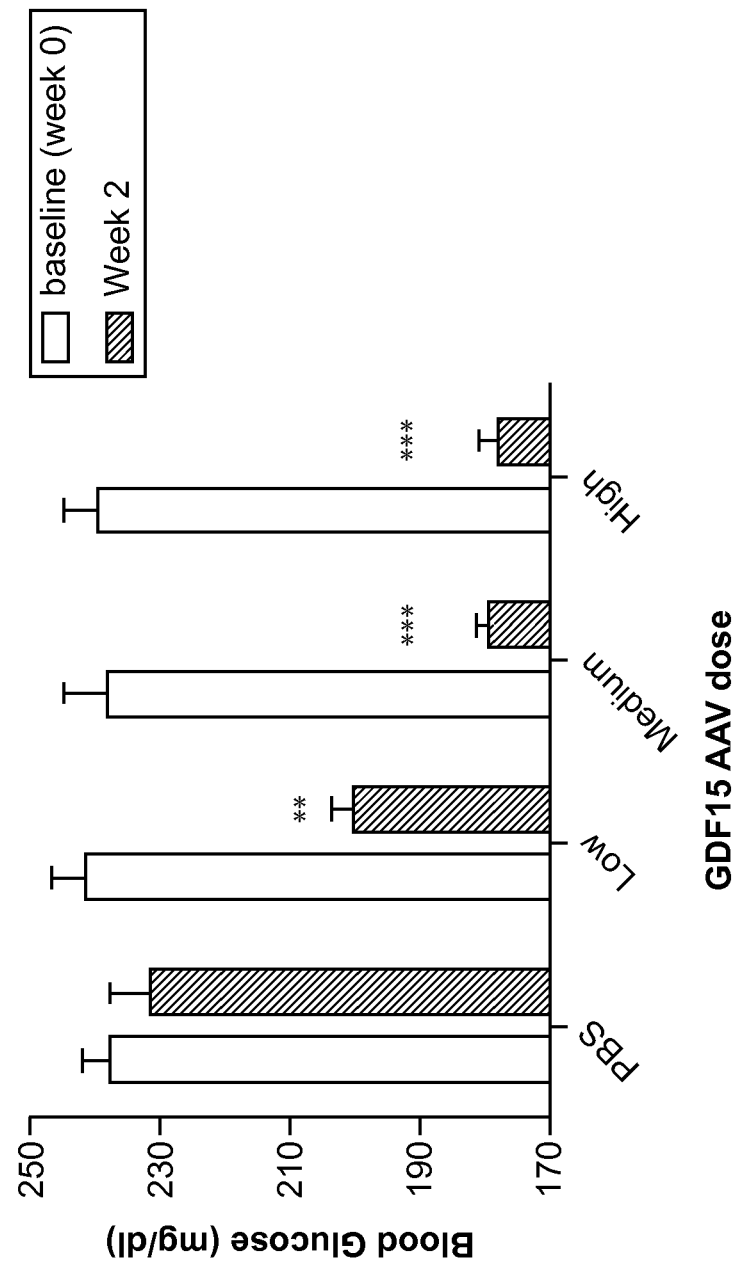
FIG. 5 depicts the effect on blood glucose, measured after four hours of fasting, of DIO mice prior to (unshaded bars) and following two weeks (shaded bars) of systemic delivery of GDF15. For AAV dosing, Low=0.7 ng/mL, Medium=14.9 ng/mL, and High=65.5 ng/mL. In each group of mice, n=7 and and p-values (*, p<0.05; , p<0.01; *, p<0.001) were determined by 1-way ANOVA comparing blood glucose at week 2 following GDF15 dosing and PBS vehicle-control dosing.

As depicted in FIG. 5, systemic exposure of GDF15 for 2 weeks significantly decreased fasted serum glucose levels at all systemic serum concentrations of GDF15. Following two weeks of systemic exposure, 4-hour fasted blood glucose level decreases of 31.3 mg/dl comprising a 13.5% decrease (, $p<0.01$), 52.0 mg/dl comprising a 22.5% decrease (*, $p<0.001$), and 53.3 mg/dl comprising a 23.0% decrease (***, $p<0.001$) were observed for low (0.7 ng/mL), medium (14.9 ng/mL) and high (65.6 ng/mL) exposures, respectively, relative to PBS-injected DIO mice at week 2. In each group of mice, n=7 and p-values were determined by 1-way ANOVA comparing body weight at week 2 compared to PBS vehicle control (average serum glucose level=231.3 mg/dl).

Example 2: Systemic Exposure Effects of GDF15 Muteins on Body Weight and Fasted Blood Glucose in High-Fat Fed Diet-Induced Obese Mice To evaluate the effect of GDF15 muteins on body weight and fasted glucose serum levels, 19-week old high-fat fed, DIO mice (weighing ~41 g and having 4-hour fasted glucose serum levels of ~218 mg/dl) received a single bolus tail vein injection of medium dose AAV (14.9 ng/mL) containing the GDF15 mutein gene insert described above. Systemic serum exposures at were approximated to be equivalent to those of GDF15 at medium dose as set forth in FIG. 3.

Figure 6:
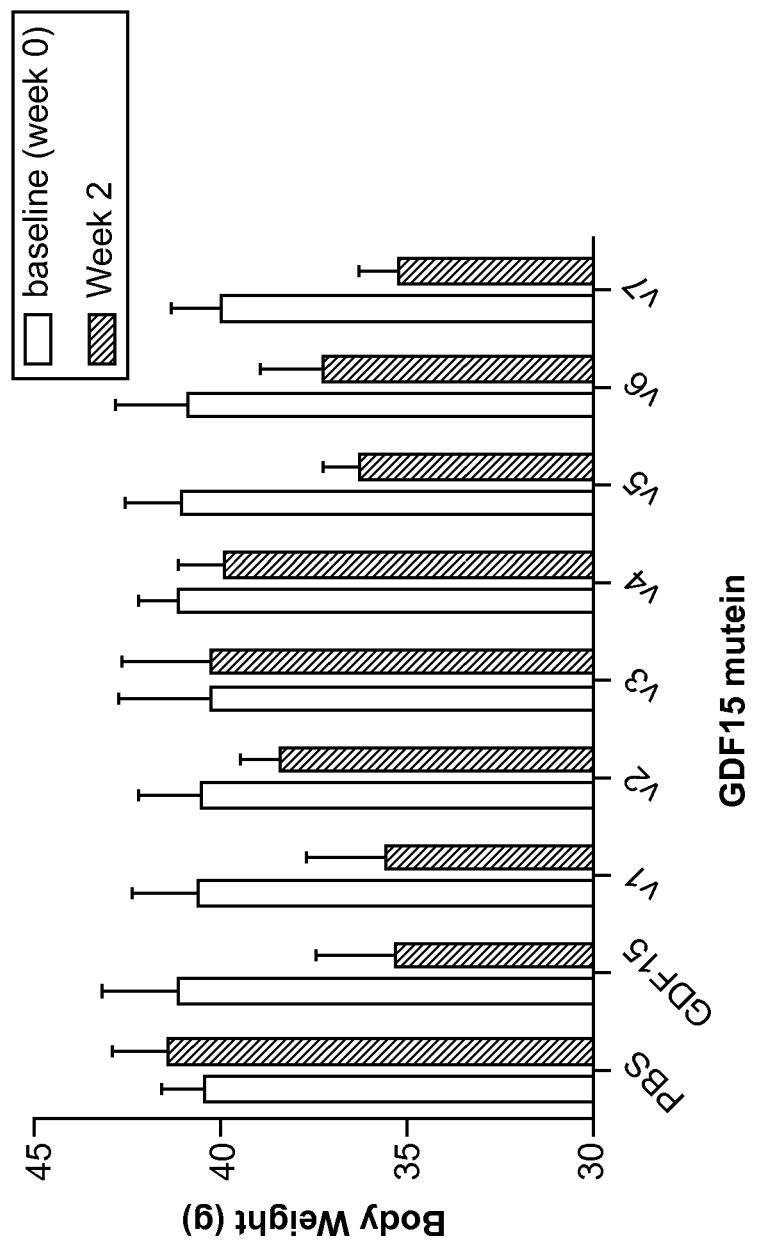
FIG. 6 depicts the effect of GDF15 muteins (v1, v2, v3, v4, v5, v6 and v7; see FIG. 2) on body weight reduction in DIO mice prior to (unshaded bars) and following two weeks (shaded bars) of systemic delivery of GDF15 at Medium (14.9 ng/mL) AAV dosing. In each group of mice, n=5 and p-values were determined by 1-way ANOVA comparing body weight at week 2 following GDF15 mutein dosing and PBS vehicle-control dosing; ns=not significant.

As depicted in FIG. 6, systemic exposure of GDF15 muteins for 2 weeks resulted in decreased body weight trends at medium AAV dose. Following 2 weeks of systemic exposure, body weight decreases, relative to PBS-injected DIO mice at week 2, were as follows: GDF15 decrease of 6.1 g (ns), v1 decrease of 5.9 g (ns), v2 decrease of 3.0 g (ns), v3 decrease of 1.1 g (ns), v4 decrease of 1.5 g (ns), v5 decrease of 5.2 g (ns), v6 decrease of 5.3 g (ns) and v7 decrease of 6.2 g (ns). In each group of mice, n=5 and p-values were determined by 1-way ANOVA comparing body weight at week 2 following GDF15 mutein dosing with PBS vehicle-control dosing (average body weight=41.4 g).

Figure 7:
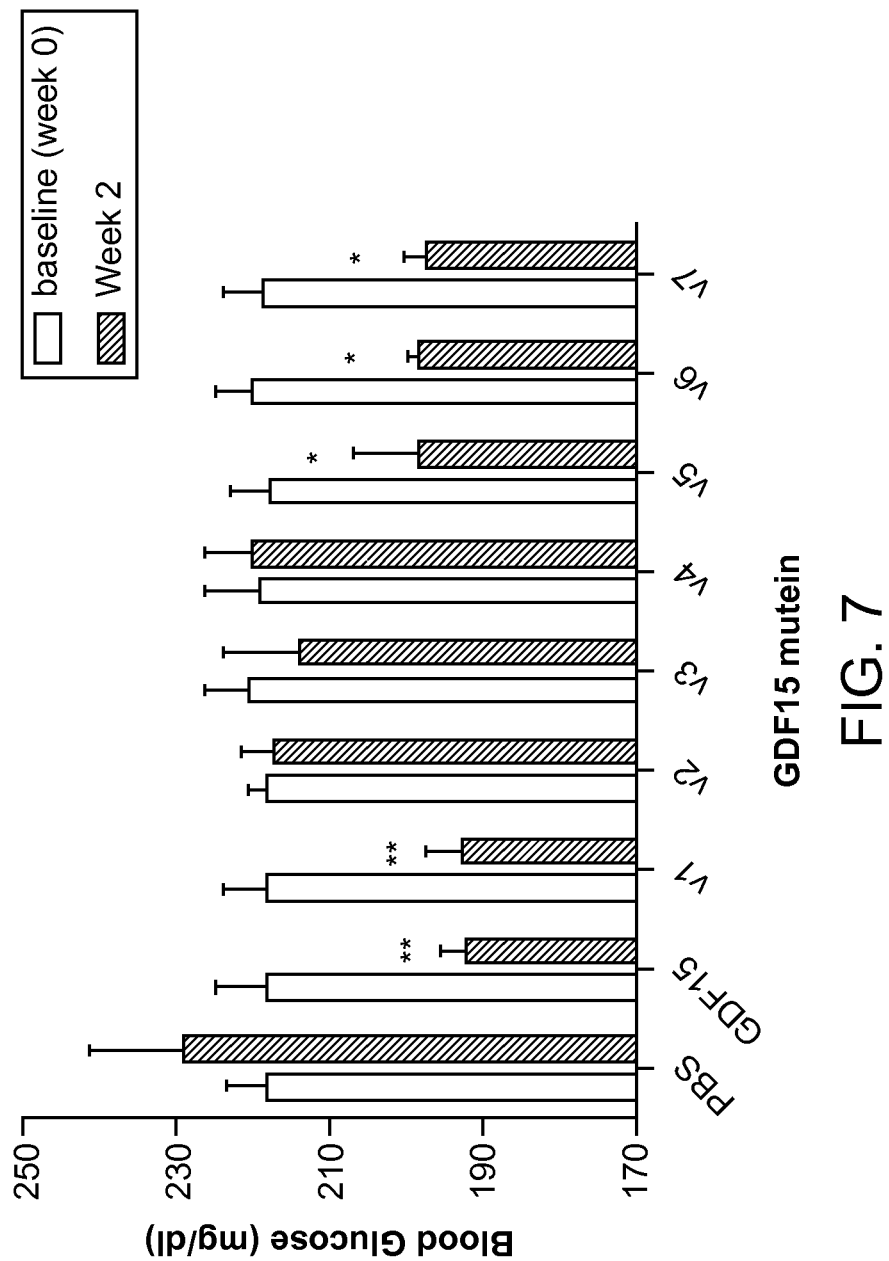
FIG. 7 depicts the effect of GDF15 muteins (v1, v2, v3, v4, v5, v6 and v7; see FIG. 2) on fasted serum blood glucose reduction in DIO mice prior to (unshaded bars) and following two weeks (shaded bars) of systemic delivery of GDF15 at Medium (14.9 ng/mL) AAV dosing. In each group of mice, n=5 and and p-values (*, p<0.05; , p<0.01; *, p<0.001) were determined by 1-way ANOVA comparing four-hour fasted serum blood glucose at week 2 following GDF15 dosing and PBS vehicle-control dosing; ns=not significant.
Figure 8:
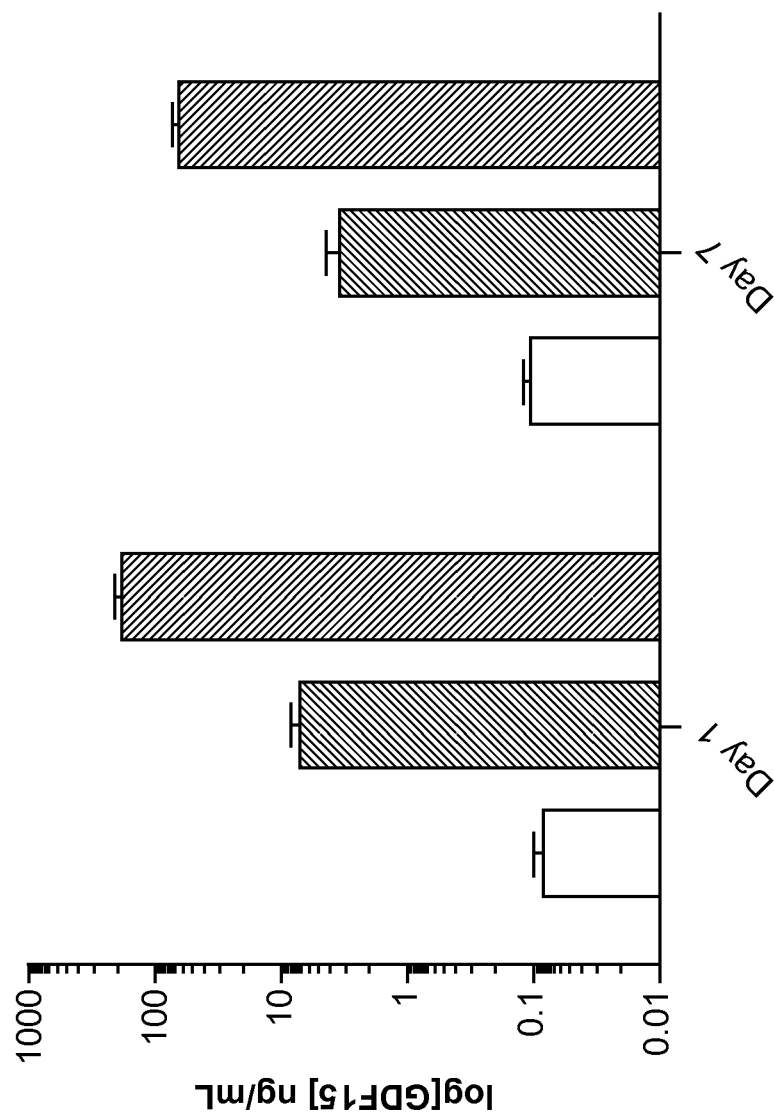
FIG. 8 depicts the dose-dependent serum exposure of recombinant GDF15, administered twice daily s.c., in 8-week old ob/ob mice (three dosing groups, n=7 per dosing group) on day 1 and day 7. On day one, the first dosing group received (w/w equivalent) 0.02 mg/kg, the second dosing group received 0.2 mg/kg, and the third dosing group received 2 mg/kg; the serum exposure (measured four hours after administration of the last (second) daily dose) is represented by the unshaded bar (first dosing group), grey shaded bar (second dosing group), and black shaded bar (third dosing group). From day 2 to day 7, the first dosing group received (w/w equivalent) 0.01 mg/kg twice daily, the second dosing group received 0.1 mg/kg twice daily, and the third dosing group received 1 mg/kg twice daily; the serum exposure (measured four hours after administration of the last (second) dose on day 7) is represented by the unshaded bar (first dosing group), grey shaded bar (second dosing group), and black shaded bar (third dosing group).

As depicted in FIG. 7, systemic exposure of GDF15 muteins for 2 weeks significantly decreased fasted serum glucose levels at medium AAV dose. Following two weeks of systemic exposure, 4-hour fasted serum glucose levels, relative to PBS-injected DIO mice at week 2, were as follows: GDF15 decrease of 37 mg/dl (, $p<0.01$), v1 decrease of 36.6 mg/dl (, $p<0.01$), v2 decrease of 11.8 mg/dl (ns), v3 decrease of 15.3 mg/dl (ns), v4 decrease of 9.2 mg/dl (ns), v5 decrease of 30.8 mg/dl (*, $p<0.05$), v6 decrease of 31 mg/dl (*, $p<0.05$) and v7 decrease of 31.8 mg/dl (*, $p<0.05$). In each group of mice, n=5 and p-values were determined by 1-way ANOVA comparing four-hour fasted serum blood glucose at week 2 following GDF15 mutein dosing with PBS vehicle-control dosing (average blood glucose=229.2 mg/dl).

Example 3: Effect of Recombinant GDF15 on Food Intake, Body Weight and Non-Fasted Blood Glucose in Leptin-Deficient Ob/Ob Mice To evaluate the effect of dose-dependent recombinant GDF15 exposure on food intake, body weight and fasted glucose serum levels, 9-week old ob/ob mice (three dosing groups, n=7 per group) weighing approximately 44.5 g (average of all dosing groups) and having non-fasted glucose serum levels of approximately 393.6 mg/dl (average of all dosing groups), received recombinant GDF15 via s.c. bid delivery. Serum GDF15 exposure was monitored by Human GDF-15 Quantikine ELISA Kit (R&D Systems, Minneapolis, Minn.) following the manufacturer's instructions.

On day one, the first dosing group received (w/w equivalent) 0.02 mg/kg, the second dosing group received 0.2 mg/kg, and the third dosing group received 2 mg/kg. Referring to FIG. 8, the serum exposure (measured four hours after administration of the last (second) dose) is represented by the unshaded bar (first dosing group), grey shaded bar (second dosing group), and black shaded bar (highest dosing group). From day 2 to day 7, the first dosing group received (w/w equivalent) 0.01 mg/kg twice daily, the second dosing group received 0.1 mg/kg twice daily, and the third dosing group received 1 mg/kg twice daily; the serum exposure (measured four hours after administration of the last (second) dose on day 7) is represented by the unshaded bar (first dosing group), grey shaded bar (second dosing group), and black shaded bar (third dosing group).

As indicated in FIG. 8, exposure to recombinant GDF15 was within the equivalent range (ng/mL) of that established in Example 1 (see FIG. 3). These data establish a correlation of equivalency between serum GDF15 levels and body weight and blood glucose phenotypes for both the genetic and the recombinant GDF15 modalities.

The dose-dependent effect of recombinant GDF15 on food intake (grams/day/animal) was then determined during the course of one week of twice-daily s.c. dosing. On day one, singly housed mice were fasted in the morning and the first dosing group received (w/w equivalent) 0.02 mg/kg, the second dosing group received 0.2 mg/kg, and the third dosing group received 2 mg/kg. Eight hours later this dosing regimen was repeated. Thereafter, food was returned back to the animal cages. On the morning of day 2, the remaining food was weighed and each animal's overnight ("0/N") food intake was calculated. For day 2 to day 7, the first dosing group received (w/w equivalent) 0.01 mg/kg, the second dosing group received 0.1 mg/kg and the third dosing group received 1 mg/kg. Each animal's food intake from day 2 to day 4 and from day 4 to day 7 was again measured. The food intake measurement from day 2 to day 7 was made prior to each day's dose.

Figure 9:
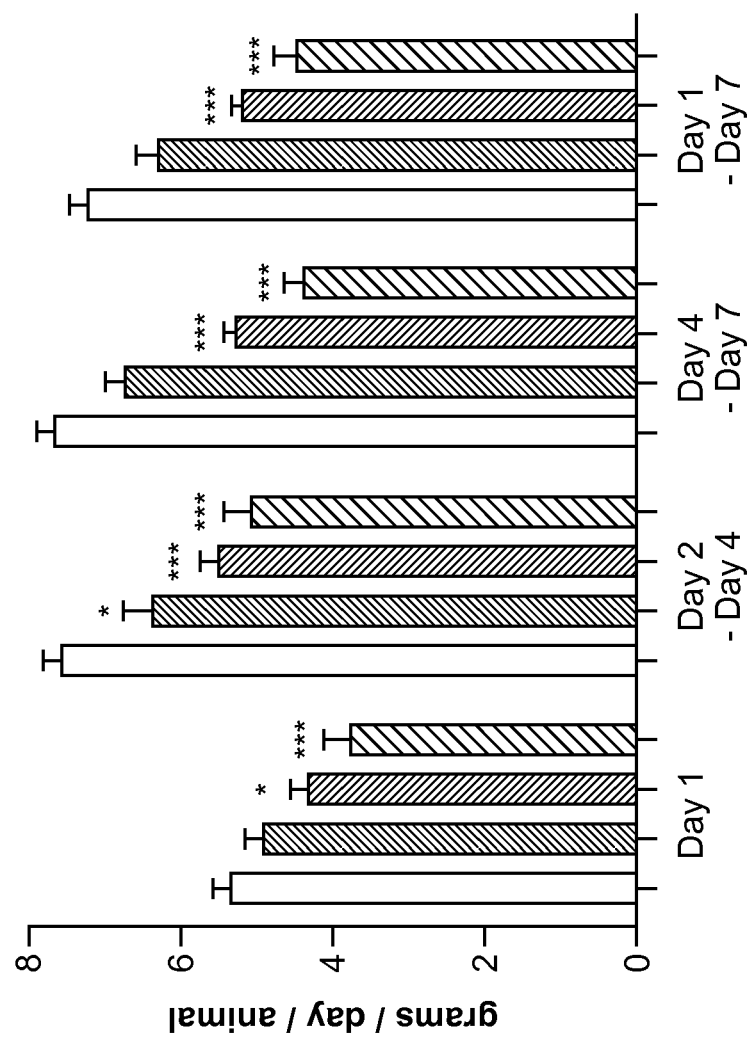
FIG. 9 depicts the dose-dependent effect of recombinant GDF15 on food intake (grams/day/animal) in ob/ob mice during the course of one week of twice-daily s.c. dosing. On day one, singly housed animals were fasted in the morning and the first dosing group received (w/w equivalent) 0.02 mg/kg, the second dosing group received 0.2 mg/kg, and the third dosing group received 2 mg/kg. Eight hours later, this dosing regmine was repeated and, thereafter, food was returned to the animal cages. On the morning of day 2, leftover food was weighed and each animal's overnight (0/N) food intake was calculated. For day 2 to day 7, the first dosing group received (w/w equivalent) 0.01 mg/kg, the second dosing group received 0.1 mg/kg and the third dosing group received 1 mg/kg. Each animal's accumulated food intake from day 2 to day 4 and from day 4 to day 7 were again measured. Food intake in vehicle control animals is represented by the unshaded bars, while the effect on food intake on the first dosing group is represented by the light grey shaded bars, on the second dosing group is represented by the medium grey shaded bars, and on the third dosing group is represented by the black shaded bars. In each dosing group, n=7 and and p-values (*, p<0.05; , p<0.01; *, p<0.001) were determined by 2-way ANOVA comparing food intake at each time point with vehicle control.

Referring to FIG. 9, food intake in vehicle-control animals is represented by the unshaded bars, while the effect on food intake on the first dosing group is represented by the light-grey shaded bars, on the second dosing group is represented by the medium-grey shaded bars, and on the third dosing group is represented by the black shaded bars. As depicted in FIG. 9, recombinant GDF15 significantly decreased food intake relative to vehicle control-injected ob/ob mice at days 1, 4 and 7. For day 1, food intake was as follows: vehicle control dosing group=5.3 g, first dosing group=4.9 g (ns), second dosing group=4.3 g (*, p<0.05) and third dosing group=3.7 g (***, p<0.001). For day 2 to day 4, food intake was as follows: vehicle control dosing group=7.6 g; first dosing group=6.4 g (*, p<0.05); second dosing group=5.5 g (*, p<0.001); and third dosing group=3.7 g (*, p<0.001). For day 4 to day 7, food intake was as follows: vehicle control dosing group=7.7 g; first dosing group=6.7 g (ns); second dosing group=5.3 g (*, p<0.001); and third dosing group=4.3 g (*, p<0.001). The average food intake (grams/day/animal) for the duration of the experiment for all time points (days 1-7) was as follows: vehicle control dosing group=7.2 g; first dosing group=6.3 g (ns); second dosing group=5.2 g (*, p<0.001); and third dosing group=4.5 g (*, p<0.001). In each group of mice, n=7 and p-values were determined by 2-way ANOVA comparing food intake at each time point compared to vehicle control.

Figure 10:
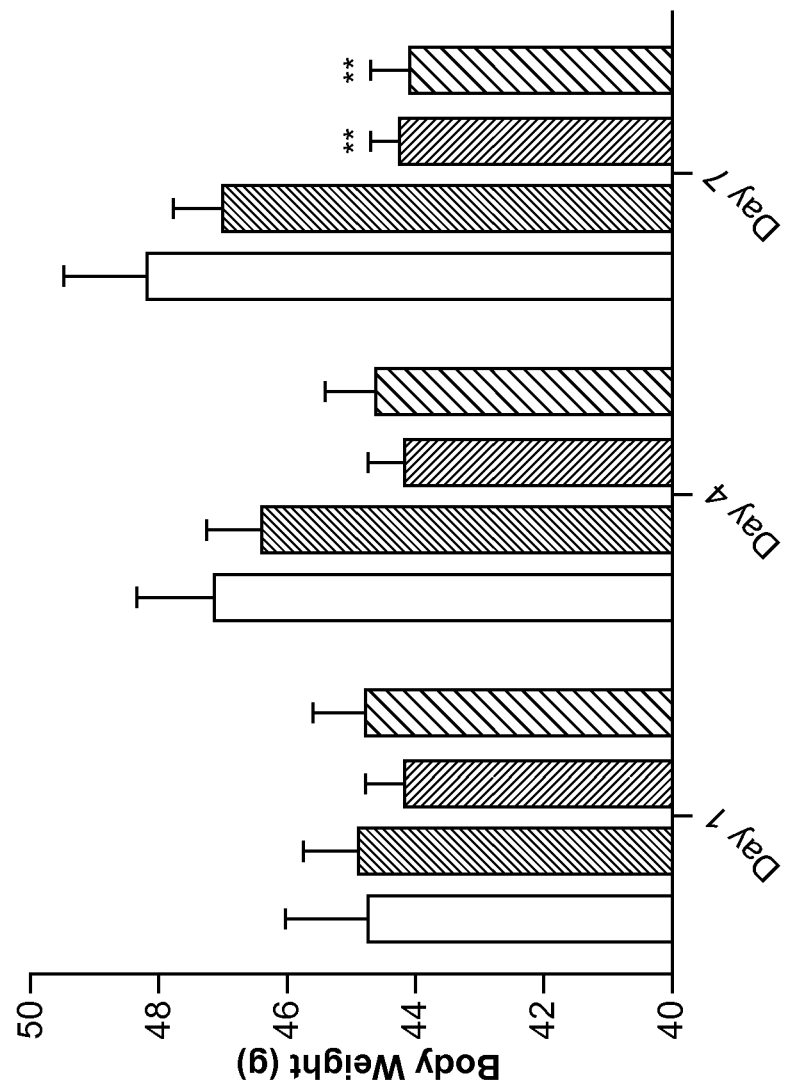
FIG. 10 depicts the dose-dependent effect of twice daily s.c. dosing of recombinant GDF15 on body weight (grams) in ob/ob mice at day 1, day 4 and day 7. On day one, the first dosing group received (w/w equivalent) 0.02 mg/kg, the second dosing group received 0.2 mg/kg, and the third dosing group received 2 mg/kg. For day 2 to day 7, the first dosing group received (w/w equivalent) 0.01 mg/kg, the second dosing group received 0.1 mg/kg and the third dosing group received 1 mg/kg. On each day, body weight was recorded prior to the morning dose. Body weight in vehicle control animals is represented by the unshaded bars, while the effect of GDF15 on body weight in the first dosing group is represented by the light grey shaded bars, in the second dosing group is represented by the medium grey shaded bars, and in the third dosing group is represented by the black shaded bars. In each dosing group, n=7 and and p-values (*, p<0.05; , p<0.01; *, p<0.001) were determined by 2-way ANOVA comparing food intake at each time point with vehicle control.

As depicted in FIG. 10, mice injected with recombinant GDF15 bid s.c. demonstrated significantly decreased body weight compared to vehicle control-injected ob/ob mice at days 1, 4 and 7. On day one, the first dosing group received (w/w equivalent) 0.02 mg/kg, the second dosing group received 0.2 mg/kg, and the third dosing group received 2 mg/kg. For day 2 to day 7, the first dosing group received (w/w equivalent) 0.01 mg/kg, the second dosing group received 0.1 mg/kg and the third dosing group received 1 mg/kg. On each day, body weight was recorded prior to the morning dose.

For day 1, body weight was as follows: vehicle-control dosing group=44.8 g; first dosing group=44.9 g (ns); second dosing group=44.2 g (ns); and third dosing group=44.7 g (ns). For day 4, body weight was as follows: vehicle-control dosing group=47.1 g; first dosing group=46.4 g (ns); second dosing group=44.2 g (ns); and third dosing group=44.6 g (ns). For day 7, body weight was as follows: vehicle-control dosing group=48.2 g; first dosing group=47.0 g (ns); second dosing group=44.2 g (, p<0.01); and third dosing group=44.0 g (, p<0.01). In each group of mice, n=7 and p-values were determined by 2-way ANOVA comparing body weight at each time point compared to vehicle control.

Figure 11:
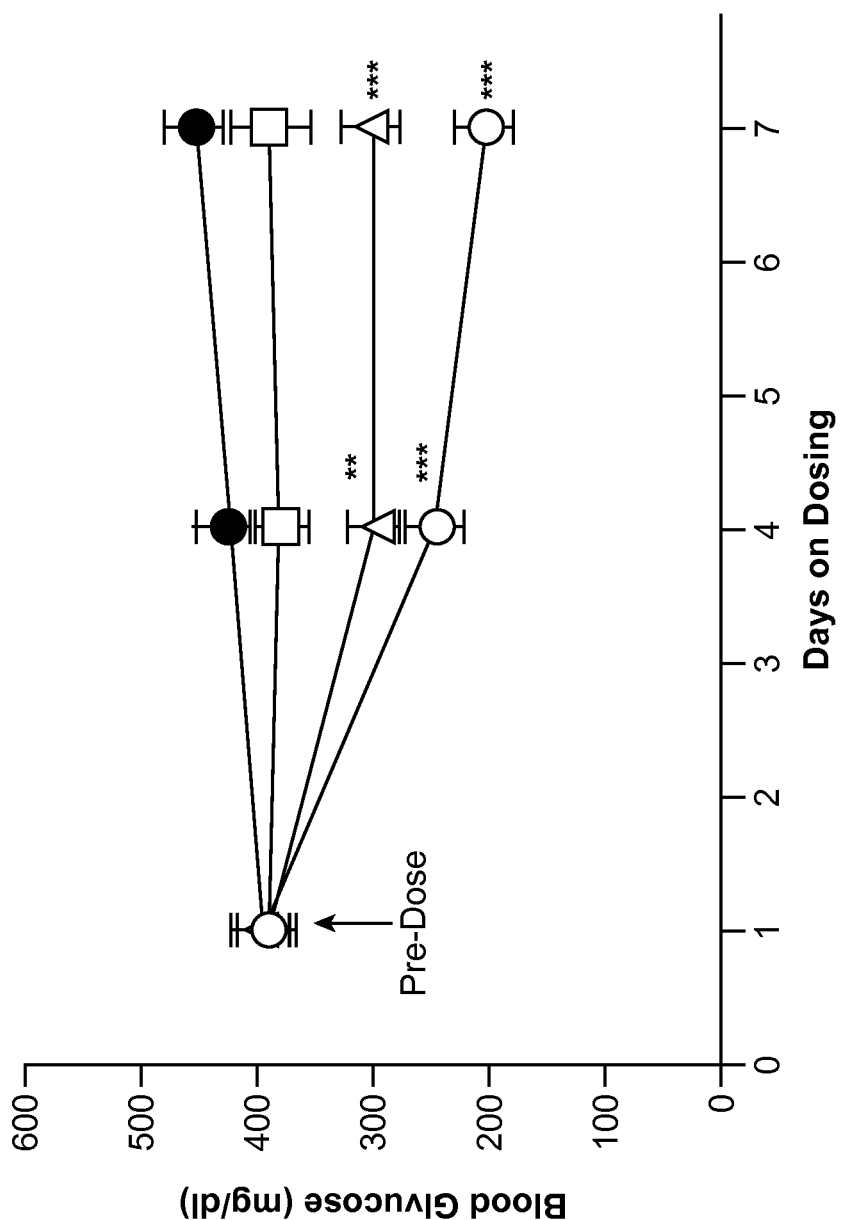
FIG. 11 depicts the dose-dependent effect of recombinant GDF15, administered s.c. twice daily, on non-fasted blood glucose measured 16 hours post-dose in ob/ob mice. On day one, mice were injected with vehicle (shaded circles), 0.02 mg/kg (first dosing group; shaded squares), 0.2 mg/kg (second dosing group; shaded triangles) or 2 mg/kg (third dosing group; unshaded circles). For day 2 to day 7, the first dosing group received (w/w equivalent) 0.01 mg/kg, the second dosing group received 0.1 mg/kg and the third dosing group received 1 mg/kg. At days 4 and 7, the second and third dosing groups exhibited significantly decreased non-fasted blood glucose serum levels (mg/dl) relative to vehicle control-injected levels. In each group of mice, n=7 and p-values (*, p<0.05; , p<0.01; *, p<0.001) were determined by 2-way ANOVA comparing non-fasted blood glucose at each time point with vehicle control.

As depicted in FIG. 11, s.c. bid exposure of recombinant GDF15 resulted in significantly decreased non-fasted blood glucose serum levels 16 hours post-dose relative to vehicle control-injected ob/ob mice at days 4 and 7. Mice were injected with vehicle (shaded circles), 0.02 mg/kg (first dosing group; shaded squares), 0.2 mg/kg (second dosing group; shaded triangles) or 2 mg/kg (third dosing group; unshaded circles). For day 2 to day 7, the first dosing group received (w/w equivalent) 0.01 mg/kg, the second dosing group received 0.1 mg/kg and the third dosing group received 1 mg/kg. At days 4 and 7, the second and third dosing groups exhibited significantly decreased non-fasted blood glucose serum levels (mg/dl) relative to vehicle control-injected levels. For day 1, glucose levels were as follows: vehicle control=392.4 mg/dl; first dosing group=395.0 mg/dl (ns); second dosing group=395.4 mg/dl (ns); and third dosing group=391.7 mg/dl (ns). For day 4, glucose levels were as follows: vehicle control=422.1 mg/dl; first dosing group=381.3 mg/dl (ns); second dosing group=301.9 mg/dl (, p<0.01); and third dosing group=247.7 mg/dl (*, p<0.001). For day 7, glucose levels were as follows: vehicle control=455.6 mg/dl; first dosing group=389.7 mg/dl (ns); second dosing group=304.1 mg/dl (*, p<0.001); and third dosing group=204.7 mg/dl (*, p<0.001). In each group of mice, n=7 and p-values were determined by 2-way ANOVA comparing non-fasted blood glucose at each time point compared to vehicle control.

Example 4: Effect of PEGylated Recombinant GDF15 Muteins on Food Intake and Body Weight in Leptin-Deficient Ob/Ob Mice The effect of recombinant, site-specifically PEGylated GDF15 muteins on food intake and body weight was compared to that of the corresponding non-PEGylated GDF15 muteins. Using the methods described above, variant 1 was PEGylated at the N-terminus (v1-PEG10) (SEQ ID NO:5); variant 5 was PEGylated at lysine69 (v5-PEG10) (SEQ ID NO:9); and variant 6 was PEGylated at lysine91 (v6-PEG10) (SEQ ID NO:10). Ten-week old ob/ob mice received a single s.c. dose of vehicle; non-PEGylated (2 mg/kg) v1, v5 or v6; or PEGylated (2 mg/kg) v1, v5 or v6 (v1-PEG10, v5-PEG10, and v6-PEG10, respectively).

Figure 12:
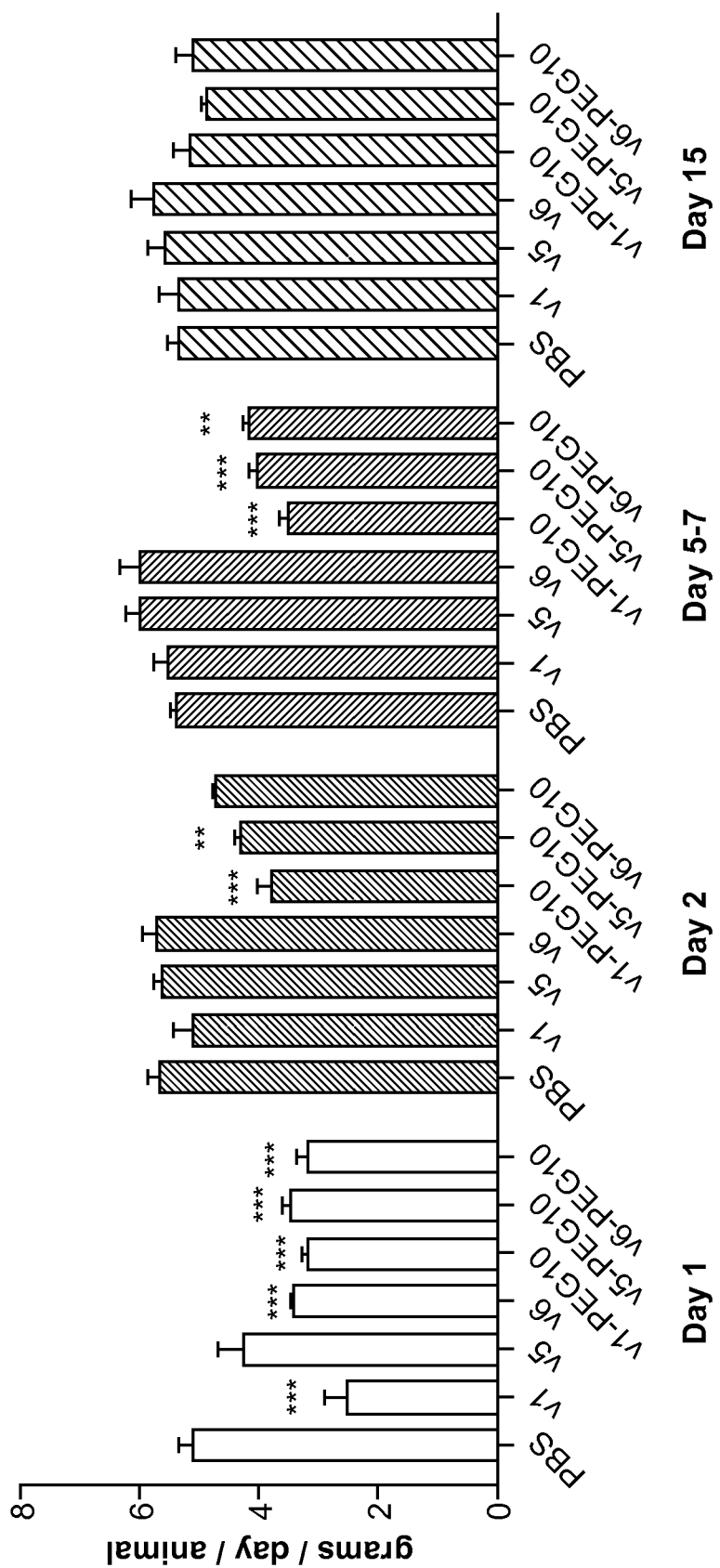
FIG. 12 depicts the effect of recombinant, site-specifically PEGylated GDF15 muteins on food intake compared to that of the corresponding non-PEGylated GDF15 muteins in ob/ob mice. Mice received a single s.c. dose of vehicle; non-PEGylated (2 mg/kg) v1, v5 or v6; or PEGylated (2 mg/kg) v1, v5 or v6 (see FIG. 2). For day 1, food intake (grams/day/animal) was measured 16 hours following dosing, and then on days 2, 5-7 and 15. In each group of mice, n=5, and p-values were determined by one-way ANOVA comparing food intake at each time point with PBS vehicle control.

As depicted in FIG. 12, administration of a single dose of recombinant GDF15 muteins resulted in significantly decreased food intake, relative to vehicle control-injected ob/ob mice, at days 1, 2, 5-7 and 15. For day 1, food intake measured 16 hours following the first dose was follows (grams/day/animal): vehicle control 5.1 g, v1 2.5 g (*, p<0.001), v5 4.3 g (ns), v6 3.4 g (*, p<0.001), v1-PEG10 3.2 g (*, p<0.001), v5-PEG10 3.5 g (*, p<0.001), and v6-PEG10 3.2 g (*, p<0.001). Measurements made during the day 2-day 15 time period were taken at approximately the same time (9:30 a.m.) each day. For day 2, food intake was as follows (grams/day/animal): vehicle control 5.7 g, v1 5.1 g (ns), v5 5.6 g (ns), v6 5.7 g (ns), v1-PEG10 3.8 g (*, p<0.001), v5-PEG10 4.3 g (, p<0.01), and v6-PEG10 4.7 g (ns). For days 5-7, the average daily food intake was as follows (grams/day/animal): vehicle control 5.4 g, v1 5.5 g (ns), v5 6.0 g (ns), v6 6.0 g (ns), v1-PEG10 3.5 g (*, p<0.001), v5-PEG10 4.0 g (*, p<0.001), and v6-PEG10 4.2 g (, p<0.01). For day 15, food intake was as follows (grams/day/animal): vehicle control 5.3 g, v1 5.3 g (ns), v5 5.6 g (ns), v6 5.8 g (ns), v1-PEG10 5.2 g (ns), v5-PEG10 4.9 g (ns), and v6-PEG10 5.1 g (ns). In each group of mice, n=5, and p-values were determined by one-way ANOVA comparing food intake at each time point with PBS vehicle control.

Figure 13:
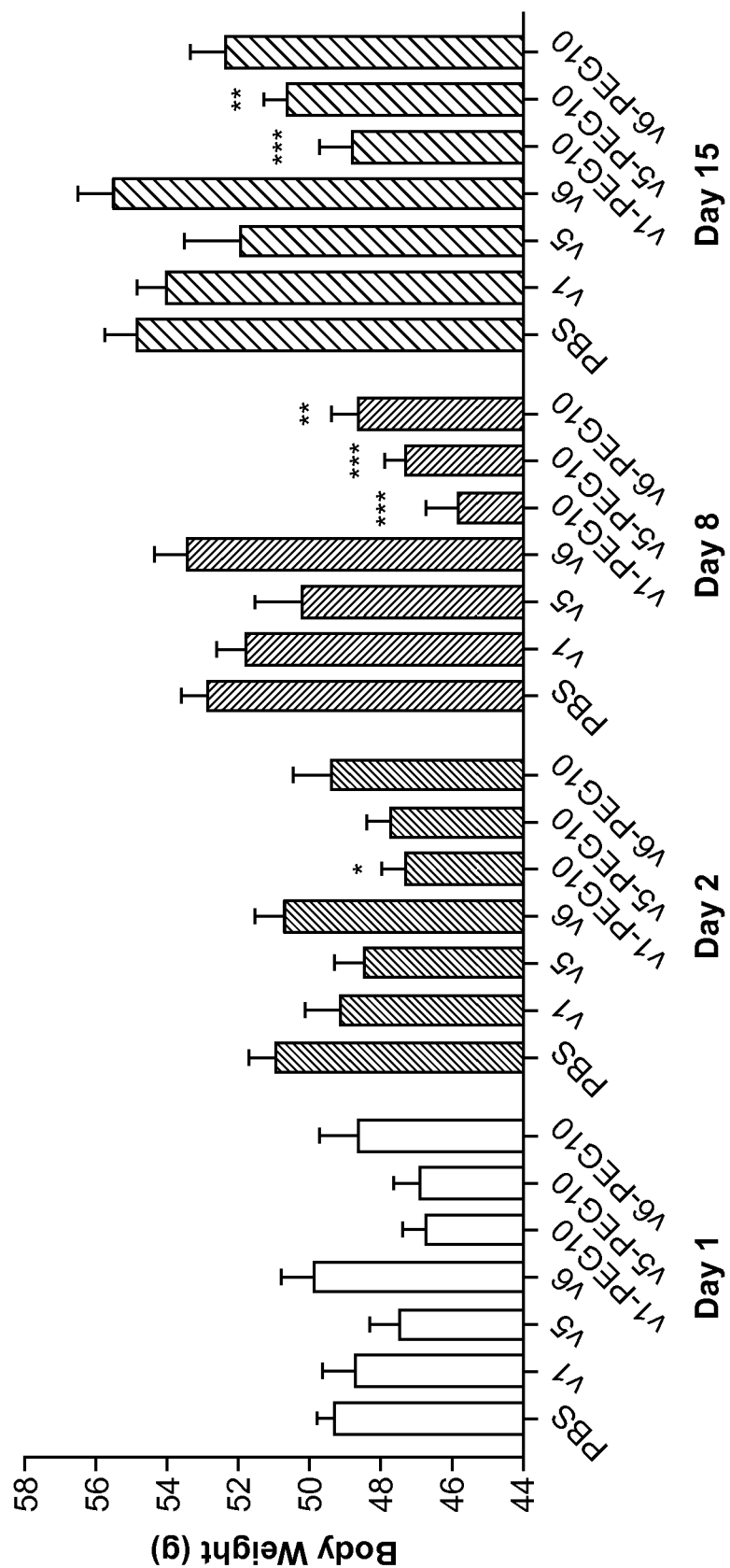
FIG. 13 depicts the effect of recombinant, site-specifically PEGylated GDF15 muteins on body weight compared to that of the corresponding non-PEGylated GDF15 muteins in ob/ob mice. Mice received a single s.c. dose of vehicle; non-PEGylated (2 mg/kg) v1, v5 or v6; or PEGylated (2 mg/kg) v1, v5 or v6 (see FIG. 2). For day 1, body weight was measured 16 hours following dosing, and then on days 2, 8 and 15. In each group of mice, n=5, and p-values were determined by one-way ANOVA comparing food intake at each time point with PBS vehicle control.

As depicted in FIG. 13, administration of a single dose of recombinant GDF15 muteins resulted in significantly decreased body weight, relative to PBS vehicle control-injected ob/ob mice, at specific time points on days 1, 2, 8 and 15 respectively. For day 1, body weight measured 16 hours following the first dose was as follows: vehicle control 49.3 g, v1 48.7 g (ns), v5 47.5 g (ns), v6 49.9 g (ns), v1-PEG10 46.8 g (ns), v5-PEG10 46.9 g (ns) and v6-PEG10 48.6 g (ns). Measurements made during the day 2-day 15 time period were taken at approximately the same time (9:30 a.m.) each day. For day 2, body weight was as follows: vehicle control 51.0 g, v1 49.1 g (ns), v5 48.5 g (ns), v6 50.7 g (ns), v1-PEG10 47.3 g (*, p<0.05), v5-PEG10 47.7 g (ns), and v6-PEG10 49.4 g (ns). For day 8, body weight was as follows: vehicle control 52.9 g, v1 51.7 g (ns), v5 50.2 g (ns), v6 53.4 g (ns), v1-PEG10 45.8 g (*, p<0.001), v5-PEG10 47.3 g (*, p<0.001), and v6-PEG10 48.7 g (, p<0.01). For day 15, body weight was as follows: vehicle control 54.8 g, v1 54.0 g (ns), v5 52.0 g (ns), v6 55.5 g (ns), v1-PEG10 48.8 g (*, p<0.001), v5-PEG10 50.6 g (**, p<0.01) and v6-PEG10 52.4 (ns). In each group of mice, n=5, and p-values were determined by two-way ANOVA comparing body weight at each time point with PBS vehicle control.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A GDF15 mutein comprising:
   a polypeptide comprising the amino acid sequence set forth in:
   (i) SEQ ID NO: 5;
   (ii) SEQ ID NO: 9; or
   (iii) SEQ ID NO: 11.

2. The GDF15 mutein of claim 1, wherein the polypeptide comprises an albumin fusion, Fc-fusion, or fusion with a PEG mimetic.

3. The GDF15 mutein of claim 1, wherein the polypeptide is pegylated.

4. The GDF15 mutein of claim 3, wherein the pegylation increases the solubility of the peptide.

5. The GDF15 mutein of claim 1, wherein the polypeptide is produced recombinantly.

6. A nucleic acid molecule encoding the polypeptide of claim 1.

7. The nucleic acid molecule of claim 6, wherein the nucleic acid molecule is operably linked to an expression control element that confers expression of the nucleic acid molecule encoding the polypeptide in vitro, in a cell, or in vivo.

8. A vector comprising the nucleic acid molecule of claim 6.

9. The vector of claim 8, wherein the vector comprises a viral vector.

10. A transformed host cell that expresses the polypeptide of claim 1.

11. A pharmaceutical composition, comprising the GDF15 mutein of claim 1, and a pharmaceutically acceptable diluent, carrier or excipient.

12. The pharmaceutical composition of claim 11, further comprising at least one additional prophylactic or therapeutic agent.

13. A sterile container comprising the pharmaceutical composition of claim 11.

14. The sterile container of claim 13, wherein the sterile container is a syringe.

15. A kit comprising the sterile container of claim 13.

16. The kit of claim 15, further comprising a second sterile container comprising at least one additional prophylactic or therapeutic agent.

17. A method of treating obesity or hyperglycemia in a mammalian subject, comprising administering to the mammalian subject a therapeutically effective amount of the GDF15 mutein of claim 1.

18. The method of claim 17, wherein the polypeptide comprises an albumin fusion, Fc-fusion, or fusion with a PEG mimetic.

19. The method of claim 17, wherein the polypeptide is pegylated.

20. The method of claim 19, wherein the pegylation increases solubility.

21. The method of claim 17, wherein the method comprises treating hyperglycemia in the mammalian subject and wherein the administering results in a reduction in blood glucose in the mammalian subject.

22. The method of claim 17, wherein the method comprises treating obesity in the mammalian subject and wherein the administering results in a reduction in body weight in the mammalian subject.

23. The method of claim 17, wherein the method comprises treating obesity in the mammalian subject and wherein the administering results in a reduction in food intake by the mammalian subject.

24. The method of claim 17, wherein the mammalian subject has diabetes mellitus.

25. The method of claim 17, wherein the mammalian subject is human.

26. The method of claim 25, wherein the human is obese.

27. The method of claim 25, wherein the human has diabetes mellitus.

28. The method of claim 17, wherein the administering is by parenteral injection.

29. The method of claim 28, wherein the parenteral injection is subcutaneous.

30. The method of claim 21, wherein the polypeptide is pegylated.

31. The method of claim 22, wherein the polypeptide is pegylated.

32. The method of claim 23, wherein the polypeptide is pegylated.

33. The method of claim 24, wherein the polypeptide is pegylated.

34. The method of claim 25, wherein the polypeptide is pegylated.

\* \* \* \* \*